(12) United States Patent
Broenstrup et al.

(10) Patent No.: US 11,072,590 B2
(45) Date of Patent: Jul. 27, 2021

(54) 1,4,7,10-TETRAZACYCLODODECANE BASED AGENTS TO TARGET BACTERIA AND ITS USE

(71) Applicant: HELMHOLTZ-ZENTRUM FUER INFEKTIONSFORSCHUNG GMBH, Braunschweig (DE)

(72) Inventors: Mark Broenstrup, Braunschweig (DE); Haiyu Hu, Wolfenbuettel (DE); Galina Sergeev, Wolfsburg (DE); Bushra Rais, Lucknow (IN); Kevin Ferreira, Braunschweig (DE); Verena Fetz, Braunschweig (DE)

(73) Assignee: HELMHOLTZ-ZENTRUM FUER INFEKTIONSFORSCHUNG GMBH, Braunschweig (DE)

(*) Notice: Subject to any disclaimer, the term of this patent is extended or adjusted under 35 U.S.C. 154(b) by 168 days.

(21) Appl. No.: 15/503,783

(22) PCT Filed: Aug. 18, 2015

(86) PCT No.: PCT/EP2015/068914
§ 371 (c)(1),
(2) Date: Feb. 14, 2017

(87) PCT Pub. No.: WO2016/026841
PCT Pub. Date: Feb. 25, 2016

(65) Prior Publication Data
US 2017/0240582 A1 Aug. 24, 2017

(30) Foreign Application Priority Data
Aug. 18, 2014 (EP) ...................................... 14181231

(51) Int. Cl.
| | |
|---|---|
| *C07D 257/02* | (2006.01) |
| *C07D 403/14* | (2006.01) |
| *C07D 491/16* | (2006.01) |
| *A61K 49/00* | (2006.01) |
| *C07H 17/04* | (2006.01) |
| *C12Q 1/16* | (2006.01) |

(52) U.S. Cl.
CPC ........ *C07D 257/02* (2013.01); *A61K 49/0023* (2013.01); *A61K 49/0032* (2013.01); *A61K 49/0052* (2013.01); *C07D 403/14* (2013.01); *C07D 491/16* (2013.01); *C07H 17/04* (2013.01); *C12Q 1/16* (2013.01); *G01N 2800/26* (2013.01)

(58) Field of Classification Search
None
See application file for complete search history.

(56) References Cited

U.S. PATENT DOCUMENTS

2012/0219500 A1  8/2012  Sakurai et al.

OTHER PUBLICATIONS

Wu et al. Sequestration of copper from beta-amyloid promotes selective lysis by cyclen-hybrid cleavage agents. 2008 J. Biol. Chem . 283: 31657-31664. (Year: 2008).*
Grass, G. et al. Metallic Copper as an Antimicrobial Surface. Applied and Environmental Microbiology 77, 1541-1547 (2011).
Jakobsche, C.E. et al. Reprogramming Urokinase into an Antibody-Recruiting Anticancer Agent. ACS Chemical Biology 7, 316-321 (2011).
Jagadish, B. et al. On the synthesis of 1,4,7-tris(tert-butoxycarbonylmethyl)-1,4-7,10-tatraazacyclododecane. Tetrahedron Letter 562,2058-2061(2011).
Rho, H.S. et al. Studies on depigmenting activities of dihydroxyl benzamide derivatives containing adamantane moiety. Bioorganic & Medicinal Chemistry Letters 19, 1532-1533 (2009).
Albrecht, M. et al. Hierarchical self-assembly of metallo-dendrimers. Dalton Transactions 39, 7220-7222 (2010).
Jain, P.K., et al. Int Ed Engl. Jan. 28, 2013;52(5):1404-9.
Sheikh S. et al. "Evaluation the diagnostic and chemotherapeutic potential of vancomycin-derived imaging aonjugates", Medicinal Chemistry, Bentham Science Publishers Ltd, NL, vol. 8, No. 6, Nov. 1, 2012, pp. 1163-1170.
Albert R. et al "Direct Synthesis of [DOTA-DPhe<1>]~0ctreotide and [DOTA-DPhe<1>,Tyr<3>-Octreotide (SMT487): Two Conjugates for Systhemic Delivery of Radiotherapeutical Nuclides to Somatostatin Receptor Positive Tumors in Man", Bioorganic & Medicinal Chemistry Letter, Pergamon, Amsterdam, NL, vol. 8, np. 10, May 19, 1998, pp. 1207-1210.
Tengfei Zheng et al. "Soderophore-Mediated Cargo Delivery to the Cytoplasm of *Escherichia coli* and *Pseudomonas aeroginiosa*: Syntheses of Monofunctionalized Enterobactin Scaffolds and Evaluation of Enterbactin-Cargo Conjugate Uptake", Journal of American Chemical Society, vol. 134, No. 44, Nov. 7, 2012, pp. 18388-18400.
Amaury Dy Moulinet D'Herdemare et al "Design of Iron chelators: Syntheses and iron (III) complexing abilities of tripodal tris-bidentate ligands", Biometals, Kluwer Academic Publishers, BO, vol. 19, No. 4, Aug. 1, 2006, pp. 349-366.
Emily L. Que et al. "Metals in Neurobiology: Probing Their Chemistry and Biology with Molecular Imaging", Chemical Reviews, vol. 108, No. 5, May 1, 2008, pp. 1517-1549.

(Continued)

*Primary Examiner* — Jennifer Lamberski
(74) *Attorney, Agent, or Firm* — W&C IP

(57) ABSTRACT

The present invention relates to new compounds comprising a siderophore moiety as well as a core structure able to chelate a metal ion. Optionally, the compounds may have additionally a moiety with a functional element including a marker molecule, a bioactive agent, an activity based probe suitable to monitor the aberrant expression or activity of proteins involved in the initiation and progression of bacterial infection, or a compound useful for bacterial inhibition. In a further aspect, the present invention provides a pharmaceutical composition containing said compound, for example, said pharmaceutical composition is an antibiotic. Additionally, the present invention relates to the use of said compounds in diagnostic methods, in particular, imaging methods including SPEC, PET or MRI. In an embodiment of the present invention, the compound is part of a theranostic composition having both, therapeutic as well as diagnostic activities.

12 Claims, 6 Drawing Sheets

(56) References Cited

OTHER PUBLICATIONS

Sabesan Yoganathan et al. "Chemical synthesis and biomedical evaluation of gallidermin-siderohore conjugates", Organic & Biomolecular Chemistry, vol. 9, No. 7, Jan. 1, 2011, p. 2133.
James M. Harrington et al "Synthesis and Iron Sequestration Equilibria of Novel Exocyclic 3-Hydroxy-2-pyridinone Donor Group Siderophore Mimics", Inorganic Chemistry. vol. 49, No. 18, Sep. 20, 2010, pp. 8208-8221.
Leriche, et al. Bioorg. Med. Chem. 20 (2012) 571-582.
Timothy A. Wencewicz et al "Biscathecholate-Monohydrixamate Mixed Ligand Siderophore-Carbacephalospori Conjugates are Selective Sideromycin Antibiotics that Target Acinetobacter baumannii", Journal of Medical Chemistry, vol. 56, No. 10, May 23, 2013, pp. 4044-4052.
Tengfei Zhang et al. "Enterobactin-Mediated Delivery of [beta]-Lactam Antibiotics Enhances Antibacterial Activity against Pathogenic *Escherichia coli*", Journal of the Ameircan Chemical Society. vol. 136, No. 27, Jul. 9, 2014, pp. 9677-9691.
Stephen J. Milner et al. "Probing linker design in citric acid-ciprofloxacin conjugates", Bioorganic & Medicinal Chemistry, vol. 22, No. 16, Aug. 1, 2014, pp. 4499-4505.

\* cited by examiner

… (US 11,072,590 B2)

1,4,7,10-TETRAZACYCLODODECANE BASED AGENTS TO TARGET BACTERIA AND ITS USE

The present invention relates to new compounds comprising a siderophore moiety as well as a core structure able to chelate a metal ion. Optionally, the compounds may have additionally a moiety with a functional element including a marker molecule, a bioactive agent, an activity based probe suitable to monitor the aberrant expression or activity of proteins involved in the initiation and progression of bacterial infection, or a compound useful for bacterial inhibition. In a further aspect, the present invention provides a pharmaceutical composition containing said compound, for example, said pharmaceutical composition is an antibiotic. Additionally, the present invention relates to the use of said compounds in diagnostic methods, in particular, imaging methods including SPEC, PET or MRI. In an embodiment of the present invention, the compound is part of a theranostic composition having both, therapeutic as well as diagnostic activities.

PRIOR ART

Infections caused by multidrug-resistant gram-negative bacteria result in thousands of deaths per year and are the source of considerable concern in the medical community. These multidrug-resistant Gram-negative bacteria particularly occur in hospital settings representing a major problem in hospitals. The major pathogens involved in the development of multidrug-resistance of either Gram-positive or Gram-negative bacteria, which are also called MDR strains (multidrug-resistant strains) include but not limited to *Escherichia coli, Enterococcus faecium, Staphylococcus aureus, Klebsiella pneumoniae, Acinetobacter baumanii, Pseudomonas aeruginosa* and *Enterobacter spec*. The mechanisms underlying the resistance against common antibiotics in the different pathogens include production of antibiotic inactivating enzymes, change of the binding side, thus, avoiding binding thereof as well as preventing binding or entry of the antibiotic into the cell, for example as described for some of *Pseudomonas aeruginosa* strains.

*Pseudomonas aeruginosa* represents about 10% of all infections occurring in hospital. Typically, these infections are lung, skin and wound infection as well as infection of the urogenital tract.

About 3% of all cases of sepsis are due to *Pseudomonas aeruginosa* whereby this type of sepsis is the one having the highest lethal rate among all forms of sepsis. Typically, patients having suppressed immune systems are susceptible to *Pseudomonas aeruginosa* infection. Accordingly, most of the patients afflicted therewith are patients on intensive medical care, burn or oncological care units.

As indicated above, among several mechanisms of antibiotic resistance in gram-negative bacteria as well as in other pathogens, a major problem is the low permeability of their outer membrane which serves as a barrier to prevent antibiotic uptake. Thus, there is still a need of active agents circumventing this mechanism of resistance. In addition, to identify and to diagnose the pathogen as well as for the determination of location and spatial distribution of the pathogen, diagnostic tools are required.

The present invention aims in providing new compounds suitable for diagnosing as well as treating infections by pathogens, in particular, gram-negative bacteria. That is, the development of methods to overcome the permeability mediated resistance represents an important therapeutic goal as well as an important diagnostic goal.

Siderophore are small, high affinity metal ion, typically iron ion, chelating compounds secreted by microorganisms, such as bacteria, and fungi but also grasses. Siderophores are among the strongest soluble $Fe^{3+}$ binding agents known. For chelating the metal ion, thus, binding the metal ion, various functional groups are known in siderophores including catecholate group, salicylate group, hydroxymate group, oxazole-ring, thiazole-ring, citrate-hydroxmate group, α-keto carboxylate group, α-hydroxy-carboxylate-group or carboxylic acid amid group. Typically at least two or at least three of these functional groups, also known as siderophore forming group, are present in the siderophore molecule.

Although iron represents an essential element for most life for processes such as respiration and DNA synthesis, iron and iron ions, in particular $Fe^{3+}$ ion cannot be readily utilised by organisms. Microbes siderophores scavenge iron from mineral phases by formation of soluble $Fe^{3+}$ complexes that can be taken up by active transport mechanisms. Siderophores usually form a stable hexadentate octahedral complex with metal ions, typically $Fe^{3+}$ ions. If there are less than six donor atoms water can also coordinate. Typically, three bidentate ligands per molecules for chelating a single ferric ion forming a hexadentate complex are present. As noted before, the major groups for chelating the metal ion, in particular, the FE ion, of siderophores include the catecholates, hydroxamates, N-hydroxy-pyridone and carboxylates. In addition, citric acid can also act as a siderophore. A wide variety of siderophores exist in nature, thus, different organisms release different types of siderophores which are not uptaken by other species.

Typically, the microorganisms produce and release siderophores in case of iron limitation in their environment. The siderophores are excreted into the extracellular environment after manufacture where the siderophores acts to sequester and solubilize the iron. Thereafter, the siderophores are than recognized by cell specific receptors on the outer membrane of the cell and the metal ion siderophore complex is actively transported across the cell membrane. Siderophores have been described as being useful as drugs in facilitating iron mobilization in humans, especially in the treatment of iron diseases, due to their high affinity for iron. Moreover, it is speculated to use these structures to carry drugs into cells by preparation of conjugates between siderophores and anti-microbial agents.

Microbial iron transport (siderophore) mediated drug delivery makes use of the recognition of siderophores as iron delivery agents in order to have the micro assimilated siderophore conjugates with attached drugs. In addition, agriculture applications are considered.

Chelation describes a particular way that molecules bind metal ions. According to IUPAC chelation involves the formation or presence of two or more separate coordinate bonds between a polydentate ligand and a single central atom. Typically, the ligands are organic compounds also called chelants, chelators, chelating agents or sequestering agents. Chelators are used in producing nutritional supplements, fertilizers, chemical analysis, water softeners, commercial products such as shampoos and food preservatives, medicine, heavy metal detox and industrial applications. For example, chelation therapy is used to detoxify poisonous metal agents. A typical example of a chelator is a compound or a family of compounds falling under the acronym DOTA. In a narrow sense, DOTA refers to 1,4,7,10-tetraazacyclodo-decane-1,4,7,10-tetraacetic acid consisting of a central 12-membered tetraaza ring. Complexes with metal ions have medical applications as contrast agents and in cancer treatment. Today under the acronym DOTA a lot of derivatives of DOTA as well as structures not having a tetracarboxylic acid are used. For example DOTAM refers to the DOTA derivative 1,4,7,10 tetraazacyclododecane-1,4,7,10 tetraaecetic acid amid. In medicine, DOTA-tate is described as a substance bounding to various radionuclides. In addition, $^{90}$Y-DOTA-biotin is described in pretargeting radio immunotherapy. Further, Yttrium containing drugs are described in the art wherein DOTA chelates the Y ions. Complexes of $Gd^{3+}$ and DOTA are used as gardolinium-based MRI contrast agent.

The aim of the present invention is to provide new compounds useful as theranostics in medicine, i.e. allowing diagnostic and therapy of diseases, in particular, infectious diseases by microorganisms.

BRIEF DESCRIPTION OF THE PRESENT INVENTION

In a first aspect, the present invention relates to a compound of the general formula (I), in any of their stereoisomeric forms or a mixture of stereoisomeric forms in any ratio, or a pharmaceutically acceptable salt, solvate or hydrate or a pharmaceutically acceptable formulation thereof:

$$G_m\text{-}C(\text{---}B)_n \quad (I)$$

with C being a structure able to chelate a metal ion M;
M is a metal ion and may be present or absent;
B are independently from one another identical or different and at least one B may represent singly or with one or two other moieties of B a siderophore; and
G representing a moiety with a functional element whereby said functional element is a marker molecule, a bioactive agent, an activity based probe suitable to monitor the aberrant expression or activity of proteins involved in the initiation and progression of bacterial infection, or a compound useful for bacterial inhibition or a hydrogen atom; and
n is an integer of 1, 2 or 3 and m is an integer of 0 or 1.

That is, the present inventors recognized that combining a core moiety able to chelate a metal ion, like copper ion, in combination with a siderophore activity allows to introduce the metal ions into pathogens. In addition, the present inventors provide compounds having a siderophore acting moiety and a moiety with a functional element. Said element may be a marker molecule, a bioactive agent, an activity based probe suitable to monitor the aberrant expression or activity of proteins involved in the initiation and progression of bacterial infection, or a compound useful for bacterial inhibition. In addition, a combination of all three moieties may be possible.

The present invention provides a new theranostic composition, for example, theranostic composition for imaging including SPEC or PET or MRI wherein the positively charged metal ion are suitable metal ions useful for said methods and these ions are chelated within the core moiety.

In a preferred embodiment, the core moiety is a DOTA derivative, e.g. as shown in formula (III).

In a further aspect, the present invention relates to a pharmaceutical composition containing the compounds according to the present invention. Said pharmaceutical compositions are useful as antibiotic, e.g. as an active ingredient against pathogens including MDR pathogens. Moreover, the present invention relates to the use of said compounds for diagnosis as well as a vehicle for the transport of a compound of interest into microorganisms transporting actively siderophores into their cells.

In particular, the present invention provides theranostic composition.

BRIEF DESCRIPTION OF THE DRAWINGS

In FIG. 1, a compound according to the present invention is shown with m=3 and Z being a catecholate based siderophoric group with Ac instead of H whereby the three groups can coordinate $Fe^{3+}$, thus, allowing uptake by bacteria. The core moiety is a DOTA derivative.

FIG. 2.

FIG. 3 is a further embodiment of the present invention wherein the functional element is coumarin 343. While compound 10 does not contain a chelated metal ion, compound 11 contains a $Cu^{2+}$ ion coordinated in the center of the DOTA core moiety.

FIG. 4 shows the visualization of a fluorescent siderophore linked compound (DOTAM-Cy5.5) at the site of bacteria: P. aeruginosa (PA01 WT) was subcutaneously injected at the back of interferon-β luciferase reporter mouse. Control mice without bacterial infection were included. Mice were injected intravenously with Cy5.5 conjugated compound containing siderophore (DOTAM-Cy5.5) (A) and control group was injected with compound without siderophores DOTA-Cy5.5 only (B). Fluorescent imaging was performed and monitored for a day (A and B). Bioluminescent imaging of the mice was done after 5 hours by injecting luciferin; mice with DOTAM-Cy5.5 (C) and DOTA-Cy5.5 alone (D). Dashed circles in white represent the site of bacterial infection.

FIG. 5 shows the uptake of DOTAM-MG and MG-ester in E. coli Origami DE3 pET23_His cultured in LB-Amp Expression induced for 4 h with IPTG, OD600 adjusted to 2 (100 µl/well) addition of MG-ester (KF10) or DOTAM-MG (KF18) at final concentration of 10 µM recorded fluorescence: EX 610/Em 655.

FIG. 6 shows the DOTAM-MG compound.

FIG. 7 is a scheme of the synthesis of the compound shown in FIG. 6.

FIG. 8 is a scheme showing the synthesis of metal ions chelated in the DOTA derivative DOTAM core unit.

DETAILED DESCRIPTION OF THE PRESENT INVENTION

Figure 1:
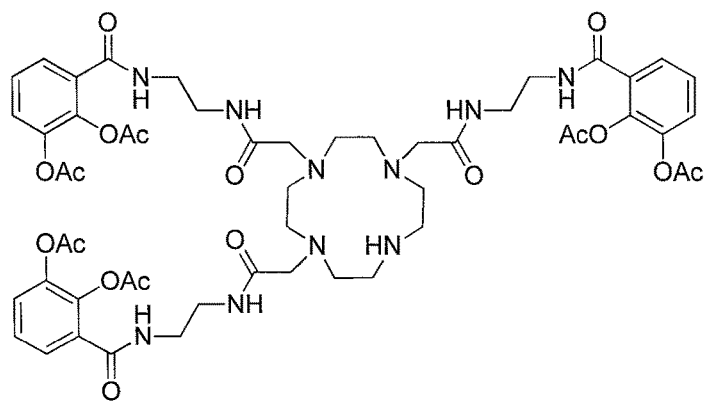
FIG. 1.

In a first aspect, the present invention provides compounds of the general formula (I), in any of their stereoisomeric forms or a mixture of stereoisomeric forms in any ratio, or a pharmaceutically acceptable salt, solvate or hydrate or a pharmaceutically acceptable formulation thereof:

$$G_m\text{-}C(\text{---}B)_n \quad (I)$$

with C being a structure able to chelate a metal ion M;
M is a metal ion and may be present or absent;
B are independently from one another identical or different and at least one B may represent singly or with one or two other moieties of B a siderophore; and
G representing a moiety with a functional element whereby said functional element is a marker molecule, an activity based probe suitable to monitor the aberrant expression or activity of proteins involved in the initiation and progression of bacterial infection, or a compound useful for bacterial inhibition, a bioactive agent, or a hydrogen atom; and n is an integer of 1, 2 or 3 and m is an integer of 0 or 1.

As used herein, the terms "comprising", "comprises" and "comprise of" are synonymous with "including", "includes" or "containing" or "contains" and are inclusive or open ended into not excluded additional, non-recited members, elements or method steps. It will be appreciated that said terms as used herein comprise the terms "consisting of", "consists" and "consist of".

All references cited in the present specification are hereby incorporated by reference in their entirety. In particular, the teachings of all references herein specifically referred to are incorporated by reference.

Unless otherwise indicated, all terms used in disclosing the invention including technical and scientific terms, have the meaning as commonly understood by one of the order skilled in the art to which this inventions belongs. By means of further guidance, term deficiencies are included by appreciate the teaching of the present invention.

As used herein, the similar forms "a", "an" and "the" include both singular and plural references unless the context clearly dictates otherwise.

The term "structure able to chelate of metal ion" or "structure for chelating a metal ion" which are used interchangeably herein, refers to a structure representing a polydentate ligand able to chelate a single metal ion as a single central atom.

Typically, the metal ion is a $M^{2+}$ or $M^{3+}$ ion. For example, the ions may be any one of M being a positively charged metal ion out of the group Gd, Yb, Mn, Cr, Cu, Fe, Pr, Nd, Sm, Tb, Yb, Dy, Ho, Er, Eu, Ga, $^{68}$Ga, $^{64}$Cu, $^{99m}$Tc, $^{177}$Lu, $^{67}$Ga, $^{111}$In, $^{99}$Mo, in particular, useful for imaging, in particular, SPEC or PET or MRI.

The term "metal ion" refers to and include generally the various forms of metallic ions possible including e.g. in case of Fe the ferrous ion, $Fe^{2+}$, or the ferric ion, $Fe^{3+}$ unless otherwise indicated.

In addition, the term "siderophore" refers to chelating compounds forming a stable complex with a metal ion, typically, $Fe^{3+}$. Siderophore are stable, hexadentate, octahedral complexes coordinating the metal ion, typically, the ferric ion.

The term "siderophoric group" or "siderophore forming group" as used herein interchangeably refers to a structure, namely ligands used to chelate the metal ion. For example, the siderophoric group are a group selected from catecholates, hydroxamates, carboxylates and N-hydroxy-pyridone derivatives as known to the skilled person. A comprehensive list of siderophores and siderophoric groups is shown in Hilder R. C. and Kong X., Nat Prod. Rep. 2010, 27, 637-657.

According to the present invention, the term siderophore is generally to be understood in the broader sense by any compound containing at least two, preferably at least three, especially three residues selected from group consisting of hydroxamate, catecholate, α-hydroxy-carboxylate, α-ketocaroxylate, carboxylic acid amide, citrate, hydroxamate and, optionally, fully hydrogenated imidazole, oxazole or triazole.

Under the term "catecholate" typically the two times deprotonated form of catechole is known. According to the present invention, the catecholate residue includes also the fully or partially protonated form, that is, the protonated form of the catecholate is within the term "catecholate" according to the present invention. The same holds true for the other residues identified, in particular, in the non-complexed form of the siderophore typically in the protonated form. That is, under the term "hydroxamate" hydroxam acid residues and under the term "carboxylate" carboxylic acid residues are included. When present in complexed form with a metal ion these residues are typically present in its deprotonated form accordingly.

As used herein, the term "bioactive agent" refers to any agent having a biological effect. The bioactive agent may be a small molecule or may be any compound having interaction with or effect on living matter including peptides and nucleic acids.

The term "alkyl" refers to a saturated aliphatic hydrocarbon including straight chain and branched chain groups. "Alkyl" may be exampled by groups such as methyl, ethyl, n-propyl, isopropyl, n-butyl and the like. Alkyl groups may be substituted or unsubstituted. Substituents may also be themselves substituted. When substituted, the substituent group is preferably, but not limited to, $C_1$-$C_4$ alkyl, aryl, amino, cyano, halogen, alkoxy or hydroxyl.

The term "$C_0$-$C_6$" as used herein include compounds having $C_0$, $C_1$, $C_2$, $C_3$, $C_4$, $C_5$, $C_6$ carbon atoms. The term "$C_0$-$C_4$" include $C_0$, $C_1$, $C_2$, $C_3$, $C_4$ carbon atoms. C1-C4 include $C_1$, $C_2$, $C_3$, $C_4$ carbon atoms. The groups may be present in linear, branched or cyclic form.

The term "cycloalkyl" refers to carbocyclic groups, typically, said carbocyclic group is a monocyclic group. The $C_3$-$C_7$ cycloalkyl group refers to $C_3$, $C_4$, $C_5$, $C_6$, or $C_7$ cycloalkyl.

As used herein, the term "functional element" refers generally to a moiety having a specific biological, chemical or physical functionality. For example, said functionality may be a label or marker, a bioactive agent, an activity based probe suitable to monitor the aberrant expression or activity of proteins involved in the initiation and progression of bacterial infection, or a compound useful for bacterial inhibition. Of course, the functional element may be other moieties having a specific activity.

In this connection, the term "activity-based probe" or "ABP" include a moiety containing two suitable fluorophores attached in a distance suitable for fluorescence energy resonance transfer (FRET) and linked by an ABP cleavable linker. The ABP cleavable linker may be a peptide consisting of two to 12 amino acids, containing cleavage sequences recognized be therapeutically relevant hydrolases including sortase, HTRA, CLP protease, LUN, FTSH or other relevant proteins, may be substituted, including substitution by $C_1$-$C_{16}$ alkyl, polyethylenglykol chains, ethers, alkylamines or other residues. The ABP allows monitoring an aberrant expression or activity of proteins involved in the initiation and progression of bacterial infection.

In addition, the substituents A, L, and Y may form a cleavable linker. That is, the cleavable linker is a linker that is cleaved inside the cell after uptake of the siderophore containing structure according to the present invention. Cleavages may be any biochemical mechanism including hydrolysis, e.g. of hydrazones, amides, esters, etc., or by reduction, e.g. in case of disulphide bonds. The term cleavable linkers describes linker systems, being cleaved either by enzymatic processing e.g. by the action of proteases on said linker or nucleophilic attack by sulfur or oxygen containing residues or hydrolysis due to changes in pH or by irradiation, thereby liberating higher concentration of drug at the site of interest. Examples for cleavable linkers are known by the skilled man in the art and are described in the literature, e.g. G. Leriche et al., Bioorg. Med. Chem. 20 (2012) 571-582 and references cited therein.

Cleavable linker can also be selected from linker groups as indicated in the table 2 below.

TABLE 2

| Cleavage conditions | Cleavable groups |
|---|---|
| Enzymes | Sortase, HtrA, Clp protease, Lon, FtsH |
| Nucleophilic/ basic reagents | Dialkyl dialkoxysilane, cyanoethyl group, sulfone, ethylene glycolyl disuccinate, 2-N-acyl nitrobenzenesulfonamide, a-thiophenylester, unsaturated vinyl sulfide, sulfonamide after activation, malondialdehyde (MDA)-indole derivative, levulinoyl ester, hydrazone, acylhydrazone, alkyl thioester |
| Reducing reagents | Disulfide bridges, azo compounds |
| Photo-irradiation | 2-Nitrobenzyl derivatives, phenacyl ester, 8-quinolinyl benzenesulfonate, coumarin, phosphotriester, bis-arylhydrazone, bimane bi-thiopropionic acid derivative |
| Electrophilic/ acidic reagents | Paramethoxybenzyl derivative, tert-butylcarbamate analogue, dialkyl or diaryl dialkoxysilane, orthoester, acetal, aconityl, hydrazone, b-thiopropionate, phosphoramidate, imine, trityl, vinyl ether, polyketal, alkyl 2-(diphenylphosphino)benzoate derivatives |
| Organometallic and metal catalyst | Allyl ester, 8-hydroxyquinoline ester, picolinate ester |
| Oxidizing reagents | Vicinal diols, selenium compounds |

Cleavable linker can also be selected from acid-labile linker systems such as tert-butyloxycarbonyl, paramethoxybenzyl, dialkyl or diaryldialkoxysylane, orthoester, acetal, b-thio-proponate, ketal, phosphoamidate, hydrazone, vinyl ether, imine, aconityl, trityl, polyketal and such as linker exemplified in scheme 8 of Leriche et al., Bioorg. Med. Chem. 20 (2012) 571-582.

Cleavable linker can also be selected from photocleavable systems such as ortho-nitrobenzyl derivatives, phenacyl ester derivatives, and others photocleavable linkers such as ortho-notribenzyl based linker, phenacyl ester based linker, 8-quinolinyl benzenesulfonate linker, dicoumarin linker, 6-bromo-7-alkoxycoumarin-4-ylmethoxycarbonyl, bimane based linker, bis-arylhydrazone based linker such as linker exemplified in scheme 8 of Leriche et al., Bioorg. Med. Chem. 20 (2012) 571-582. Cleavable linker can be selected from P. J. Jaun et al, Angew Chem Int Ed Engl. 2013 Jan. 28; 52(5):1404-9.

The term "marker molecule", "marker", or "label" which are used herein interchangeably refers to a label or marker which is preferably capable of producing, either directly or indirectly, a detectable signal. For example, the label or marker molecule may be a radioisotope, a fluorophore or chemiluminescent (chromophore) compound, an enzyme, an imaging agent, magnetic or paramagnetic labels, or a metal ion.

This term, marker molecule, marker or label, include fluorophores. The term "fluorophore" describes compounds out of the group dimethylaminocoumarin derivative, preferably 7-dimethylaminocoumarin-4-acetic acid succinimidyl ester, dansyl, 5/6-carboxyfluorescein and tetramethylrhodamine, BODIPY-493/503, BODIPY-FL, BODIPY-TMR, BODIPY-TMR-X, BODIPY-TR-X, BODIPY630/550-X, BODIPY-650/665-X, Alexa 350, Alexa 488, Alexa 532, Alexa 546, Alexa 555, Alexa 635, Alexa 647, Cyanine 3 (Cy 3), Cyanine 3B (Cy 3B), Cyanine 5 (Cy 5), Cyanine 5.5 (Cy 5.5), Cyanine 7 (Cy 7), Cyanine 7.5 (Cy 7.5), ATTO 488, ATTO 532, ATTO 600, ATTO 655, DY-505, DY-547, DY-632, DY-647; Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots). Most preferred is a fluorophore selected from the group consisting of a dimethylaminocoumarin derivative, preferably 7-dimethylaminocoumarin-4-acetic acid succinimidyl ester, dansyl, 5/6-carboxyfluorescein and tetramethylrhodamine, BODIPY-493/503, BODIPY-FL, BODIPY-TMR, BODIPY-TMR-X, BODIPY-TR-X, BODIPY630/550-X, BODIPY-650/665-X, Alexa 350, Alexa 488, Alexa 532, Alexa 546, Alexa 555, Alexa 635, Alexa 647, Cyanine 3 (Cy 3), Cyanine 3B (Cy 3B), Cyanine 5 (Cy 5), Cyanine 5.5 (Cy 5.5), Cyanine 7 (Cy 7), Cyanine 7.5 (Cy 7.5), ATTO 488, ATTO 532, ATTO 600, ATTO 655, DY-505, DY-547, DY-632, DY-647] Preferred examples of optical imaging moieties are the cyanine dyes out of the group Carbacyanines, Oxacyanines, Thiacyanines and Azacyanines. Cyanine dyes are compounds defined by a polyene chain containing an odd number of carbon atoms linked by alternating single and multiple, preferably double, carbon-carbon bonds, terminated at either end by an amino group, one of which is quaternised. The cyanine and analogues aryl-linker-aryl chromophores optionally carry pendant or fused ring substituents. The cyanine dyes are particularly useful due to the wide range of spectral properties and structural variations available. A range of cyanine dyes are well known and tested, they have low toxicity, and are commercially available. The cyanine dyes are a single family of highly intense dyes with good aqueous solubility. They are pH insensitive between pH 3-10, exhibit low non-specific binding, and are more photostable than fluorescein.

The term "compound useful for bacterial inhibition" or "compound for bacterial inhibition" refers to a compound which interacts with bacterial targets, which can lead to, for example, inhibition of bacterial growth, killing of bacteria, a reduction of their virulence or a modulation of their functioning.

The term "theranostic" refers to a compound enabling therapy as well as diagnostic. For example, the compound of the present invention has diagnostic properties allowing imaging of microorganisms, in particular, bacterial cells which transported the compound according to the present invention due to the siderophoric properties into the cell. The therapeutic aspect, namely, the active agent may be present in the functional element G or may be the metal ion M chelated in C, the core structure.

In an embodiment of the present invention, when $Z^1$, $Z^2$ or $Z^3$ is a fluorophore, the ABP may consist of a second fluorophore attached in a distance allowing FRET and linked by a ABP cleavable linker as defined above, such as upon cleavage of said linker system fluorescence intensity of the system changes.

Alternatively, the ABP may contain a reactive capture group like AOMK (AcylOxyMethylKetone), an epoxide, fluoroketone or similar known to the one skilled in the art that can react with the active center of for example a protease of interest e.g. with a reactive cycteine to form a new covalent bond, thereby labelling said enzyme and attaching one part of the molecule (either containing Z or the DOTA) to the target protein.

In an embodiment of the present invention, B is independently from one another identical or different having the structure (II)

A-L-Y-Z                    (II)

A, L and Y may be present or absent, and
whereby A is independently of one another, identical or different, and are independently of one another selected from a bond, —(C$_0$-C$_4$)-alkyl-C(O)—N(R$^1$)—, —(C$_0$-C$_4$)-alkyl-P(O)$_t$—N(R$^1$)—, —(C$_0$-C$_4$)-alkyl-S(O)$_t$—N(R$^1$)—, —(C$_0$-C$_4$)-alkyl-N(R$^2$)—C(O)—N(R$^1$)— and —(C$_0$-C$_4$)-alkyl-N(R$^1$)—C(O)—;

R$^1$ and R$^2$ are independently of one another selected from hydrogen, (C$_1$-C$_4$)-alkyl, (C$_3$-C$_7$)-cycloalkyl and —(C$_1$-C$_4$)-alkyl-(C$_3$-C$_7$)-cycloalkyl;

t is selected from 1 and 2;

L is independently of one another, identical or different, and are independently of one another selected from a bond, (C$_1$-C$_{18}$)-alkyl, —(CH$_2$)$_u$[—O—(CH$_2$)$_p$]$_q$— u, q and p are independently of one another identical or different and are the integers zero, 1, 2, 3, 4, 5, 6, 7, 8, 9 or 10;

Y is independently of one another, identical or different, and are independently of one another selected from a bond, —(C$_0$-C$_4$)-alkyl-N(R$^1$)—, —(C$_0$-C$_4$)-alkyl-C(O)—N(R$^1$)—, —N(R$^1$)—C(O)—(C$_0$-C$_6$)-alkyl-, —(C$_0$-C$_4$)-alkyl-S(O)$_t$—N(R$^1$)—, —(C$_0$-C$_4$)-alkyl-N(R$^2$)—C(O)—N(R$^1$)—, —(C$_0$-C$_4$)-alkyl-N(R$^1$)—C(O)—,

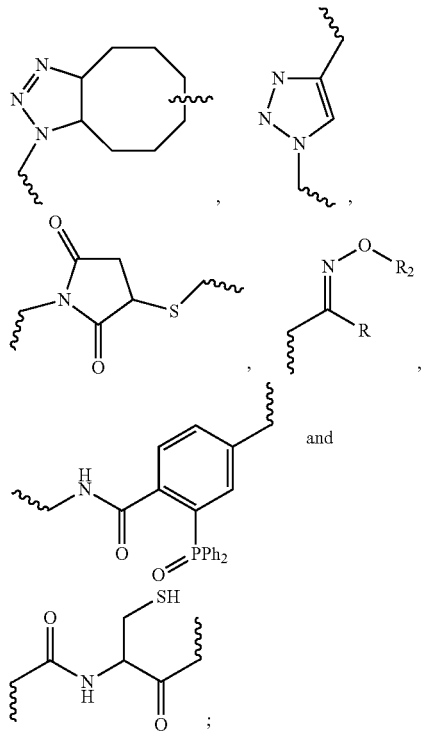

R$^1$ and R$^2$ are independently of one another selected from hydrogen, (C$_1$-C$_4$)-alkyl, (C$_3$-C$_7$)-cycloalkyl and —(C$_1$-C$_4$)-alkyl-(C$_3$-C$_7$)-cycloalkyl;

t is selected from 1 and 2;

Z is independently of one another, identical or different, and are independently of one another selected from: a hydrogen atom, a marker molecule, an activity based probe for monitoring the aberrant expression or activity of proteins involved in the initiation and progression of bacterial infection, or a compound for bacterial inhibition, or a siderophore (siderophore forming group) with the proviso that at least one of Z represents a siderophore (siderophore forming group) or at least two of identical Z present in different B may form a siderophore.

In an embodiment of the present invention, the core moiety is a compound of the formula (III) or (IIIa), namely, a DOTA group.

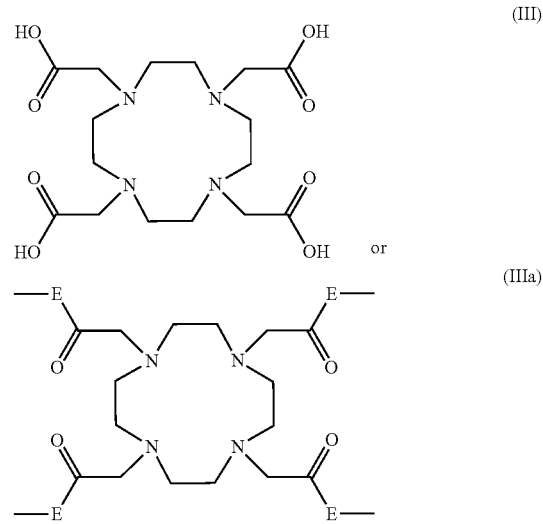

wherein E is O or N.

DOTA refers to the template 1,4,7,10-tetraazacyclododecane-1,4,7,10-tetraacetic acid. The term "DOTA" as used by the skilled in the art and as identified herein, refers not only to the template 1,4,7,10-tetraazacyclododecane-1,4,7,10-tetraacetic acid but also to DOTA derivatives having the same function, namely, enabling to chelate a metal ion in the centre and, in addition, allowing multivalent attachment of side groups. A representative of this DOTA derivative is DOTAM, 1,4,7,70-tetraazacyclododecane-1,4,7,10 tetraacetic acid amide as shown as a core unit in FIGS. 1 to 3. That is, the multivalently decorated DOTA derivatives represent a defined, monomeric unit able to complex metal ion, like copper ions, having bacteria growth inhibiting activity. In addition, due to the siderophoric groups forming a siderophore unit, targeting of this compound is possible to bacteria or other organisms actively transporting said siderophore into the cell. The compounds of the present invention can be therefore used for the localized administration of a therapeutic agent and/or a diagnostic agent selectively binding to bacteria or other organisms actively transporting the siderophore into cell, e.g. for real time in vivo imaging and treatment of bacterial infections. The compounds according to the present invention are designed to actively target and adhere to bacteria, thus, preventing significant systemic plasma concentration and exposure of the whole body of these diagnostic agent and therapeutic agent and, thus, serve to prevent adverse side effects.

In an embodiment, the siderophoric group Z is selected from the siderophore forming groups of catecholates, hydroxamates, N-hydroxy-pyridone derivative or carboxylates whereby the siderophore forming groups are identical.

In an embodiment, n is 3 and m is 1 which means that the compound according to the present invention has three side groups (arms) B each of them having a siderophoric group, typically the identical siderophoric group, while the fourth side group is a group G having a moiety with a functional element.

The substituent G representing the moiety with a functional element may be a group having the structure (V)

$$\text{A-L-Y—K} \quad (V)$$

A, L and Y may be present or absent, and are defined as above;

K is a hydrogen atom, a fluorophore for optical imaging; a bioactive agent, an activity based probe (ABP) for monitoring the aberrant expression or activity of proteins involved in the initiation and progression of bacterial infection or a compound for bacterial inhibition including an antibiotic. In addition, as mentioned before, A, L and Y may form a cleavable linker as defined above.

A suitable embodiment is represented by the structure of general formula (IV)

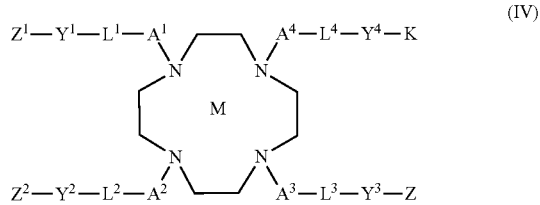

wherein each of A, L, Y, Z, and K are defined as above.

In an embodiment, the compound is a compound of the general formula (VI):

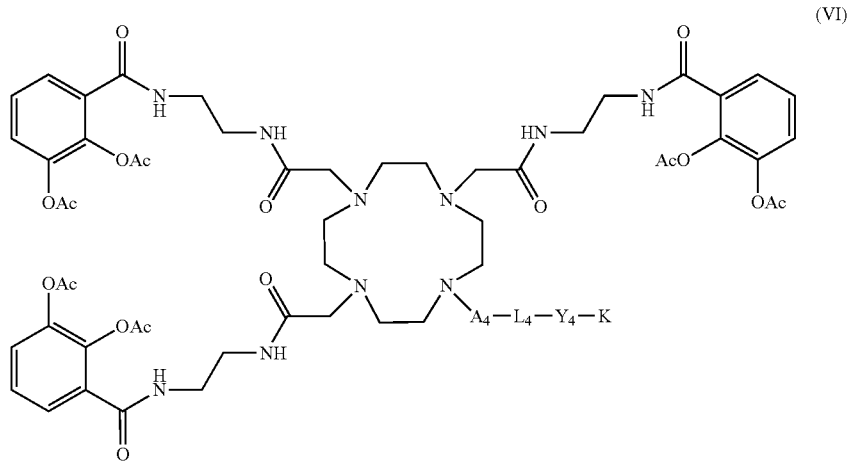

wherein A4, L4, Y4 and K are as defined above. The siderophoric group Z is a catecholate residue with Ac. Alternatively, H may be present instead of Ac.

In an embodiment of the present invention, residues $A^1$-$L^1$-$Y^1$-$Z^1$; $A^2$-$L^2$-$Y^2$-$Z^2$; and $A^3$-$L^3$-$Y^3$-$Z^3$; are identical. Furthermore, it is preferred that $Z^1$, $Z^2$ and $Z^3$ being identical a group of:

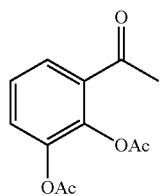 [SMILES: CC(=O)Oc1cccc(C(C)=O)c1OC(C)=O]

Further, the groups $A^1$, $A^2$, $A^3$, $L^1$, $L^2$, $L^3$ and $Y^1$, $Y^2$, and $Y^3$ are identical whereby A is $C_1$ alkyl-C(O)—N(H)—, L is $C_1$ alkyl, and Y is $C_1$ alkyl-NH—.

Moreover, the siderophoric groups may be arranged as follows: in an embodiment, each B of three arms (m=3) represented by the structure (II) contain one siderophoric group. In an alternative embodiment, one arm of B identified with the general structure (II) contains three siderophoric groups in a row. Thus, allowing chelating of the metal ion chelated in the siderophore, typically, a ferric ion.

An example of this group is shown in FIG. 1.

Figure 2A:
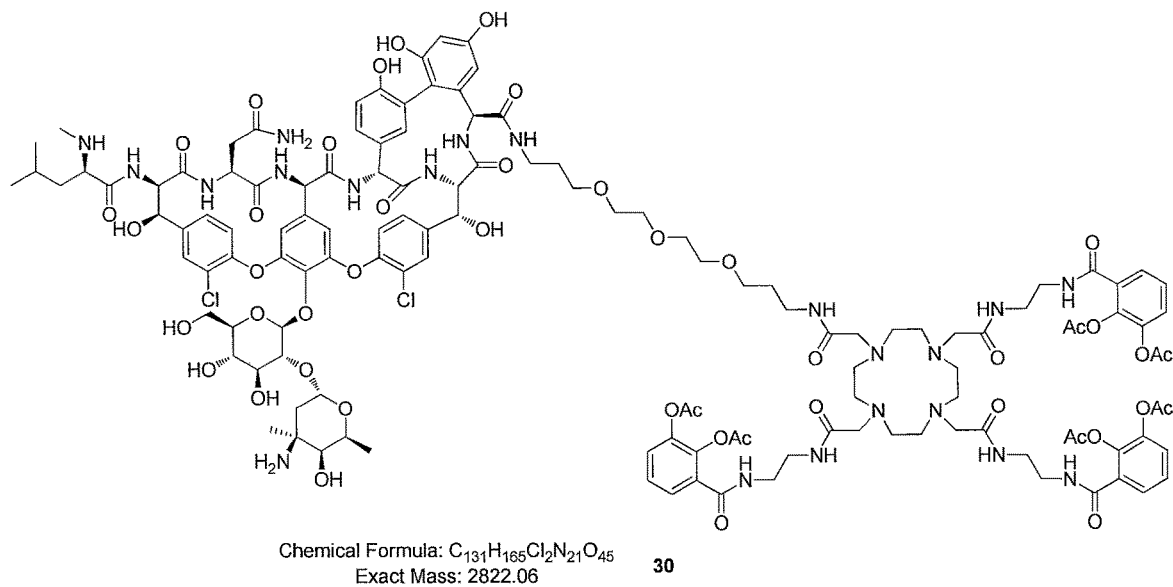
FIG. 2a shows a compound according to the present invention wherein vancomycin is present as a functional element while the other moieties are the same as shown in FIG. 1.

Possible embodiments of the compound according to the present invention are shown in FIG. 2. That is, compound 30, FIG. 2a, shows a compound according to the present invention having a DOTA core unit, a catechol based siderophoric group on each arm one siderophoric group is present whereby the oxygen is present in its acetylated form. Normally, hydrolysation of the acetyl group occurs in situ, thus, a hydroxyl group is present in situ. $A^1$, $A^2$, $A^3$, $L^1$, $L^2$, $L^3$, $Y^1$, $Y^2$, and $Y^3$ are identical whereby A is $C_1$ alkyl-C(O)—N(H)—, L is $C_1$ alkyl, and Y is $C_1$-alkyl-NH—. This structure is bound via the linker $A^4$, $L^4$, $Y^4$ with vancomycin, whereby A is $C_1$ alkyl-C(O)—N(H)—, L is $C_3$-alkyl-O—$C_2$-alkyl-O—$C_2$-alkyl, and Y is $C_1$-alkyl-NH—

Figure 2B:
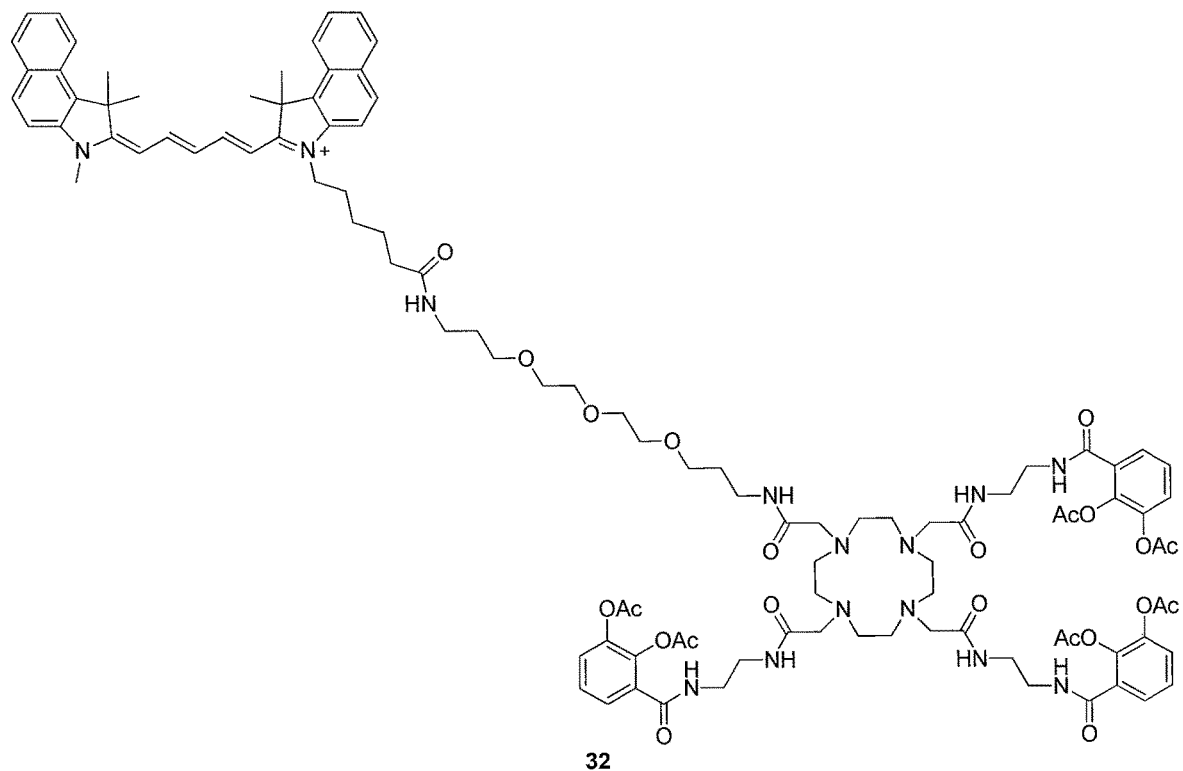
FIG. 2b is a structure of another compound according to the present invention wherein the functional element is a fluorophore.

Another embodiment is shown as compound 32 in FIG. 2b having the same core moiety and the same B moieties while the G moiety is a fluorogenic probe, namely the cyanine dye Cy 5.5.

Figure 3:
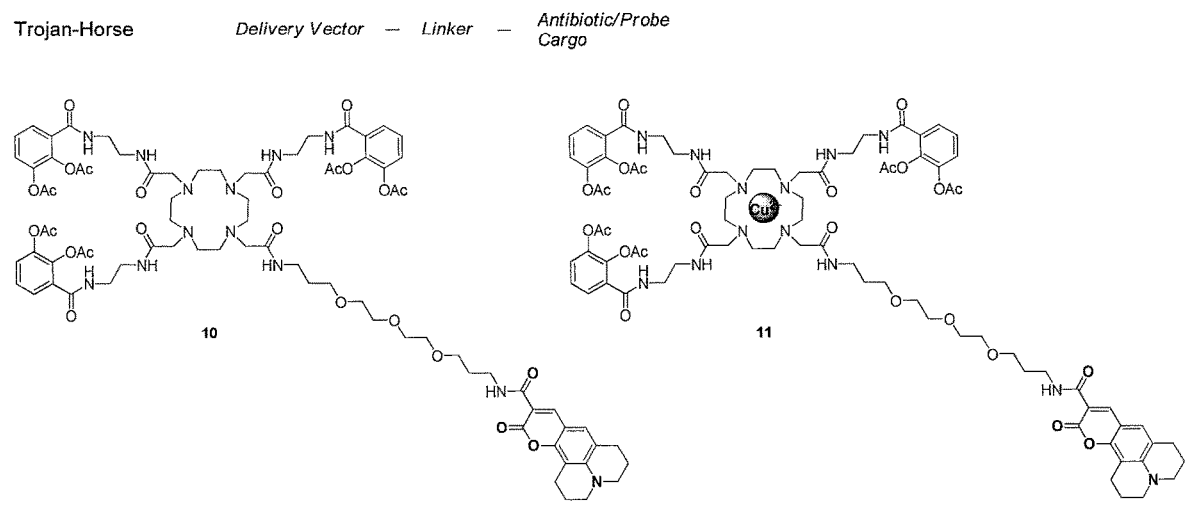
FIG. 3.

Another embodiment is shown in FIG. 3, namely, compound 10 and compound 11. In compound 10, the core moiety together with the siderophore formed by three moieties of B, G is a compound wherein the functional element is 25 coumarin 343. In compound 11, additionally, a copper ion, $Cu^{2+}$, is coordinated in the DOTA core unit.

Figure 6:
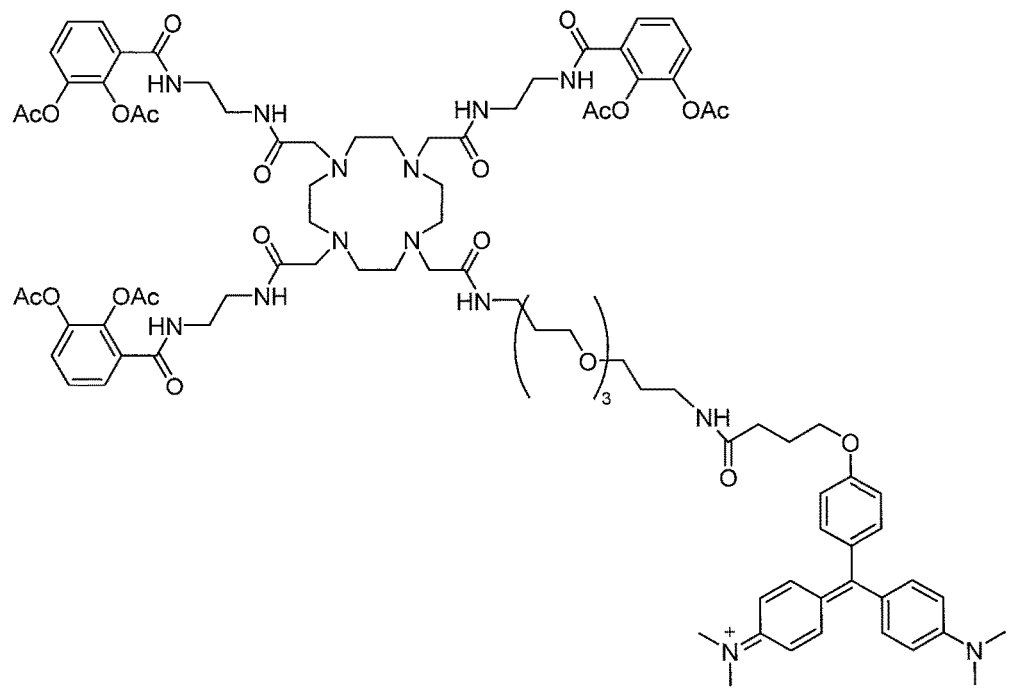
FIG. 6.
Figure 7:
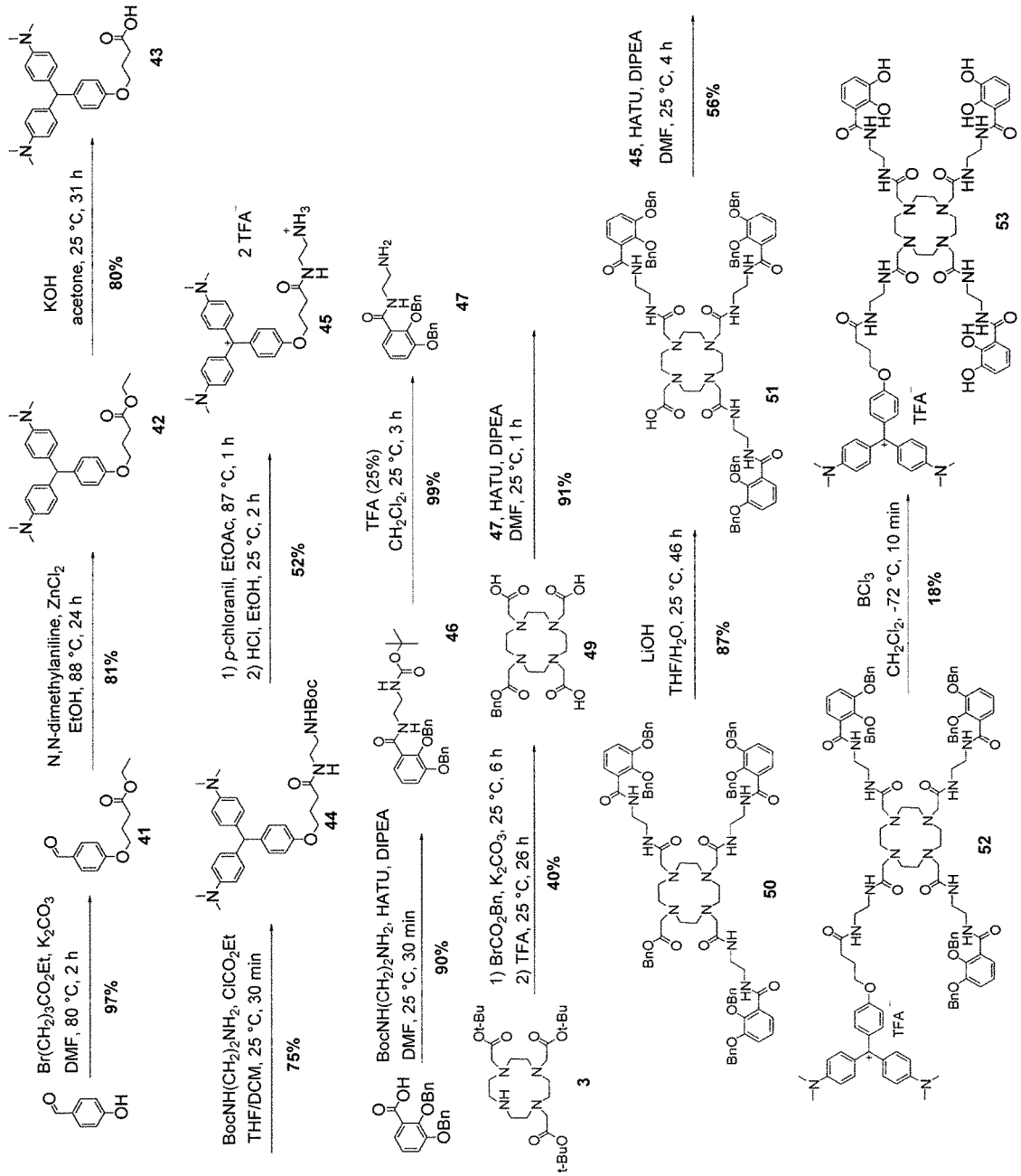
FIG. 7.

A further embodiment is shown in FIG. 6, namely DOTAM-MG.

The compounds according to the present invention are particularly useful as diagnostic as well as therapeutic agents. Hence, in another aspect, the present invention relates to a pharmaceutical composition containing a compound according to the present invention, optionally together with typical excipients, diluents or carrier.

In an embodiment, the compound according to the present invention is for use as an antibiotic.

Moreover, the compound according to the present invention is useful for diagnostic purposes. In particular, for imaging purposes, like optical imaging, molecular imaging and/or chemical imaging.

That is, the compounds are particularly useful for in vivo imaging, in particular, computer tomography (CT) as well as magnet resonance imaging (MRI) based methods. In addition, in case of using radioactive marker molecules, in particular, metal ions being positively charge metal ions, single-photon emission computed tomography (SPECT) or positron emission tomography (PET) may be used allowing morphological imaging accordingly The compounds according to the present invention may allow to differentiate between infection and inflammation, e.g. showing bacterial growth. Since the compounds according to the present invention including the siderophore moiety are transported actively into the pathogen cells, it is possible to image the presence of the pathogen cells in vivo. Suitable compounds allowing direct imaging of bacteria are in progress but are not established yet. Hence, the compounds according to the present invention complement suitable molecules useful in in vivo imaging. In addition, the compounds according to the present invention combing the diagnostic property with a therapeutic property, e.g. when coordinating Cu ions. Copper represents a known bacterial growth inhibiting compound. As demonstrated in the examples, siderophore DOTA compounds according to the present invention containing $Cu^{2+}$ coordinated in the DOTA core demonstrate strong inhibition of bacterial growth in vitro. The DOTA derivative use in the examples where coupled with coumarin 343, a known fluorophore. A weak inhibition of bacterial growth shown even in the absence of copper.

In an embodiment of the present invention, the metal ion M is a positively charged metal ion out of the group Gd, Yb, Mn, Cr, Cu, Fe, Pr, Nd, Sm, Tb, YDy, Ho, Er, Eu, Ga, $^{68}$Ga, $^{64}$Cu, $^{99m}$Tc, $^{177}$Lu, $^{67}$Ga, $^{111}$In, $^{99}$Mo for imaging, in particular, SPEC or PET or MRI. That is, while $Fe^{2+}$ or $Fe^{3+}$ ions are present in the siderophore, the metal ion present in the core unit is the same metal ion or a different metal ion as mentioned above.

In another aspect, the present invention relates to the use of the compound according to the present invention as a vehicle for the transport of a compound of interest into bacteria, yeast, fungi or plants. That is, utilizing the siderophore activity of the compounds according to the present invention and, thus, the active transport thereof into the bacteria, yeast, fungi or plants, it is possible to transport other compounds of interest into the cell. These compounds of interest include the functional element as defined for substituent G including active agent inhibiting the growth of bacteria or killing bacteria or other pathogens accordingly.

By combining the two functionalities of siderophore with the property of chelating metal ions, it is possible to provide theranostic agents allowing therapy and/or diagnosis of pathogens, in particular, bacteria in a subject, typically, a mammal, like a human, and a non-human primate. The subject can be male or female.

The pharmaceutical composition for use in connection with the invention can be formulated as neutral or salt forms. Pharmaceutical acceptable salts include those formed with anions such as those derived from hydrochloric, phosphoric, acetic, oxalic, tartaric acids etc., and those formed with cations, such as those derived from sodium, potassium, ammonium, calcium, ferric hydroxides, isopropyl amine, etc. The pharmaceutical composition is applied in therapeutically or pharmaceutically effective amount which refers to the amount of composition sufficient to adduce a desired biological result. The pharmaceutical composition is administered by known methods. The skilled person can easily determine the suitable way of administration as well as the suitable dosage regiment in order to achieve the desired results accordingly.

These and other embodiments are disclosed and encompassed by the description and examples of the present invention. The present invention will be detailed further by way of examples without limiting the same thereto.

EXAMPLES

Abbreviations arom.=aromatic

Boc=tert-butyloxycarbonyl

DIPEA=diisopropyl-ethyl amine

DMF=dimethylformamide

DCM=dichloromethane

ESI-MS=electrospray ionisation mass spectrometry equiv.=equivalents

HATU=2-(7-Aza-1H-benzotriazole-1-yl)-1,1,3,3-tetramethyluronium hexafluorophosphate.

HPLC=high performance liquid chromatography

LC-MS=liquid chromatography mass spectrometry

NMR=nuclear magnetic resonance

Pmc=2,2,5,7,8-pentamethylchroman-6-sulfonyl

TFA=trifluoro-acetic acid

General Methods

Unless otherwise noted, all reagents were purchased from commercial suppliers and used without further purification. All solvents used were of HPLC grade. Reactions were analyzed LC-MS. Reverse-phase HPLC was performed on a C18 column Sun Fire 50×100 mm, Waters or XBridge™ Prep C18, 5 µm (10×100 mm; Waters). LC/MS data were acquired using the Waters or HP-Agilent 1100 MSD system. NMR-data were recorded on a Bruker DRX-500 system in $d_6$-DMSO or $CDCl_3$. Fluorescence assays was measured with a Tecan SAFIRE II spectrometer.

The prepared compounds were in general characterized by spectroscopic data and chromatographic data, in particular mass spectra (MS) and/or nuclear magnetic resonance (NMR) spectra. In the NMR characterization, the chemical shift δ (in ppm), the number of hydrogen atoms (H), the coupling constant J (in Hz) and the multiplicity (s: singlet, d: doublet, dd: double doublet, t: triplet, m: multiplet; br: broad) of the peaks are given. In the MS characterization, the mass number (m/e) of the peak of the molecular ion (M) or of a related ion such as the ion (M+1), i.e. the protonated molecular ion (M+H), or the ion (M−1), which was formed depending on the ionization method used, is given. Generally, the ionization method was electrospray ionization (ES+ or ES−).

Synthesis of Key Intermediate for Siderophore Conjugates

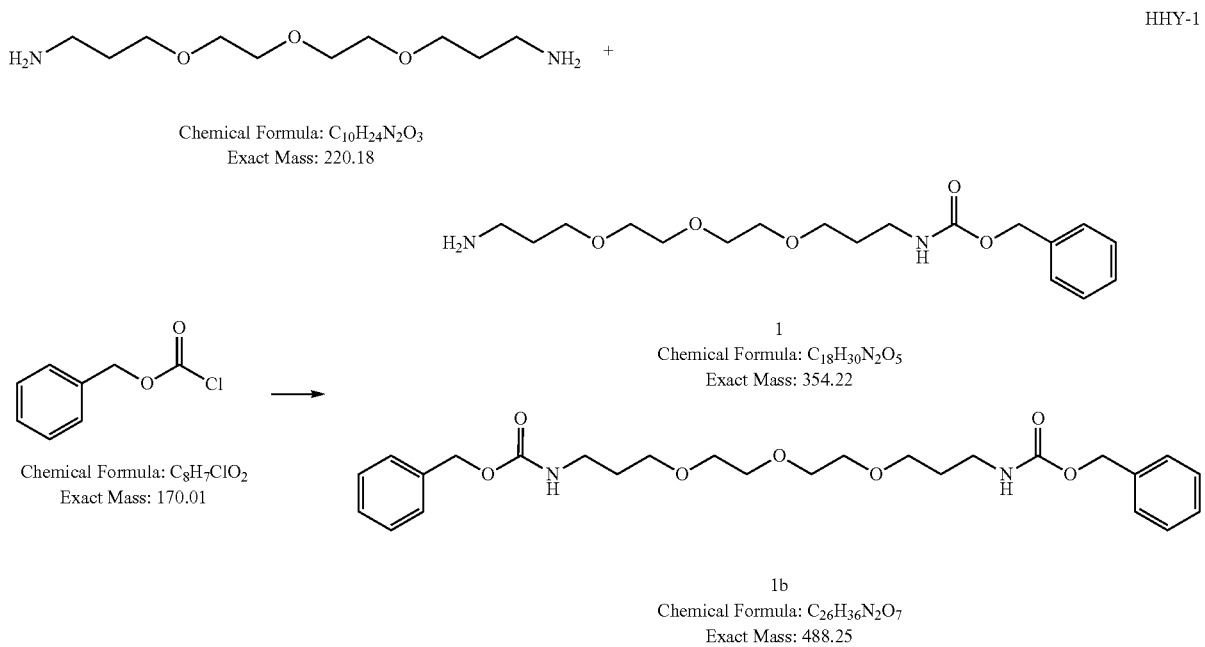

HHY-1

1
Chemical Formula: $C_{18}H_{30}N_2O_5$
Exact Mass: 354.22

1b
Chemical Formula: $C_{26}H_{36}N_2O_7$
Exact Mass: 488.25

Into a flask were added THF (200 mL, 0.1 M), 4,7,10-trioxa-1,13-tridecanediamine (22.0 mL, 100 mmol, 5 equiv), triethylamine (2.77 mL, 20.0 mmol, 1.0 equiv), and MeOH (70 mL, 0.3 M). The flask was fitted with an addition funnel, maintained under a nitrogen atmosphere, and cooled in an ice bath (0° C.). Benzyl chloroformate (2.84 mL, 20.0 mmol, 1 equiv) was dissolved in THF (100 mL, 0.2 M) and added dropwise (over 45 min) to the reaction mixture. The reaction was allowed to warm to ambient temperature and stirred (30 min). Volatiles were removed under reduced pressure. The crude mixture was diluted with brine (200 mL) and sodium carbonate (10% aqueous, 40 mL), extracted with ether (150+2×100 mL), washed with brine (100 mL), and dried with sodium sulfate. Volatiles were removed under reduced pressure, to yield a mixture (approximately 4:1) of monocarbamate 1 and dicarbonate 1b, which was used directly for the next step. Product analysis is consistent with reported data. Crude monocarbamate 1: $^1$H NMR (CDCl$_3$, 500 MHz) δ 7.36-7.28 (m 5H, Bn), 5.58-5.52 (brs, 1H, NHZ), 5.09 (s, 2H, Bn), 3.65-3.45 (m, 12H, 6×CH$_2$—O), 3.33-3.27 (m, 2H, CH$_2$—NHZ), 2.77 (t, J=6.8 Hz, 2H, CH$_2$—NH$_2$), 1.80-1.66 (m, 4H, 2×C—CH$_2$—C).[2]

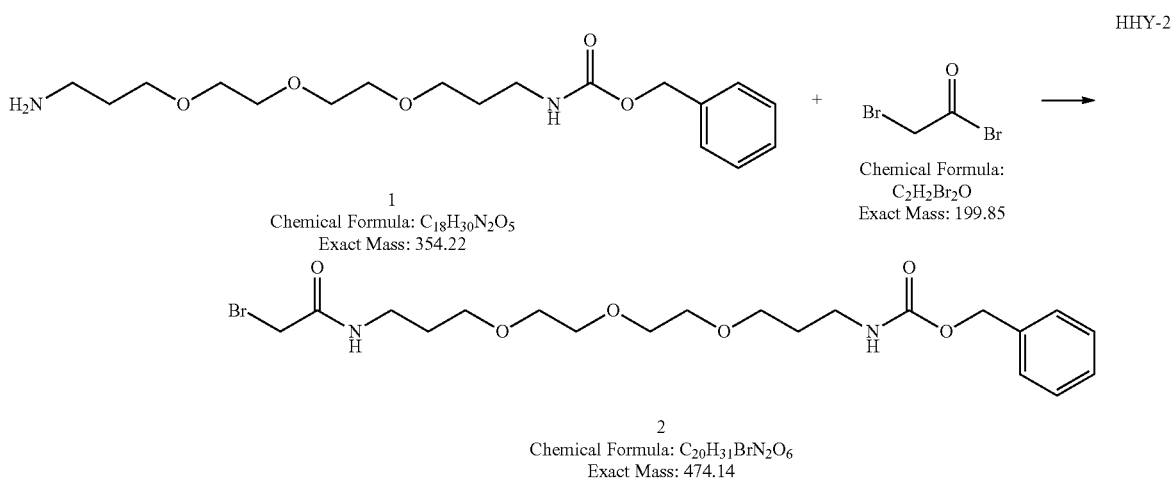

HHY-2

1
Chemical Formula: $C_{18}H_{30}N_2O_5$
Exact Mass: 354.22

Chemical Formula: $C_2H_2Br_2O$
Exact Mass: 199.85

2
Chemical Formula: $C_{20}H_{31}BrN_2O_6$
Exact Mass: 474.14

Bromoacetyl bromide (287 µl, 3.3 mmol) was added dropwise to a solution of compound 1 (1062 mg, 3 mmol) and TEA (837 µl, 6 mmol) in 12 ml dichloromethane at 0° C. The reaction mixture was allowed to stir for 2 hours and the temperature gradually rose to room temperature. The solvents were evaporated followed by aqueous work up and extraction with ethyl acetate. The organic layer was washed with 10% citric acid, water and saturated sodium bicarbonate and brine and dried over anhydrous sodium sulfate, giving crude compound 2, which was used immediately and directly for the next step. ESI-MS: $C_{20}H_{31}BrN_2O_6$ m/z=475.2 [M+H$^+$].

HHY-3

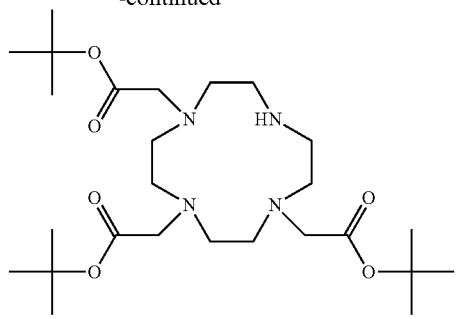

3
Molecular Weight: 514.71
Molecular Formula=$C_{26}H_{50}N_4O_6$

To a suspension of cyclen (5.00 g, 29 mmol) and sodium acetate (7.86 g, 96 mmol) in DMA (60 mL) at −20° C. was added a solution of t-butyl bromoacetate (18.7 g, 14.1 mL, 96 mmol) in DMA (20 mL) dropwise over a period of 0.5 hour. The temperature was maintained at −20° C. during the addition, after which the reaction mixture was allowed to come to room temperature. After 24 hours of vigorous stirring, the reaction mixture was poured into water (300 mL) to give a clear solution. Solid KHCO$_3$ (15 g, 150 mmol) was added portion wise, and compound 2 precipitated as a white solid. The precipitate was collected by filtration and dissolved in CHCl$_3$ (250 mL). The solution was washed with water (100 mL), dried (MgSO$_4$), filtered and concentrated to about 20-30 mL. Ether (250 mL) was added, after which compound 3 crystallized as a white fluffy solid. Yield: 12.5 g (73%). ESI-MS found: [M+H]$^+$=515.5.[3]

HHY-4

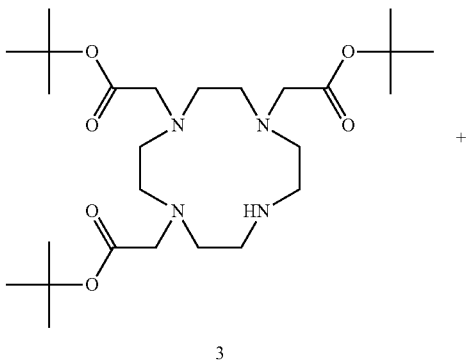

3
Chemical Formula: $C_{26}H_{50}N_4O_6$
Exact Mass: 514.37

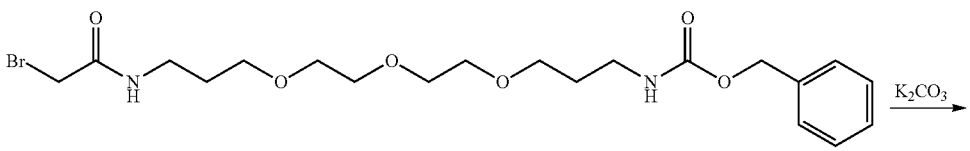

2
Chemical Formula: $C_{20}H_{31}BrN_2O_6$
Exact Mass: 474.14

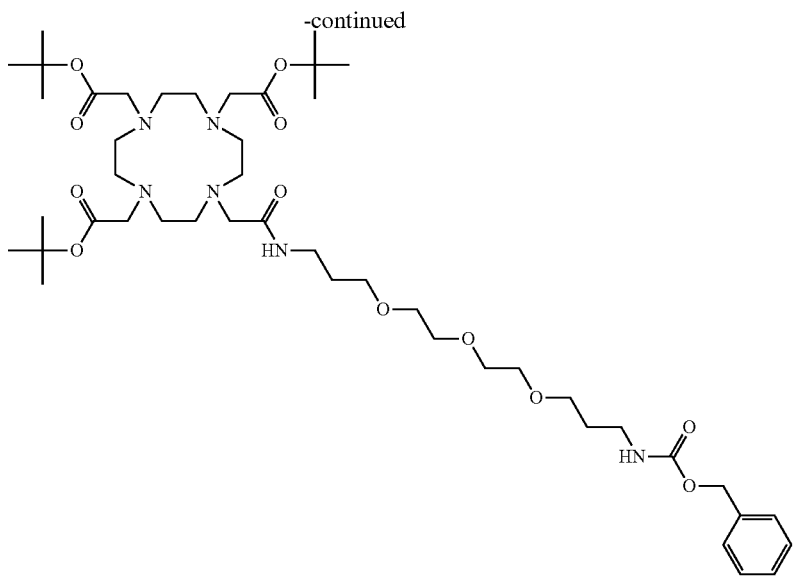

4
Chemical Formula: C_{46}H_{80}N_6O_{12}
Exact Mass: 908.58

To a stirred solution of 1 equiv. HHY-3 (925 mg, 1.8 mmol) and 4 equiv. K$_2$CO$_3$ (994 mg, 7.2 mmol) in CNCH$_3$ (50 mL) was added 1.25 equiv. HHY-2 (1067 mg, 2.25 mmol) in CNCH$_3$ (20 mL) within 10 min. Stirring was continued for overnight under argon at room temperature. The precipitate was filtered and the filtrate concentrated in vacuo. The resulting oil was purified by RP-HPLC (10% to 90% MeCN) or Flash silica gel column chromatography (eluent: DCM:MeOH=9:1-4:1) yielding 4 (0.644 g, 0.7 mmol, 39%) as a white solid. ESI-MS found: [M+H]$^+$=909.5

HHY-5

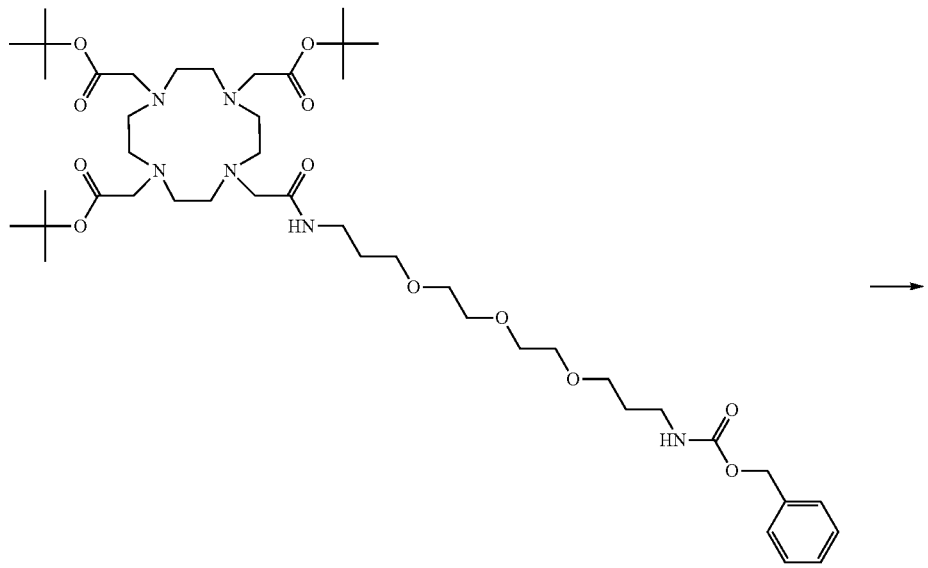

4
Chemical Formula: C_{46}H_{80}N_6O_{12}
Exact Mass: 908.58

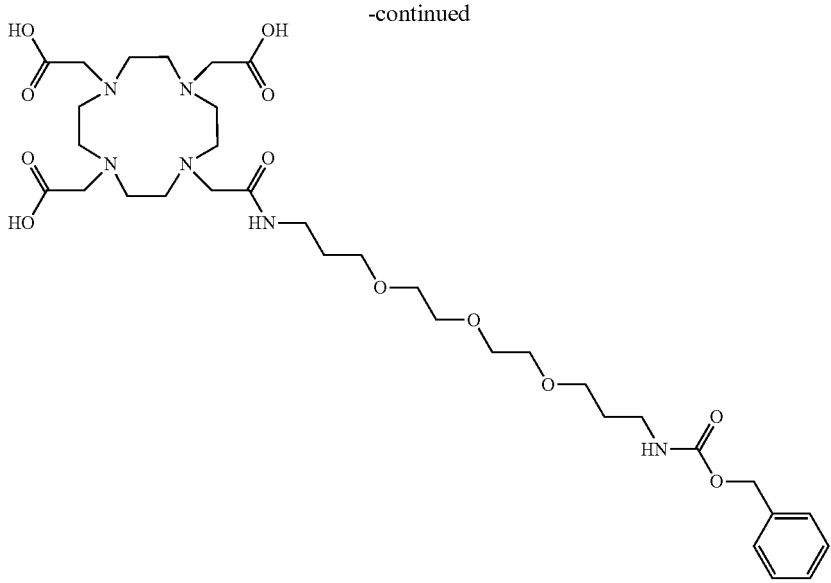

5
Chemical Formula: C$_{34}$H$_{56}$N$_6$O$_{12}$
Exact Mass: 740.40

For removal of the tBu-group, compound HHY-4 (91 mg, 0.1 mmol) was dissolved in 3 ml 95% TFA/H$_2$O and the reaction mixture was stirred for 2 hours under argon at room temperature. The reaction was monitored by LC-MS. After the reaction was complete, the solvent was 3 times co-evaporated with toluene. The crude product was used without further purification in the next step. ESI-MS found: [M+H]$^+$=741.8.

HHY-14

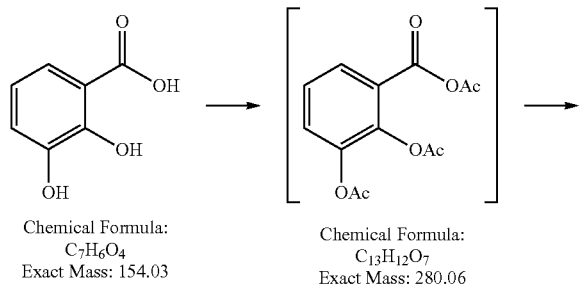

2,3-Dihydroxybenzoic acid was reacted with 3 eq. of acetic anhydride in the presence of Et$_3$N and catalytic amount of dimethylaminopyridine (DMAP) in THF to afford diacetoxy benzoic acids.[4] The mixture was stirred overnight and the solution concentrated in vacuo to remove the THF. The residue was dissolved in chloroform (100 ml) and washed with 1N HCl then water (100 ml). The organic phase was dried under reduced pressure to give the crude product. Yield: 98% colourless solid. Mp 156-159° C. $^1$H NMR (CDCl$_3$) δ 7.92 (dd, J=8.0, 1.7 Hz, 1H), 7.37 (dd, J=8.0, 1.7 Hz, 1H), 7.28 (t, J=8.0 Hz, 1H), 2.27 (s, 3H), 2.25 (s, 3H). $^{13}$C NMR (CDCl$_3$) δ=186.6 (C), 168.9 (C), 168.2 (C), 143.6 (C), 143.1 (C), 129.6 (CH), 128.8 (CH), 126.2 (C), 123.9 (C), 20.7 (CH$_3$). EI-MS: m/z=238 [M]$^+$. IR (cm$^{-1}$)=1772, 1692, 1585, 1470, 1423, 1371, 1306, 1205, 1159, 1020, 911, 857, 755, 695. Calcd. for C$_{11}$H$_{10}$O$_6$: C, 55.47; H, 4.23. Found: C, 55.16; H, 3.97.[5]

HHY-15

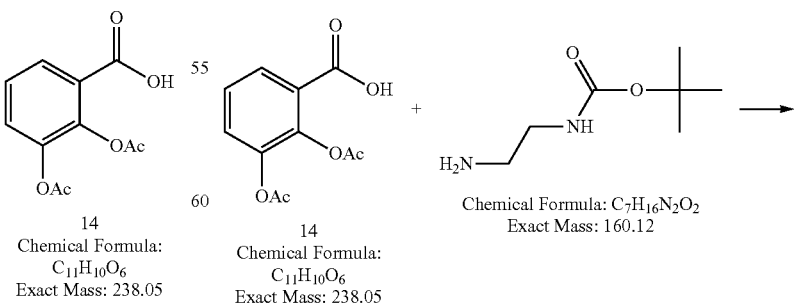

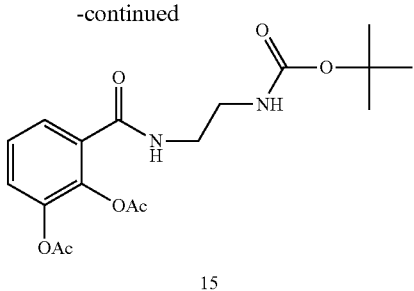

15
Chemical Formula: $C_{18}H_{24}N_2O_7$
Exact Mass: 380.16

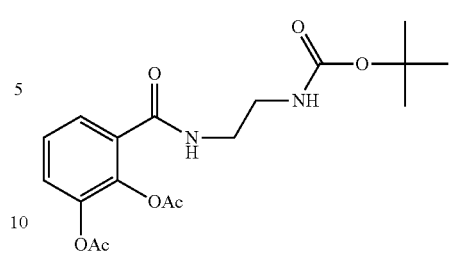

15
Chemical Formula: $C_{18}H_{24}N_2O_7$
Exact Mass: 380.16

1 equiv. HHY-14 (1190 mg, 5 mmol), 1.1 equiv. HATU (2090 mg, 5.5 mmol) and 2 equiv. DIPEA (1.74 mL, 10 mmol) were dissolved in 25 mL DMF. After 10 min, 1 equiv. N-Boc-ethylenediamine (2.37 mL, 0.15 mmol) was added to the reaction mixture and stirred 30 min. under argon at room temperature. 50 mL ethyl acetate was added into the reaction solvent followed by aqueous work up. The organic layer was washed 3 times with 1N HCl and brine then dried over anhydrous sodium sulfate, giving crude compound 15, which was purified by Flash silica gel column chromatography (eluent: PE:EtOAc=1:1-1:3) to give HHY-15 (580 mg, 31%) as a white powder. ESI-MS found: $[M+Na]^+=403.3$.

HHY-16

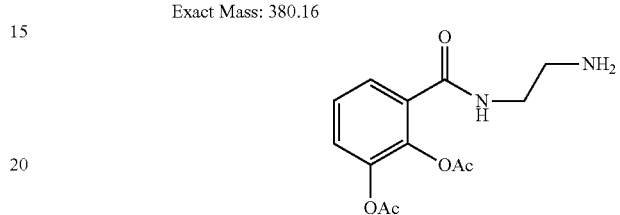

16
Chemical Formula: $C_{13}H_{16}N_2O_5$
Exact Mass: 280.11

For removal of the Boc protection group, compound HHY-15 (80 mg, 0.21 mmol) was dissolved in 3 ml 50% TFA/CH$_2$Cl$_2$ and the reaction mixture was stirred for 10 min under argon at room temperature. The reaction was monitored by LC-MS. After the reaction was complete, the solvent was 3 times co-evaporated with toluene. The crude product was used without further purification in the next step. ESI-MS found: $[M+H]^+=281.2$.

HHY-17

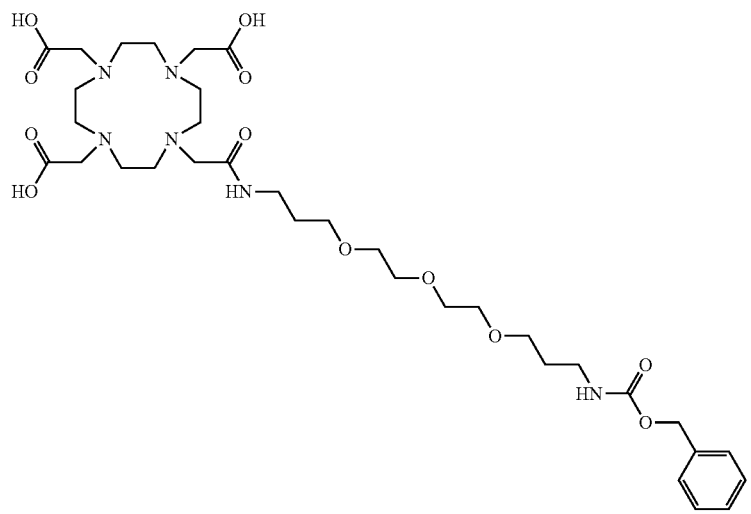

5
Chemical Formula: $C_{34}H_{56}N_6O_{12}$
Exact Mass: 740.40

+ 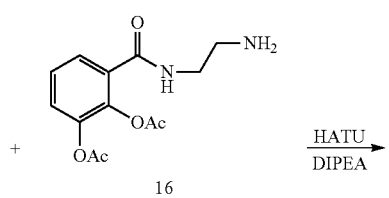

16
Chemical Formula: $C_{13}H_{16}N_2O_5$
Exact Mass: 280.11

$\xrightarrow{\text{HATU}}{\text{DIPEA}}$

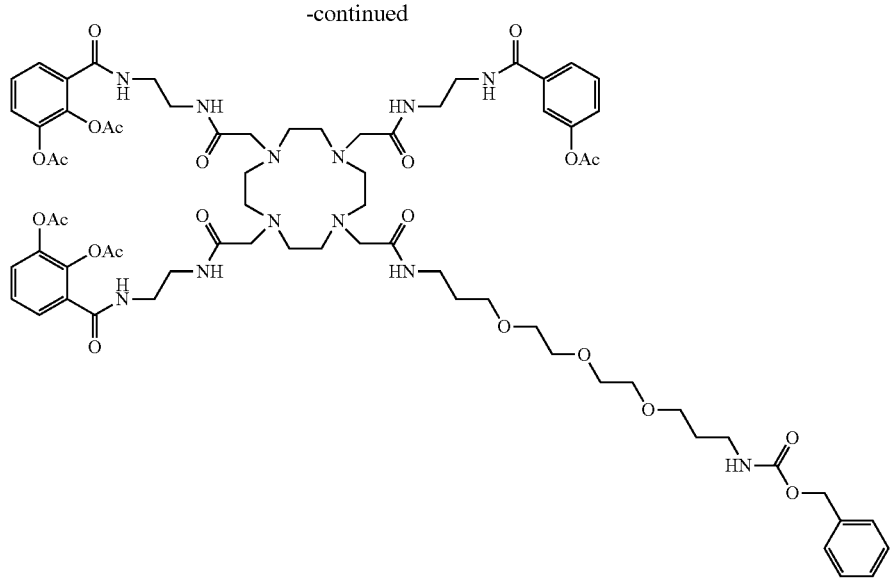

17/8
Chemical Formula: $C_{73}H_{98}N_{12}O_{24}$
Exact Mass: 1526.68

1 equiv. HHY-5 (52 mg, 0.07 mmol), 3 equiv. HATU (80 mg, 0.21 mmol) and 3.3 equiv. DIPEA (40 μl, 0.23 mmol) were dissolved in 3 ml DMF/$CH_2Cl_2$ (1:1). After 10 min, the reaction mixture was added into 3 equiv. HHY-16 (66 mg, 0.21 mmol) and stirred 30 min. under argon at room temperature. The solution concentrated in vacuo to remove the $CH_2Cl_2$ then directly and immediately purified by HPLC to give HHY-17 (40 mg, 37%) as a white powder. HHY-17 could be hydrolysed in weak base solution. This compound 18 is obtained when the Ac group is hydrolysated and H is present. ESI-MS found: $[M+2H]^{2+}=846.7$.

HHY-9

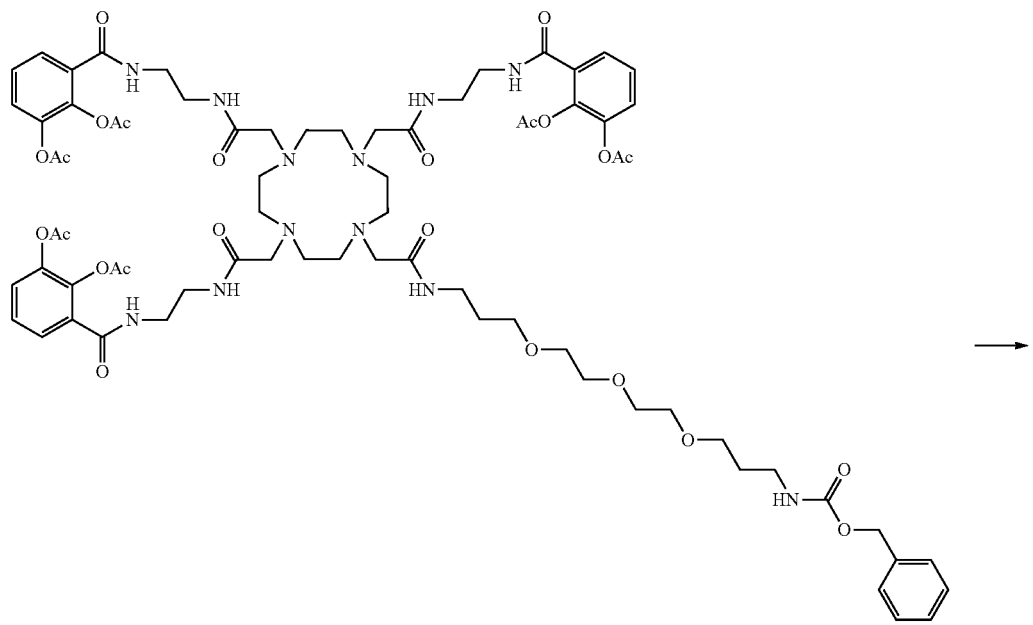

17/8
Chemical Formula: $C_{73}H_{98}N_{12}O_{24}$
Exact Mass: 1526.68

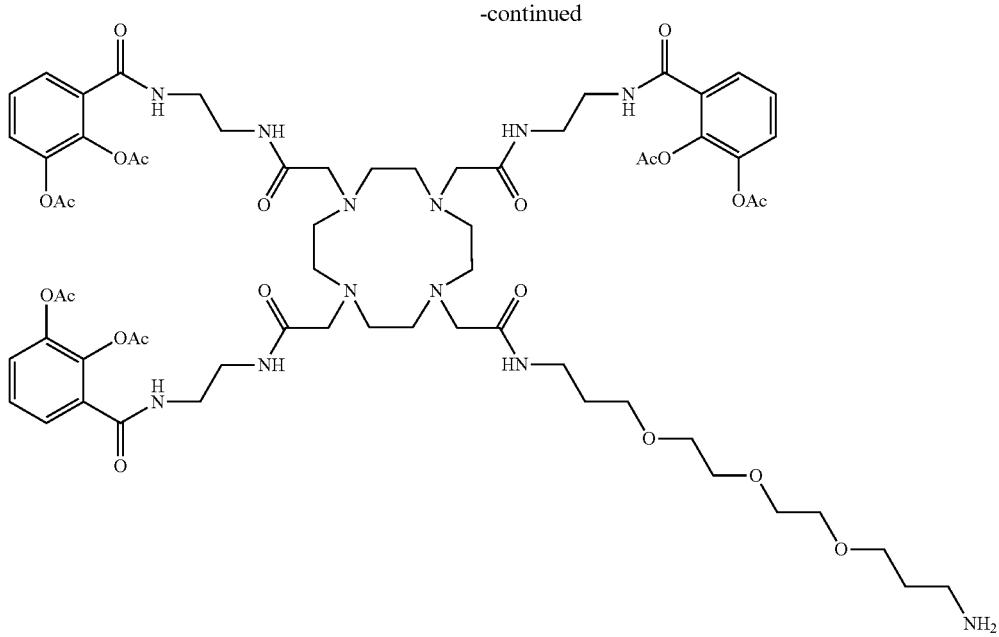
9
Chemical Formula: $C_{65}H_{92}N_{12}O_{22}$
Exact Mass: 1392.64
HHY-17 (31 mg, 20 μmol) was hydrogenolyzed over 10% Pd on carbon (4 mg) in MeOH (5 mL) for 12 h. The Pd/C was removed by filtration and the MeOH removed by evaporation. Compounds were analyzed by LC MS and used without further purification. ESI-MS found: $[M+2H]^{2+}=698.0$.
HYY-10
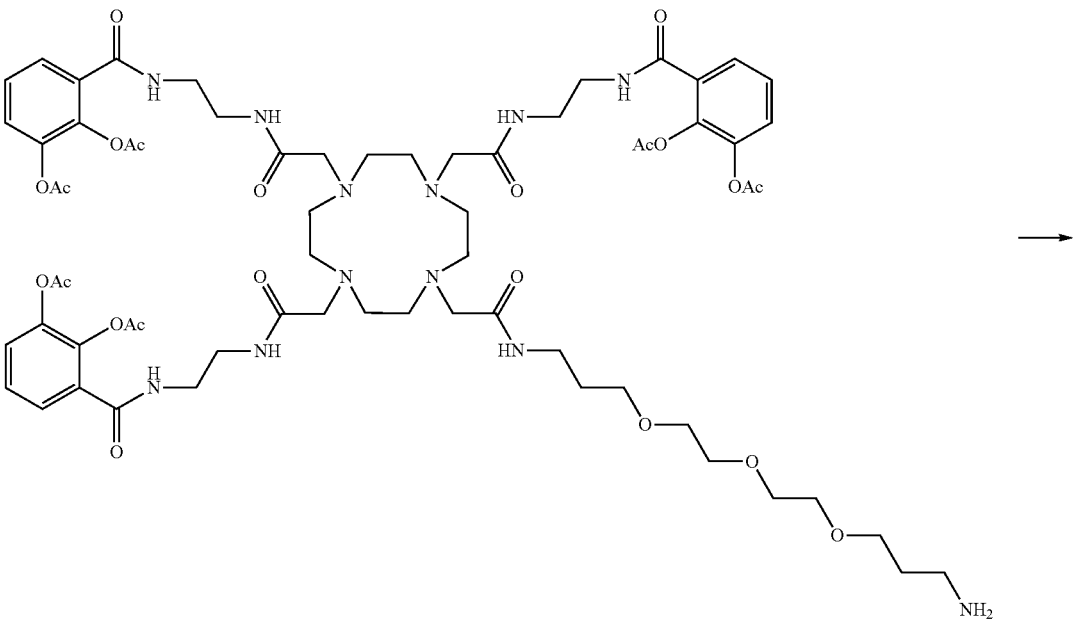
9
Chemical Formula: $C_{65}H_{92}N_{12}O_{22}$
Exact Mass: 1392.64

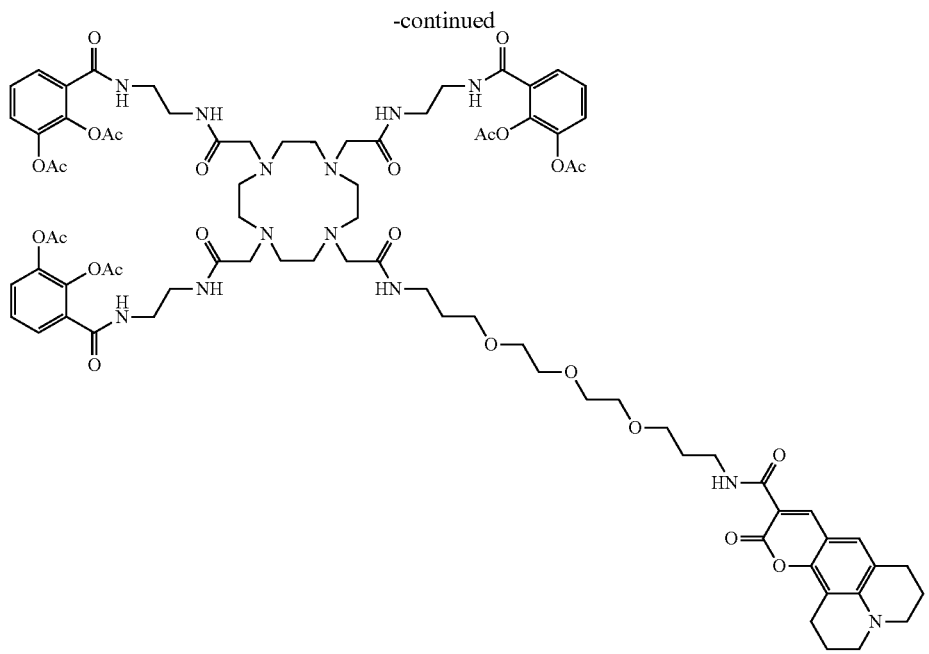

Chemical Formula: $C_{81}H_{105}N_{13}O_{25}$
Exact Mass: 1659.73

1 equiv. Coumarin 343 (5.7 mg 20 μmol), 1.1 equiv. HATU and 1.5 equiv. DIPEA were dissolved in 3 ml DMF/$CH_2Cl_2$ (1:1) After 10 min, the reaction mixture was added into 1 equiv. HHY-9 (29 mg, 20 μmol) and stirred 30 min. under argon at room temperature. The solution concentrated in vacuo to remove the $CH_2Cl_2$ then purified by HPLC to give HHY-10 (17 mg, 52%) as a yellow green powder. ESI-MS found: $[M+2H]^{2+}=831.0$.

HHY-31

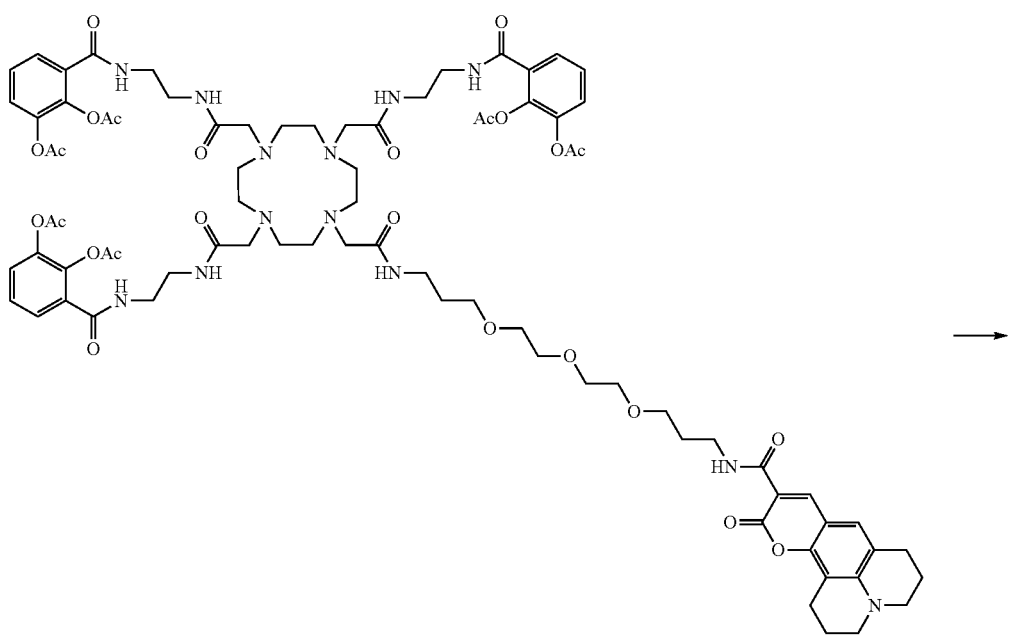

Chemical Formula: $C_{81}H_{105}N_{13}O_{25}$
Exact Mass: 1659.73

-continued
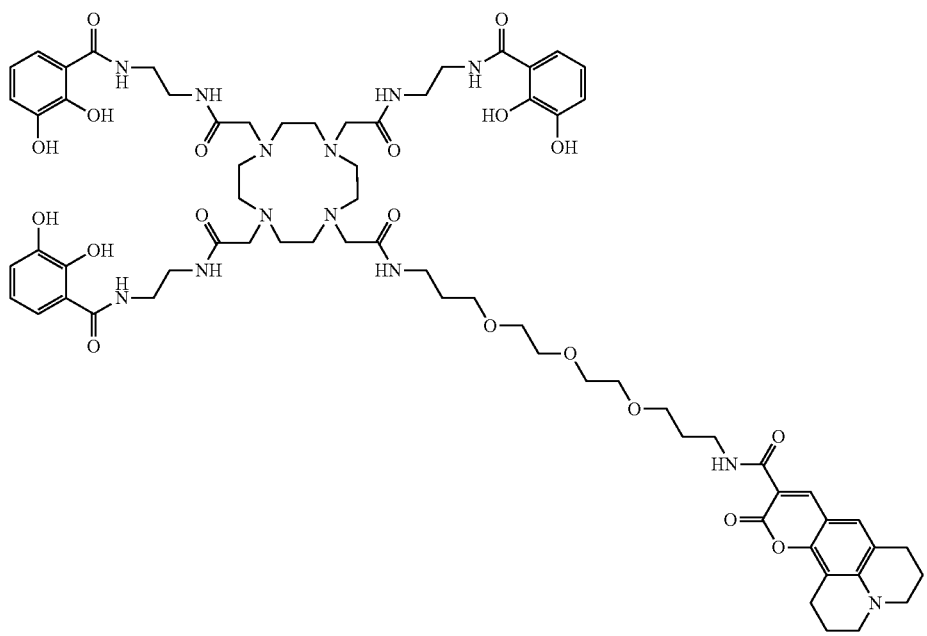
31
Chemical Formula: C$_{69}$H$_{93}$N$_{13}$O$_{19}$
Exact Mass: 1407.67
HYY-11
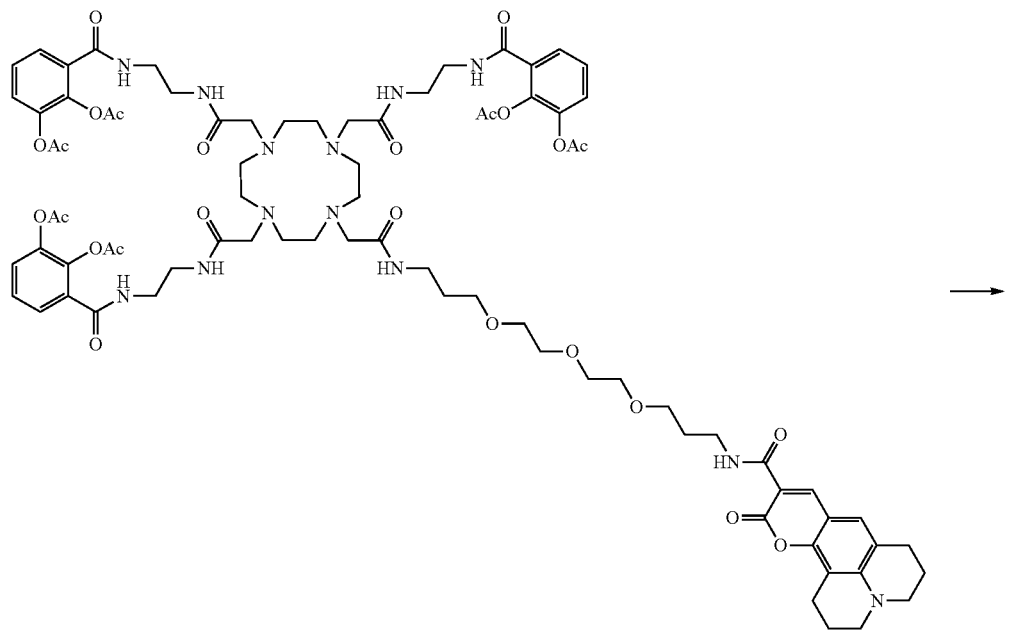
10
Chemical Formula: C$_{81}$H$_{105}$N$_{13}$O$_{25}$
Exact Mass: 1659.73

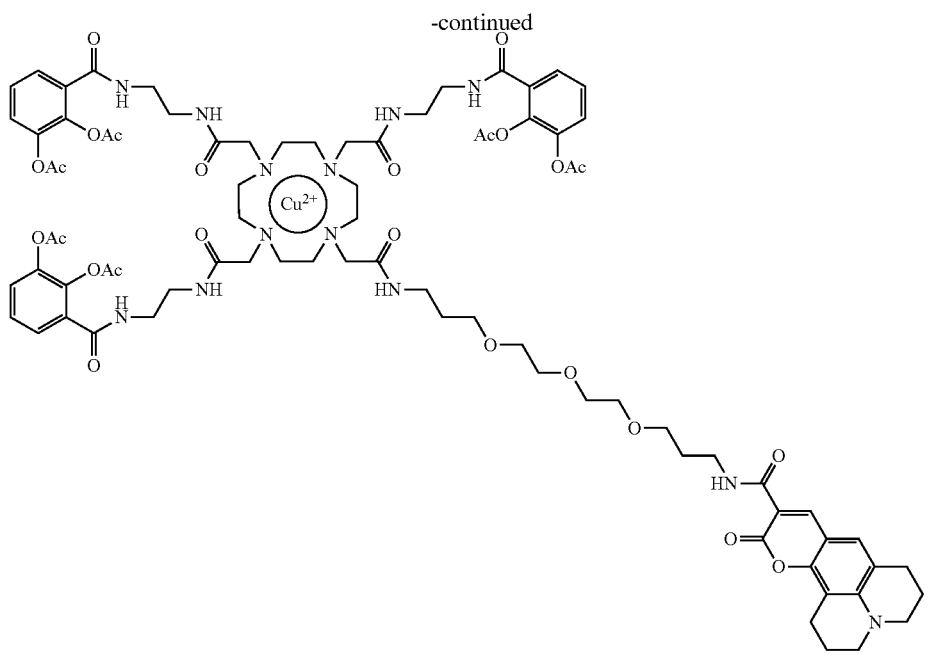
11
Chemical Formula: $C_{81}H_{105}N_{13}O_{25}{}^{2+}$
Exact Mass: 1722.66
HHY-10 (10 mg, 6 μmol) was dissolved in 80% methanol (1 mL) and a solution of 1 equiv. Cu(NO$_3$)$_2$ (1.2 mg, 6 μmol) in methanol (6 μL) was added. The reaction mixture stirred overnight under argon at room temperature then purified by HPLC to give HHY-11 (9 mg, 87%) as a green powder. ESI-MS found: [M]$^{2+}$=861.84.
HYY-30
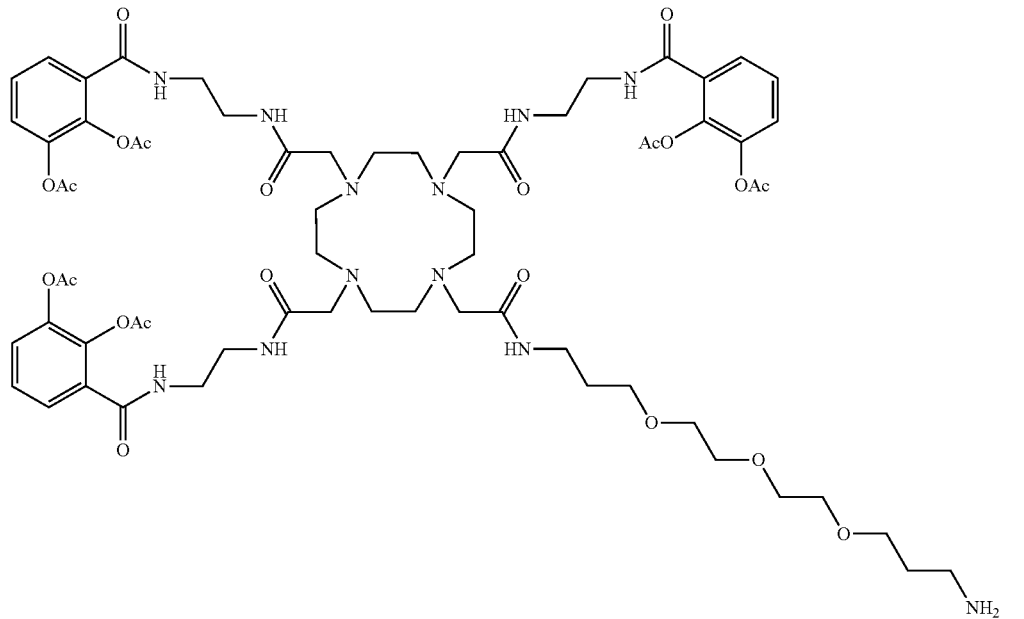
9

-continued
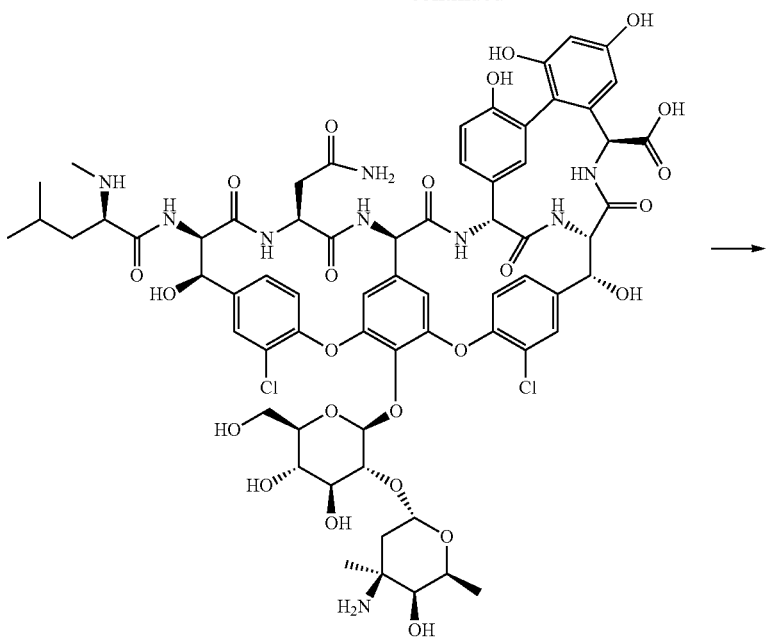
Vancomycin
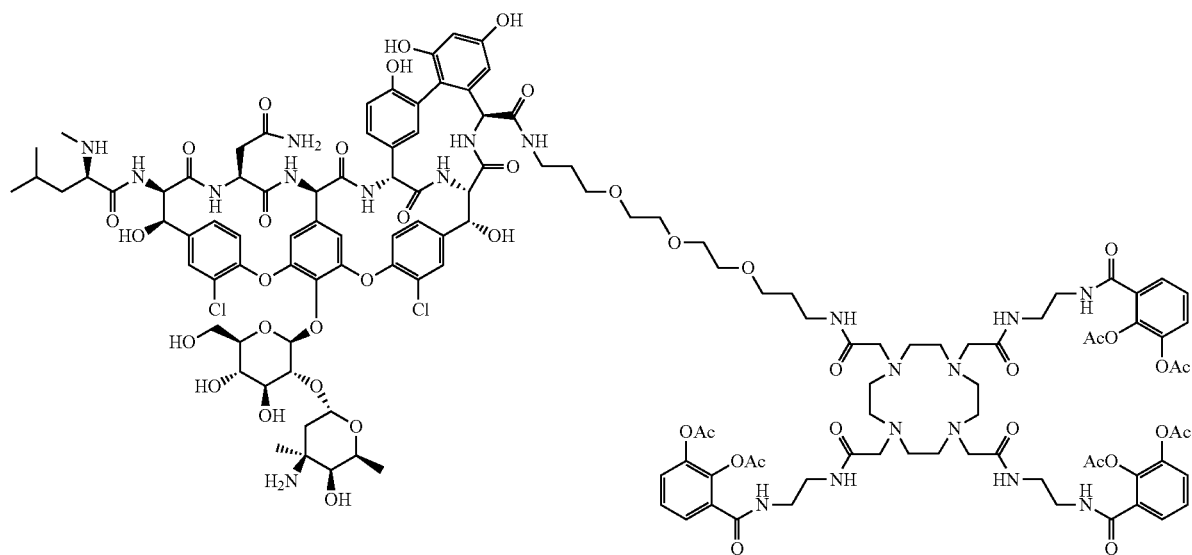
30
Chemical Formula: $C_{131}H_{165}Cl_2N_{21}O_{45}$
Exact Mass: 2822,06

1 equiv. vancomycin (15 mg 10 μmol), 1.1 equiv. HBTU and 1.5 equiv. DIPEA were dissolved in 3 ml DMF/CH$_2$Cl$_2$ (1:1) After 10 min, the reaction mixture was added into 2 equiv. HHY-9 (29 mg, 20 μmol) and stirred 30 min. under argon at room temperature. The solution concentrated in vacuo to remove the CH$_2$Cl$_2$ then purified by HPLC to give HHY-30 (3 mg, 11%) as a white powder. MALDI-TOF found: [M+H]$^{2+}$=2823.745.

Synthesis of Malachite-Green Conjugated DOTA-Based Siderophore Containing Compound According to the Present Invention (See Scheme 7).

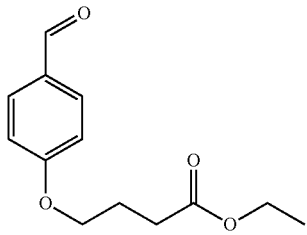

41

Compound 41

To a stirred suspension of 4-hydroxybenzaldehyde (1.00 g, 8.19 mmol) and K$_2$CO$_3$ (3.40 g, 24.60 mmol) in DMF (30 mL) under N$_2$ atmosphere in a three-neck flask, was added dropwise ethyl-4-bromobutanoate (1.38 mL, 9.64 mmol). The white suspension was stirred at 80° C. for 2 h under N$_2$ atmosphere. The reaction was monitored by TLC (silica gel, Hexane:EtOAc/8:2). The reaction mixture was concentrated under reduced pressure. The resulting oil residue was dissolved in Et$_2$O (30 mL) and washed three times with brine. The organic layer was dried over anhydrous MgSO$_4$, and concentrated under reduced pressure to yield a yellow colored oil (2.15 g). The crude material was purified by silica gel column chromatography (m$_{SiO2}$=40 g, gradient from Hexane:EtOAc/9:1 to Hexane:EtOAc/8:2) to yield a colorless semi-solid (1.84 g, 97%). $^1$H NMR (500 MHz, CDCl$_3$). δ 9.88 (s, 1H, CHO), 7.83 (d, 2H, J=8.8 Hz, ArH$_{ortho}$), 6.99 (d, 2H, J=8.8 Hz, ArH$_{meta}$), 4.15 (q, 2H, J=7.1 Hz, COOCH$_2$), 4.11 (t, 2H, J=6.1 Hz, OCH$_2$), 2.52 (t, 2H, J=7.2 Hz, CH$_2$COO), 2.15 (tt, 2H, J=7.1 Hz, J=6.2 Hz, CH$_2$CH$_2$CH$_2$), 1.26 ppm (t, 3H, J=7.1 Hz, CH$_2$CH$_3$). ESI-MS: C$_{13}$H$_{16}$O$_4$ m/z=237.04 [M+H$^+$]$^+$. The analyzed data showed accordance to the previous published ones except for the signal at 4.11 ppm showing a triplet[7].

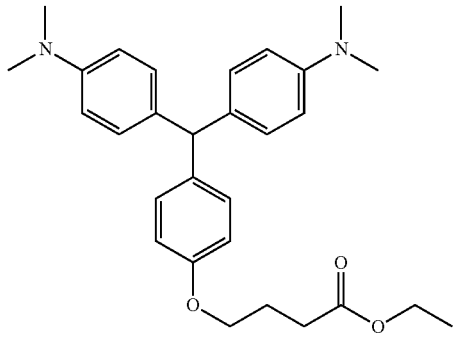

42

Compound 42

To a solution of ethyl 4-(4-formylphenoxy)butanoate 41 (1.74 g, 7.36 mmol) in anhydrous EtOH (30 mL) were added dimethylaniline (1.9 mL, 14.99 mmol), 4 Å molecular sieves (1.8 g) and anhydrous ZnCl$_2$ (2.01 g, 14.75 mmol) under Ar atmosphere. The reaction mixture was refluxed for 24 h. The blue solution was monitored by TLC (Hexane/EtOAc: 6/4). After completion of the starting material, the reaction mixture was filtered through paper and concentrated to yield a blue colored oil. The filtrate was redissolved in EtOAc and water. The aqueous layer was extracted by EtOAc (3×50 mL) and the combined organic layers were washed with brine (3×50 mL), dried over MgSO$_4$, filtered through paper and concentrated to yield a blue colored oil (4.00 g). The crude material was triturated in EtOAc and filtered to yield a dark blue colored solid (0.35 g). The mother liquor was concentrated to yield a blue colored oil (3.40 g). The crude oil was purified by flash column chromatography (m$_{SiO2}$=120 g, gradient from PE:EtOAc/9:1 to PE:EtOAc/6:4) to yield a light blue colored oil (2.75 g, 81%). $^1$H NMR (500 MHz, CDCl$_3$). δ 7.01 (d, 2H, J=8.7 Hz, Ar—H), 6.98 (d, 4H, J=8.2 Hz, Ar—H), 6.82-6.60 (d+bs, 6H, J=8.7 Hz, Ar—H), 5.33 (s, 1H), 4.13 (q, 2H, J=7.1 Hz, COOCH$_2$), 4.13 (t, 2H, J=6.1 Hz, OCH$_2$), 2.92 (s, 12H), 2.50 (t, 2H, J=7.3 Hz, CH$_2$COO), 2.08 ppm (tt, 2H, J=7.1 Hz, J=6.2 Hz, CH$_2$CH$_2$CH$_2$). ESI-MS: C$_{29}$H$_{37}$N$_2$O$_3$$^+$ m/z=461.5 [M+H$^+$]$^+$. The analyzed data showed accordance to the previous published ones[8].

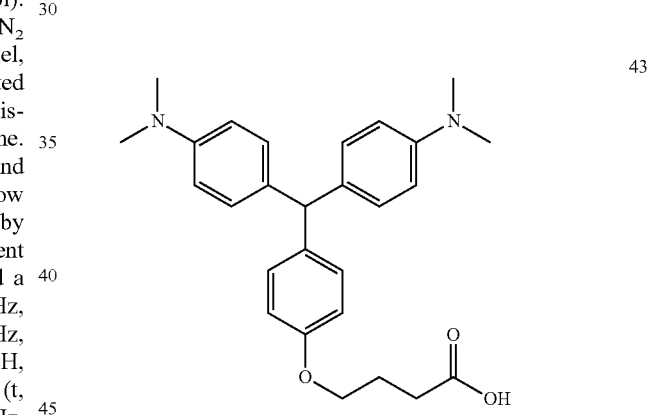

43

Compound 43

To a blue solution of compound 42 (2.23 g, 4.84 mmol) in acetone (40 mL) was added dropwise a KOH solution (423 mg in 5 mL H$_2$O, 7.54 mmol). The yellow solution was stirred at 25° C. for 31 h. The reaction was monitored by LC-MS. HCl (3 M, 6 mL) was added to the reaction mixture. The mixture was concentrated and rediluted in CH$_2$Cl$_2$ and H$_2$O. The organic layer was washed with brine (3×50 mL), dried over MgSO$_4$, filtered through paper and concentrated to yield a green colored oil (2.00 g). The crude material (1.30 g) was diluted in ACN (20 mL) until observing precipitation. The suspension was centrifuged (1800 RPM, 5 min) to separate phases and yield a white solid (0.22 g) and a dark blue oil (1.08 g, 80%). ESI-MS: C$_{27}$H$_{33}$N$_2$O$_3$$^+$ m/z=433.5 [M+H$^+$]$^+$. $^1$H NMR from a 100 mg scale reaction of compound 2 (500 MHz, CDCl$_3$). δ 7.04-6.95 (m, 6H, Ar—H), 6.82-6.70 (m, 6H, Ar—H), 5.33 (s, 1H), 3.98 (t, 2H, J=6.1 Hz, OCH$_2$), 2.92 (s, 12H), 2.56 (t, 2H, J=7.3 Hz, CH$_2$COO), 2.08 ppm (tt, 2H, J=7.0 Hz, J=6.3 Hz, CH$_2$CH$_2$CH$_2$). The analyzed data showed accordance to the previous published ones.[8]

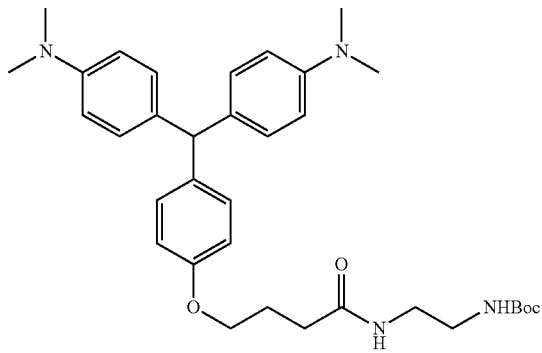

Compound 44

To a dark blue solution of compound 43 (10.0 mg, 23 µmol) in THF:CH$_2$Cl$_2$ (0.25:0.25 mL) were successively added Et$_3$N (3.5 µL, 25 µmol) and ethylchloroformate (2.4 µL, 25 µmol). The reaction mixture was stirred for 30 min and conversion of 3 was monitored by TLC (EtOAc). N-Boc-ethylenediamine solution (3.7 µL, 23 µmol) in THF/CH$_2$Cl$_2$ (0.25/0.25 mL) was added to the reaction mixture and stirred for 30 min at 25° C. The light blue solution was concentrated, rediltuted in EtOAc (10 mL) and a NaHCO$_3$ solution (0.1 M, 20 mL). The aqueous layer was extracted with EtOAc (3×10 mL) and the combined organic layers were washed with brine (3×10 mL). The organic layer was dried over MgSO$_4$, filtered through paper and concentrated to yield a green colored oil (15 mg). The crude material was diluted in CH$_2$Cl$_2$, and purified by flash column chromatography (m$_{SiO2}$=3.0 g, CH$_2$Cl$_2$:MeOH/8:2) to yield a blue colored oil (10.0 mg, 75%). A bigger scale of this reaction (0.27 g of 3) led to a slightly diminished yield (0.19 g, 53%). $^1$H NMR (500 MHz, CD$_3$OD). δ 6.96 (d, 2H, J=8.7 Hz, Ar—H), 6.90 (d, 4H, J=8.7 Hz, Ar—H), 6.79 (d, 2H, J=8.7 Hz, Ar—H), 6.70 (d, 4H, J=8.8 Hz, Ar—H), 6.54 (bs, 1H), 5.26 (s, 1H), 3.95 (t, 2H, J=6.2 Hz, OCH$_2$), 3.24 (t, 2H, J=6.2 Hz, CONHCH$_2$), 3.12 (t, 2H, J=6.1 Hz, CONHCH$_2$), 2.87 (s, 12H), 2.36 (t, 2H, J=7.4 Hz, CH$_2$CONH), 2.04 (tt, 2H, J=7.5 Hz, J=6.3 Hz, CH$_2$CH$_2$CH$_2$), 1.41 ppm (s, 9H). $^{13}$C NMR (125 MHz, CD$_3$OD). δ 175.9, 158.6, 158.5, 150.7, 139.1, 135.3, 131.3, 130.9, 115.1, 114.4, 80.2, 68.1, 55.6, 41.4, 40.9, 40.5, 33.6, 28.8, 26.6 ppm. ESI-MS: C$_{34}$H$_{45}$N$_4$O$_4^+$ m/z=573.4 [M-H$^-$]$^+$. The analyzed data showed accordance to the previous published ones.[8]

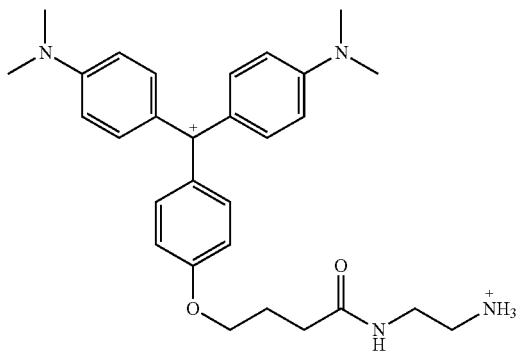

Compound 45

To a light blue solution of compound 44 (10.6 mg, 17 µmol) in EtOAc (1.0 mL) was added p-chloranil (9.4 mg, 38 µmol). The reaction mixture was refluxed for 1 h, filtered and concentrated to yield a dark blue colored oil. The crude material was dissolved in EtOH:HCl 37% (1:1 mL) and stirred for 2 h at 25° C. The reactions were monitored by LC-MS. The dark solution was diluted in water (30 mL) and washed with EtOAc (3×20 mL). The aqueous layer was lyophilized to yield a blue colored solid (8.0 mg). The crude material was purified by reversed phase column chromatography (column: Phenomenex, C18, 250×10 mm, eluent: ACN/H$_2$O/0.1% TFA). The fractions were lyophilized to yield a dark blue colored solid (6.0 mg, 52%). $^1$H NMR (500 MHz, D$_6$-DMSO). δ 8.12 (br s, 1H, CONH), 7.83 (br s, 3H, NH$_3$), 7.33 (dd, 6H, J=9.2 Hz, J=8.8 Hz, Ar—H), 7.20 (d, 2H, J=8.8 Hz, Ar—H), 7.07 (d, 4H, J=9.4 Hz, Ar—H), 4.17 (t, 2H, J=6.4 Hz, OCH$_2$), 3.33-3.24 (m, 2H, CONHCH$_2$), 3.28 (s, 12H), 2.87 (m, 2H, CH$_2$NH$_3$), 2.32 (t, 2H, J=7.4 Hz, CH$_2$CONH), 2.02 ppm (m, 2H, CH$_2$CH$_2$CH$_2$). $^{13}$C NMR (125 MHz, D$_6$-DMSO). δ 176.0, 172.4, 163.5, 156.3, 140.1, 137.4, 131.3, 126.3, 115.0, 113.6, 67.8, 38.7, 36.5, 31.5, 24.5 ppm. ESI-MS: C$_{29}$H$_{37}$N$_4$O$_2^+$ m/z=573.30 [M-H$^+$]$^+$. The analyzed data showed accordance to the previous published ones.[8]

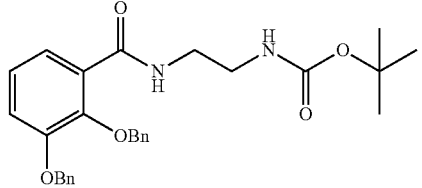

Compound 46

2,3-dihydroxybenzoic acid (140 mg, 419 µmol) was dissolved in DMF (0.5 mL). DIPEA (146 µL, 838 µmol) and HATU (176 mg, 463 µmol) were successively added and the reaction mixture was stirred for 15 min at 25° C. N-Boc-ethylenediamine (92 µL, 632 µmol) was added and the reaction mixture was stirred at 25° C. for 30 min. The solution was diluted in EtOAc (20 mL), washed with water (5 mL) and brine (3×10 mL). The organic layer was dried over anhydrous sodium sulfate, giving the crude compound as a brown oil (270 mg). The crude material was adsorbed on SiO$_2$ and purified by silica gel column chromatography (from PE:EtOAc/75:25 to PE:EtOAc/25:75). The fractions of the pure compound were collected and concentrated to yield a white solid (179 mg, 90%). $^1$H NMR (500 MHz, CDCl$_3$). δ 8.08 (bt, 1H, J=5.7 Hz, CONH), 7.70 (m, 1H), 7.47 (d, 2H, J=7.2 Hz, Ar—H), 7.44-7.30 (m, 8H, Ar—H), 7.18-7.14 (m, 2H, Ar—H), 5.17 (bs, 2H, ArOCH$_2$C$_6$H$_5$), 5.10 (bs, 2H, J=6.7 Hz, ArOCH$_2$C$_6$H$_5$), 3.36 (q, 2H, J=5.9 Hz, CONHCH$_2$), 2.67 (t, 2H, J=5.8 Hz, CH$_2$NH$_2$), 1.41 ppm (s, 9H). $^{13}$C NMR (125 MHz, CDCl$_3$). δ166.2, 156.2, 151.9, 147.0, 136.5, 136.4, 129.0, 129.0, 128.9, 128.9, 128.5, 127.8, 127.2, 124.6, 123.4, 117.4, 76.7, 71.5, 41.1, 39.8, 28.5 ppm. ESI-MS: C$_{28}$H$_{33}$N$_2$O$_5^+$ m/z=477.1287 [M+H$^+$]$^+$, Δe=0.7 ppm. The analyzed data showed accordance to the previous published ones[9].

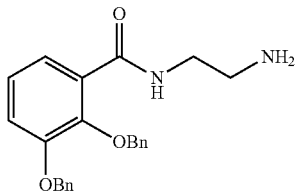

Compound 47

To a stirred suspension of compound 46 (50 mg, 105 μmol) in CH$_2$Cl$_2$ (300 μL) was added TFA (100 μL) at 25° C. The solution was stirred for 3 h. The reaction mixture was coevaporated with toluene (3×5 mL) to yield a white solid (61 mg). The crude material was dissolved in CH$_2$Cl$_2$ (10 mL) and NaOH (10 mL, 0.1 M in H$_2$O). After extraction, the organic layer was isolated, dried over MgSO$_4$, filtered and concentrated to yield a white solid (39 mg, 99%). $^1$H NMR (500 MHz, CDCl$_3$). δ 8.13 (bt, 1H, J=5.3 Hz, CONH), 7.73 (m, 1H), 7.47 (d, 2H, J=6.7 Hz, Ar—H), 7.43-7.32 (m, 8H, Ar—H), 7.15 (m, 2H, Ar—H), 5.16 (bs, 2H, ArOCH$_2$C$_6$H$_5$), 5.10 (bs, 2H, J=6.7 Hz, ArOCH$_2$C$_6$H$_5$), 3.32 (q, 2H, J=6.0 Hz, CONHCH$_2$), 2.67 (t, 2H, J=6.2 Hz, CH$_2$NH$_2$), 1.38 ppm (m, 2H). $^{13}$C NMR (125 MHz, CDCl$_3$). δ165.6, 151.8, 147.0, 136.6, 136.5, 128.9, 128.8, 128.4, 127.8, 127.5, 124.5, 123.4, 117.1, 76.5, 71.4, 42.9, 41.6 ppm. ESI-MS: C$_{23}$H$_{25}$N$_2$O$_3$$^+$ m/z=377.3 [M+H$^+$]$^+$ The analyzed data showed accordance to the previous published ones$^9$.

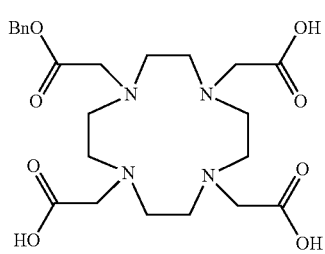

Compound 49

To a stirred solution of compound 3 (48) (2.00 g, 3.9 mmol, dissolved for 10 min) and K$_2$CO$_3$ (2.15 g, 15.6 mmol) in ACN (40 mL) and Benzyl-2-bromoacetate (0.80 mL, 5.1 mmol) was added dropwise in the suspension under Ar conditions at 0° C. and the reaction mixture was stirred for 3 h at 25° C. The reaction was monitored by TLC (CH$_2$Cl$_2$:MeOH/4:1) and LC-MS. The suspension was filtered and the filtrate was concentrated to yield a white foaming solid (2.58 g). ESI-MS: C$_{35}$H$_{59}$N$_4$O$_8$$^+$ m/z=663.5 [M+H$^+$]$^+$. The crude material (2.58 g, 3.9 mmol) was dissolved in TFA (10 mL) at 0° C. under Ar atmosphere and stirred at 25° C. for 26 h and the conversion was monitored by LC-MS. The reaction mixture was coevaporated with toluene (3×10 mL) to yield a green sticky solid (4.19 g). The crude material was dissolved in a HCl solution (0.1M in H$_2$O, 75 mL) and lyophilized to yield a yellow colored solid (3.11 g). A part of the crude material (1.00 g) was diluted in ACN/H$_2$O (1/1), filtered and purified by reversed phase column chromatography (column: Macherey-Nagel, C18, 250×40 mm, eluent: ACN/H$_2$O/0.1% HCOOH) to yield a white solid (250 mg, 40%). $^1$H NMR (500 MHz, D$_6$-DMSO). δ 7.38-7.30 (m, 5H, Ar—H), 5.11 (s, 2H, OCH$_2$), 3.65 (bs, 2H, CH$_2$COOBn), 3.49 (2×bs, 6H, CH$_2$COOH), 2.96 (bs, 8H), 2.82 ppm (bs, 4H). $^{13}$C NMR (125 MHz, D$_6$-DMSO). δ 170.9, 10 170.3, 163.3, 136.0, 128.5, 128.1, 128.0, 65.4, 55.3, 55.0, 54.0, 51.4, 50.4, 49.8, 49.3 ppm. ESI-MS: C$_{23}$H$_{35}$N$_4$O$_8$$^+$ m/z=495.24485 [M+H$^+$]$^+$, Δe=0.2 ppm.

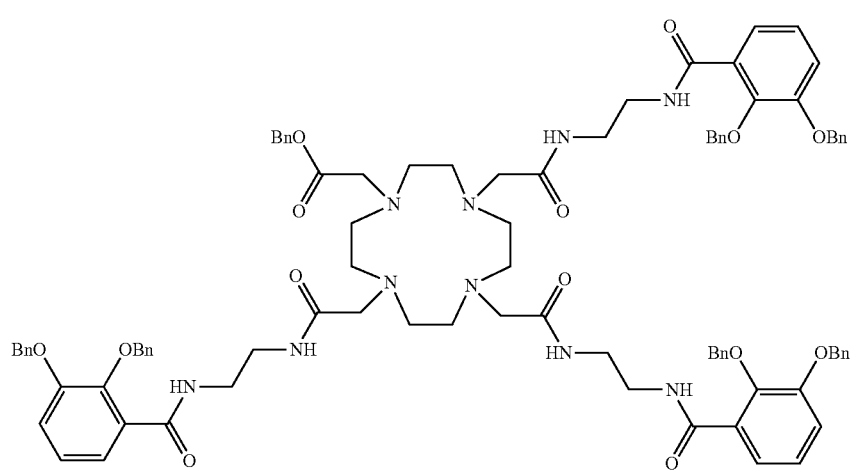

Compound 50

To a solution of compound 49 (5 mg, 10 μmol) in DMF (200 μL) were added DIPEA (6.2 μL, 36 μmol) and HATU (13 mg, 34 μmol). The reaction mixture was stirred for 15 min. The compound 47 (16 mg, 43 μmol) was added and the pale solution was stirred at 25° C. for 1 h. The reaction mixture was directly filtered and purified by reversed phase column chromatography (column: Phenomenex, C18, 250×21 mm, eluent: ACN/H$_2$O/0.1% TFA) to yield a crystallized solid (14.5 mg, 91%). A bigger scale of this reaction (0.25 g of 9) led to a diminished yield (0.47 g, 59%). $^1$H NMR (500 MHz, D$_6$-DMSO). δ 8.65 (bs, 1H, CONH), 8.26 (t, 2H, J=5.7 Hz), 8.22 (t, 1H, J=5.8 Hz), 8.10 (bs, 1H, CONH), 7.74 (bs, 2H, CONH), 7.50-7.45 (m, 6H, Ar—H), 7.43-7.22 (m, 32H, Ar—H), 7.15-7.05 (m, 6H, Ar—H), 5.20-5.15 (2×bs, 6H, ArOCH$_2$C$_6$H$_5$), 5.13-5.05 (2×bs, 2H, CH$_2$COOCH$_2$C$_6$H$_5$), 5.02-4.96 (2×bs, 6H, ArOCH$_2$C$_6$H$_5$), 4.07-2.94 ppm (m, 36H, DOTAM+NHCH$_2$CH$_2$NH). $^{13}$C NMR (125 MHz, D$_6$-DMSO). δ 166.1, 166.0, 151.6, 145.2, 145.1, 137.0, 137.0, 136.8, 135.6, 130.7, 128.5, 128.4, 128.4, 128.3, 128.3, 128.2, 128.1, 128.1, 128.0, 128.0, 127.7, 124.1, 120.9, 120.8, 116.0, 115.9, 75.2, 70.2, 65.9, 50.9, 38.4, 38.1 ppm. ESI-MS: C$_{92}$H$_{101}$N$_{10}$O$_{14}$$^+$ m/z=1569.7502 [M+H$^+$]$^+$, Δe=0.5 ppm.

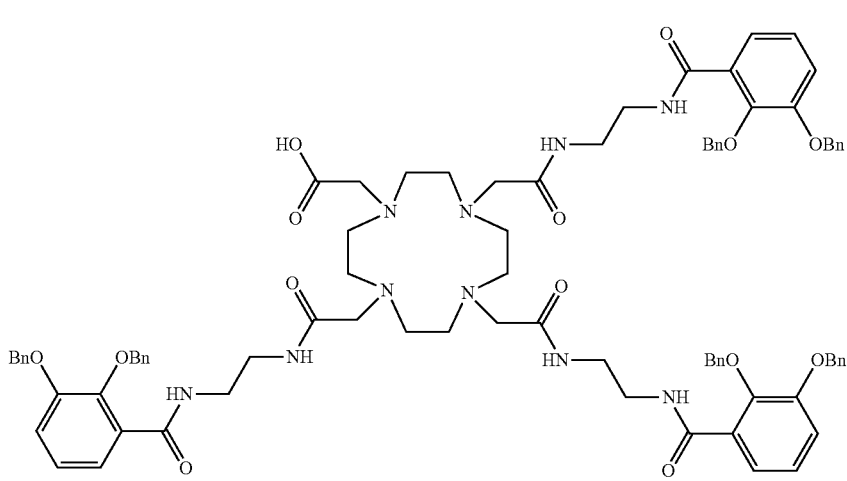

51

Compound 51

To a solution of compound 50 (50 mg, 32 μmol) in THF (300 μL) was added a LiOH solution (1 M in H$_2$O, 100 μL). The reaction was monitored by TLC (CH$_2$Cl$_2$:MeOH/8:2, UV) and the solution was stirred for 4 h at 25° C. The reaction mixture was concentrated, rediluted in ACN (1.3 mL), filtered and purified by reversed phase column chromatography (column: Phenomenex, C18, 250×21 mm, eluent: ACN/H$_2$O/0.1% TFA) to yield a colorless oil (40.7 mg, 87%). $^1$H NMR (500 MHz, D$_6$-DMSO). δ 8.52 (bs, 2H, CONH), 8.27 (t, 2H, J=5.9 Hz, CONH), 8.23 (t, 1H, J=5.9 Hz, CONH), 8.18 (bs, 1H, CONH), 7.80 (bs, 1H), 7.51-7.45 (m, 6H, Ar—H), 7.43-37 (m, 6H, Ar—H), 7.37-7.31 (m, 9H, Ar—H), 7.31-7.24 (m, 12H, Ar—H), 7.15-7.06 (m, 6H, Ar—H), 5.21-5.16 (2×bs, 6H, ArOCH$_2$C$_6$H$_5$), 5.02-4.97 (2×bs, 6H, ArOCH$_2$C$_6$H$_5$), 4.07-2.94 ppm (m, 36H, DOTAM+NHCH$_2$CH$_2$NH). $^{13}$C NMR (125 MHz, D$_6$-DMSO). δ 166.1, 166.0, 151.6, 145.2, 145.2, 137.0, 136.8, 130.8, 128.5, 128.4, 128.2, 128.0, 127.7, 124.2, 120.9, 116.0, 75.2, 75.1, 70.2, 38.8, 38.1 ppm. Rotamers were observed by the low and broad carbon signals associated to the DOTAM core unit and to the ethylendiamine in the 50-65 ppm region of the $^{13}$C NMR spectrum. NMR data were shown from a smaller scale. ESI-MS: C$_{85}$H$_{95}$N$_{10}$O$_{14}$$^+$ m/z=1479.703217 [M+H$^+$]$^+$, Δe=0.6 ppm.

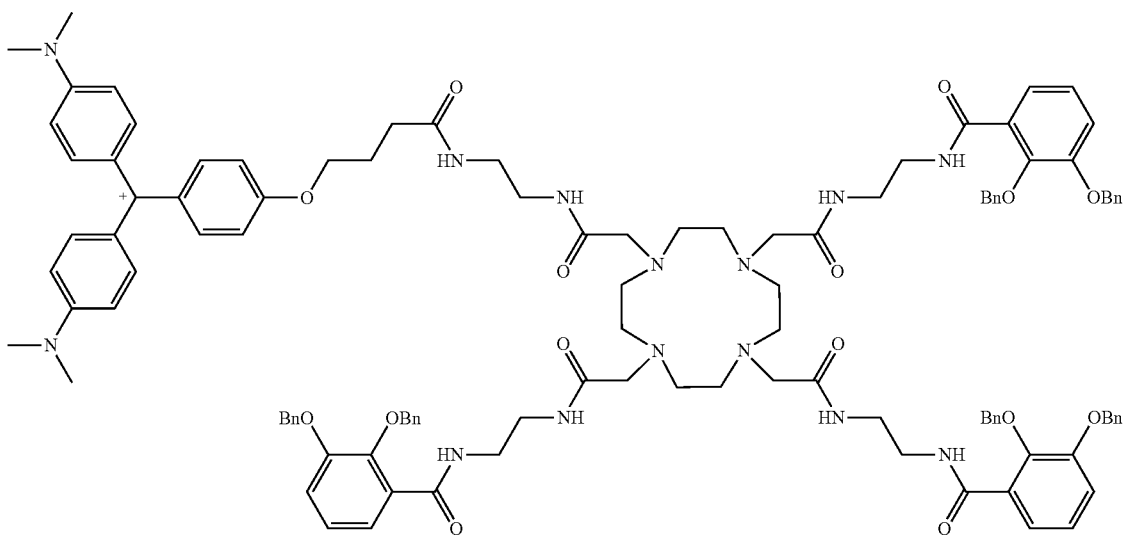

52

Compound 52

To a solution of compound 51 (10.0 mg, 6.8 μmol) in DMF (200 μL) were successively added HATU (4.4 mg, 11.6 μmol) and DIPEA (4.7 μL, 27.0 μmol). The reaction mixture was stirred at 25° C. for 10 min. A solution of compound 5 (11.1 mg, 20.3 μmol) in DMF (50 μL) was added to the reaction mixture and stirred for 1 h at 25° C. More DIPEA (4.7 μL, 27.0 μmol) and HATU (4.4 mg, 11.6 μmol) were added to the reaction mixture which was stirred for 3 further hours. The reaction mixture was filtered and purified by reversed phase column chromatography (column: Phenomenex, C18, 250×10 mm, eluent: ACN/H$_2$O/ 0.1% TFA, linear gradient from 30% to 80% ACN). The fractions were gathered and lyophilized to yield a dark blue colored solid (8.5 mg, 13.8±0.6% of water content assessed by ¹H NMR, 56%). ¹H NMR (700 MHz, D₆-DMSO). δ 8.38 (bs, 3H, CONH), 8.26 (m, 3H, CONH), 8.00-7.81 (m, 2H, CONH), 7.46 (d, 6H, J=7.3 Hz, Ar—H), 7.38 (t, 6H, J=7.5 Hz, Ar—H), 7.36-7.31 (m, 9H, Ar—H), 7.31-7.24 (m, 18H, Ar—H), 7.15-7.07 (m, 8H, Ar—H), 7.03 (d, 4H, J=9.3 Hz, $Ar_{MG}$—H), 5.21-5.14 (2×bs, 6H, $ArOCH_2C_6H_5$), 5.01-4.96 (2×bs, 6H, $ArOCH_2C_6H_5$), 4.07 (t, 2H, J=6.3 Hz, MG $CH_2NHCO$), 3.75-2.94 (m, 52H, DOTAM+$NHCH_2CH_2NH$), 2.23 (t, 2H, J=7.5 Hz, $CH_2CONH$), 2.02 ppm (m, 2H, J=7.0 Hz, J=6.0 Hz, $CH_2CH_2CH_2$). ¹³C NMR (175 MHz, D₆-DMSO). δ 176.0, 171.9, 166.1, 163.4, 156.3, 151.6, 145.1, 140.1, 137.3, 137.0, 136.7, 131.3, 130.8, 128.5, 128.3, 128.2, 128.0, 127.7, 126.2, 124.2, 120.9, 115.9, 114.9, 113.6, 75.1, 70.2, 67.8, 54.5, 49.6, 40.4, 40.0, 38.6, 38.4, 31.6, 24.6 ppm. ESI-MS: $C_{114}H_{129}N_{14}O_{15}^+$ m/z=1933.976980 [M]⁺ Δe=0.7 ppm, obtained from a smaller scale.

40.0, 38.4, 38.0, 31.6, 24.7 ppm. ESI-MS: $C_{72}H_{94}N_{14}O_{15}^{2+}$ m/z=[M+H⁺]²⁺ Δe<0.1 ppm, obtained from a smaller scale.

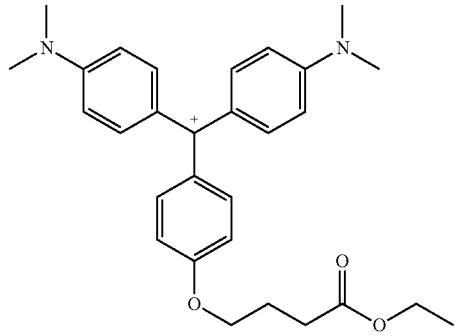

42ox

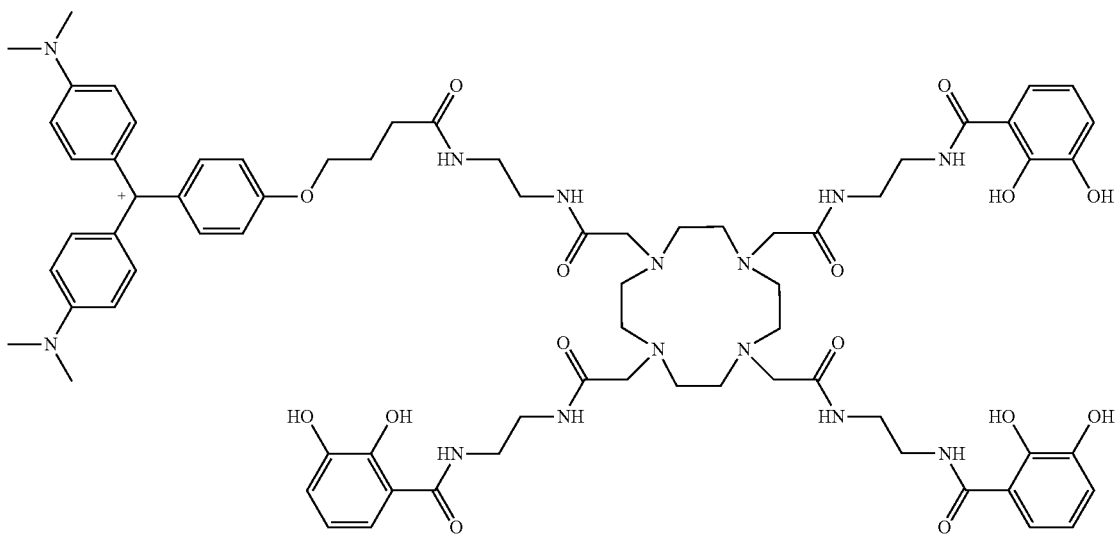

53

Compound 53

To a blue colored solution of compound 52 (2.4 mg, 6.1 μmol) in CH₂Cl₂ (200 μL) was added a BCl₃ solution (36.3 μL, 1 M in CH₂Cl₂, 36.3 μmol) at −72° C. under Ar conditions for 10 min. MeOH was added to the dark red colored solution and the mixture was stirred for 10 min at −72° C. The reaction mixture was warmed up to 25° C. and concentrated to yield a red colored solid. The crude material was diluted in MeOH (blue solution), filtered and purified by reversed phase column chromatography (column: Phenomenex, C18, 250×10 mm, eluent: ACN/H₂O/0.1% TFA) to yield a dark blue colored solid (2.5 mg, 34.7±0.5% of water content assessed by ¹H NMR, 18%). ¹H NMR (700 MHz, D₆-DMSO). δ 12.48 (bs, 2H), 9.21 (bs, 2H), 8.78 (m, 2H), 8.60-7.79 (m, 6H), 7.31 (t, 6H, J=8.7 Hz, Ar—H), 7.23 (d, 3H, J=8.2 Hz, Ar—H), 7.15 (d, 2H, J=8.8 Hz, Ar—H), 7.05 (d, 4H, J=9.4 Hz, Ar—H), 6.90 (dd, 3H, J=7.8 Hz, J=1.3 Hz, Ar—H), 6.66 (td, 3H, J=7.9 Hz, J=1.4 Hz, Ar—H), 4.11 (t, 2H, J=6.3 Hz, MG $CH_2NHCO$), 4.47-2.77 (m, 52H, DOTAM+$NHCH_2CH_2NH$), 2.27 (t, 2H, J=7.5 Hz, $CH_2CONH$), 1.98 ppm (m, 2H, $CH_2CH_2CH_2$). ¹³C NMR (175 MHz, D₆-DMSO). δ 176.0, 172.0, 169.9, 163.4, 156.3, 149.4, 146.2, 140.1, 140.1, 137.4, 131.3, 126.3, 118.8, 118.0, 117.3, 115.1, 114.9, 113.6, 67.8, 54.7, 49.5, 40.4, Compound 42ox To a light blue solution of compound 42 (100 mg, 217 μmol) in EtOAc (5 mL) was added p-chloranil (80 mg, 325 μmol). The reaction mixture was stirred at 25° C. for 5 h, filtered and concentrated to yield a dark blue colored solid. The crude material was dissolved in MeOH and purified by reversed phase column chromatography (column: Phenomenex, C18, 250×21 mm, eluent: ACN/H₂O/0.1% TFA). The fractions were lyophilized to yield a dark blue colored solid (55 mg, 45%). ¹H NMR (500 MHz, CDCl₃). δ 7.38 (d, 4H, J=9.0 Hz, Ar—H), 7.32 (d, 2H, J=8.9 Hz, Ar—H), 7.06 (d, 2H, J=8.9 Hz, Ar—H), 6.93 (d, 4H, J=9.3 Hz, Ar—H), 4.17 (m, 4H), 3.34 (s, 12H, NCH₃), 2.56 (t, 2H, J=7.2 Hz, $CH_2COO$), 2.19 (m, 2H, $CH_2CH_2CH_2$). 1.28 ppm (t, 3H, J=7.2 Hz, $CH_2CH_3$). MeOH was observed in the ¹H NMR spectrum. The analyzed data showed accordance to the previous published ones (C. Szent-Gyorgyi et al., *Nature Biotechnology* 2007, 26, 235-240).

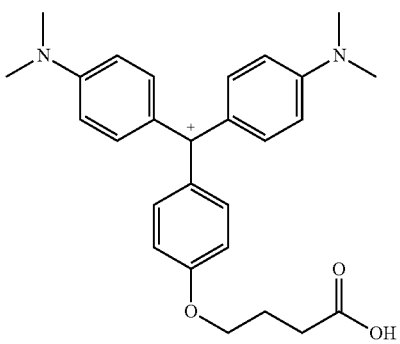

Compound 43ox

To a light blue solution of compound 42 (200 mg, 462 µmol) in DCM (5 mL) was added p-chloranil (170 mg, 691 µmol). The reaction mixture was stirred at 25° C. for 2 h and diluted in DCM (50 mL) and water (100 mL). The aqueous layer was extracted with DCM (5×100 mL) and the combined organic layers were washed with brine (100 mL), dried over MgSO$_4$, filtered and concentrated to yield a dark blue colored solid. The crude material was dissolved in ACN:H$_2$O (1:1) and purified by reversed phase column chromatography (column: Phenomenex, C18, 250×21 mm, eluent: ACN/H$_2$O/0.1% HCOOH). The fractions were lyophilized to yield a dark blue colored solid (25 mg, 11%). ESI-MS: C$_{27}$H$_{31}$N$_2$O$_3$$^+$ m/z=431.2332733 [M]$^+$, Δe=0.8 ppm.

(34.0 mg, 89.4 µmol) and DIPEA (26 µL, 149 µmol). The reaction mixture was stirred under Ar conditions at 25° C. for 10 min. A solution of compound 61 in DMF (4 mL) was added to the yellow colored solution and stirred for 26 h at 25° C. The reaction mixture was diluted in DCM and HCl (3M, 500 µL). The aqueous layer was extracted with DCM (3×10 mL) and the combined organic layers were washed with brine (10 mL), dried over MgSO$_4$, filtered and concentrated to yield a light blue colored oil (41 mg). The crude material was dissolved in DCM and purified by silica gel flash column chromatography to yield a dark blue colored solid (28 mg). The purified solid was dissolved in EtOAc (5 mL) and p-chloranil (9 mg, 37 µmol) was added to the blue solution. The reaction mixture was stirred at 25° C. for 3 h, filtered and concentrated to yield a dark blue colored solid (40 mg). The crude material was dissolved in ACN:H$_2$O (1:1), filtered and purified by reversed phase column chromatography (column: Phenomenex, C18, 250×21 mm, eluent: ACN/H$_2$O/0.1% TFA). The fractions were gathered and lyophilized to yield a dark blue colored solid (5.5 mg, 6%). $^1$H NMR (700 MHz, D$_6$-DMSO). δ 8.44 (bs, 1H), 7.88 (t, 1H, J=5.5 Hz,), 7.33 (m, 6H, Ar—H), 7.19 (d, 2H, J=8.9 Hz, Ar—H), 7.07 (d, 4H, J=9.4 Hz, Ar—H), 4.28-2.76 (m, 54H, DOTAM+PEG (—CH$_2$CH$_2$CH$_2$)$_{PEG}$+N(CH$_3$)$_2$+OCH$_2$), 2.27 (t, 2H, J=7.5 Hz, CH$_2$CH$_2$CONH), 1.99 ppm (m, 2H, HNCOCH$_2$CH$_2$CH$_2$). 1.67 (m, 2H). 1.62 (m, 2H), 1.52-1.37 ppm (2×s, 27H, C(CH$_3$)$_3$). $^{13}$C NMR (175 MHz, D$_6$-DMSO). δ 176.0, 171.3, 163.5, 156.3, 140.1, 137.4, 131.3, 126.3, 115.0, 113.6, 69.8, 69.5, 68.1, 67.9, 67.8, 40.4, 40.0, 36.3, 35.8, 31.5, 29.4, 29.0, 27.7, 24.7 ppm. TFA was

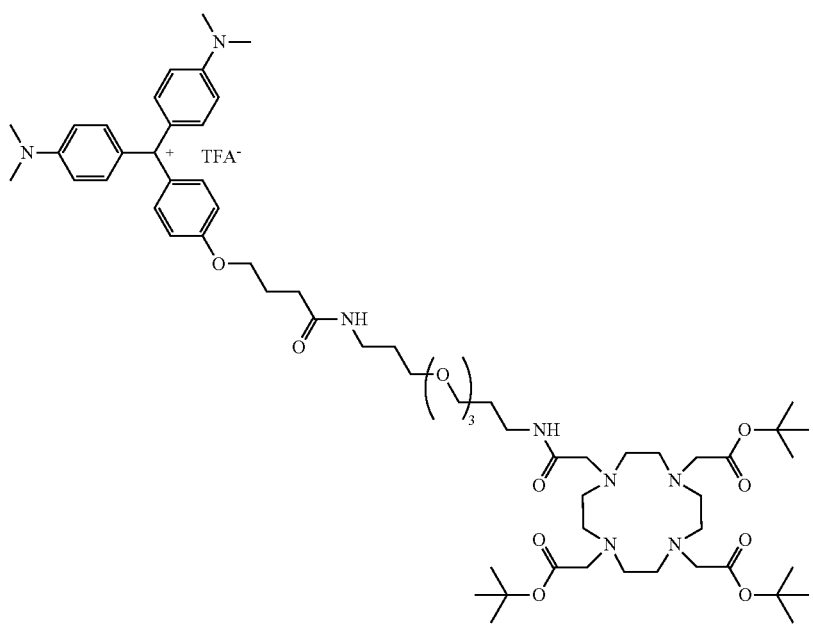

Compound 62

To a blue colored solution of compound 43 (65.6 mg, 142.1 µmol) in DMF (2 mL) were successively added HATU observed in the $^{13}$C NMR spectrum. ESI-MS: CaC$_{65}$H$_{101}$N$_8$O$_{12}$$^+$ m/z=1225.7166 [M−2H$^+$+Ca$^{2+}$]$^+$ □e<0.1 ppm and C$_{65}$H$_{103}$N$_8$O$_{12}$$^+$ m/z=1187.7699 [M$^+$]$^+$ Δe=0.3 ppm.

63

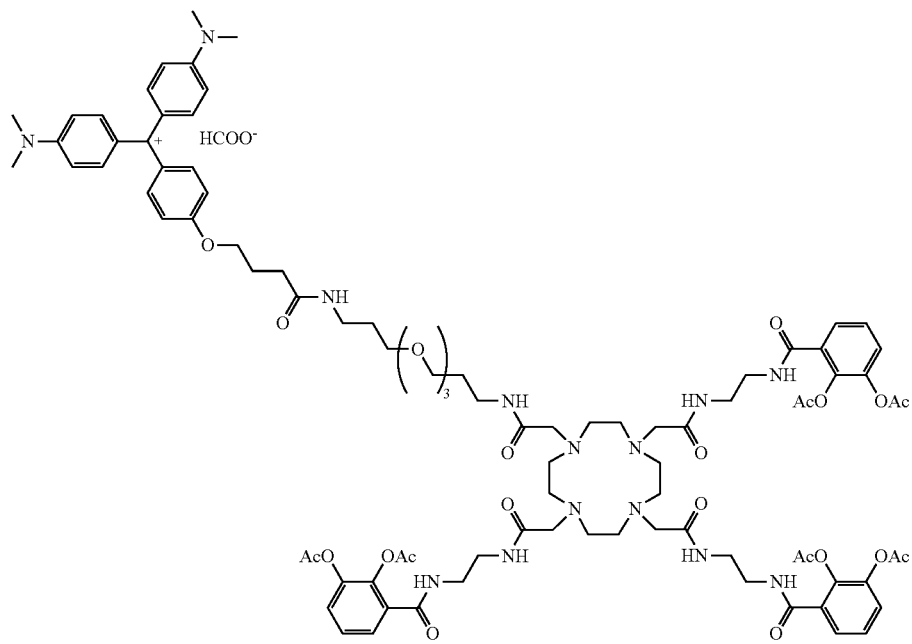

Compound 63

To a solution of compound 43 (25 mg, 54 µmol) in DMF (2 mL) were successively added HATU (21 mg, 55 µmol) and DIPEA (16 µL, 92 µmol). A solution of compound 9 in DMF (3 mL) was added to the reaction mixture and stirred for 1 h at 25° C. The reaction mixture was filtered and purified by reversed phase column chromatography (column: Phenomenex, C18, 250×21 mm, eluent: ACN/H$_2$O/ 0.1% HCOOH, linear gradient from 10% to 70% ACN). The fractions were gathered and lyophilized to yield a dark blue colored solid (6.0 mg, 10%). $^1$H NMR (700 MHz, D$_6$-DMSO). δ 8.42 (m, 4H, CONH), 7.88 (m, 1H, CONH), 7.49 (d, 2H, J=7.4 Hz), 7.41-7.28 (m, 11H, Ar—H), 7.19 (d, 2H, J=8.9 Hz, Ar—H), 7.07 (d, 4H, J=9.4 Hz, Ar—H), 3.75-2.94 (m, 66H, DOTAM+PEG (—CH$_2$CH$_2$CH$_2$)PEG+ N(CH$_3$)$_2$+OCH$_2$+NHCH$_2$CH$_2$NH), 2.30-2.20 (2×s, 18H, CH$_3$COO), 1.99 (m, 2H), 1.68-1.59 (m, 4H), 1.31-1.20 ppm (m, 4H). $^{13}$C NMR (175 MHz, D$_6$-DMSO). δ 176.1, 171.3, 168.3, 167.8, 164.9, 163.5, 156.3, 142.9, 140.1, 137.4, 131.3, 130.6, 126.3, 126.2, 126.1, 125.6, 115.0, 113.6, 69.7, 69.5, 68.1, 68.0, 67.8, 63.3, 54.6, 53.6, 49.6, 42.9, 40.4, 40.0, 38.6, 38.4, 35.8, 31.5, 29.4, 29.0, 24.7, 20.3, 20.3 ppm. ESI-MS: CaC$_{92}$H$_{119}$N$_{14}$O$_{24}$$^+$ m/z=1843.814581[M−2H$^+$+ Ca$^{2+}$]$^+$, Δe<0.1 ppm.

Figure 8:
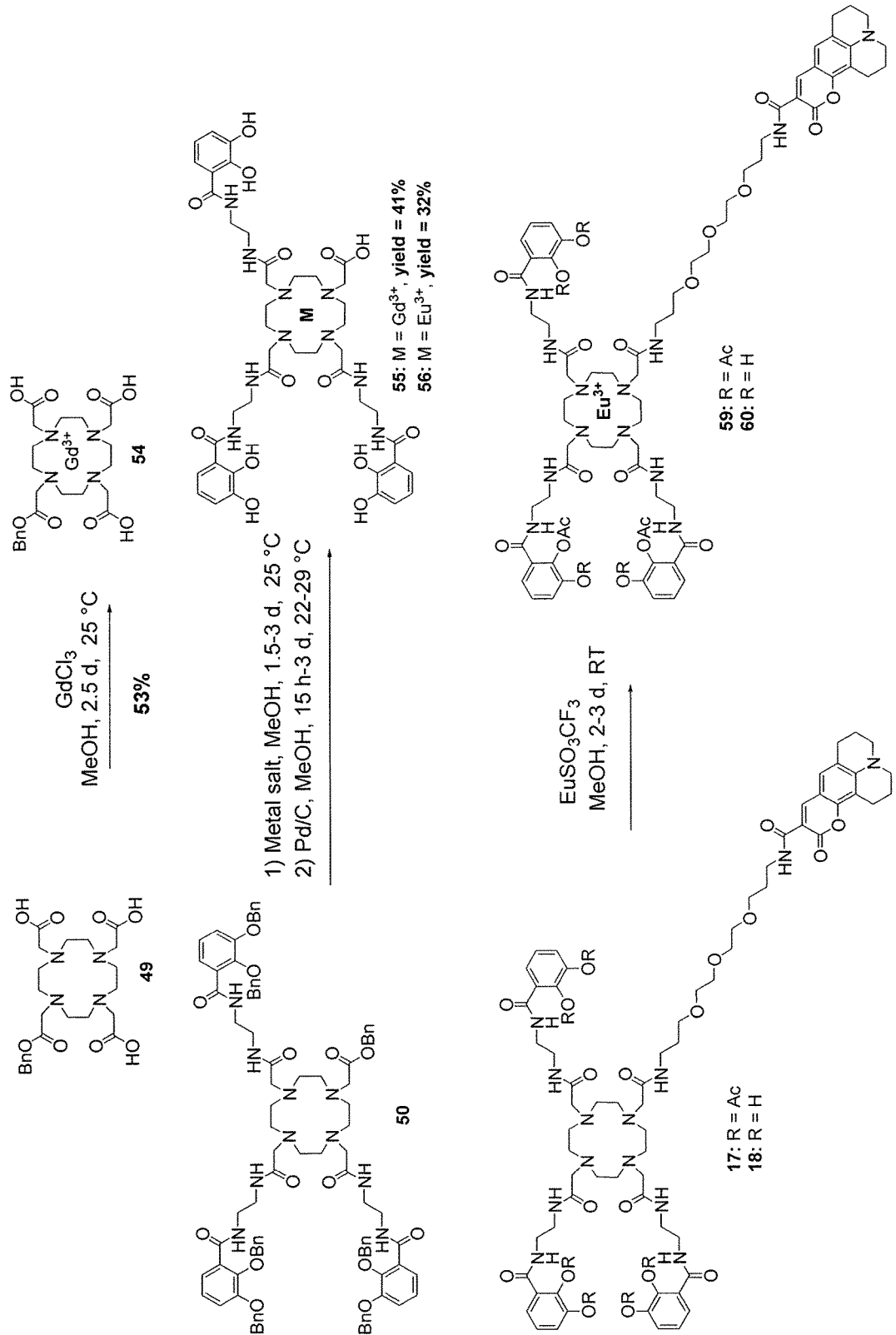
FIG. 8.

Chelating of Metal Ions in the DOTA Based Core of the Compounds According to the Present Invention, See FIG. 8.

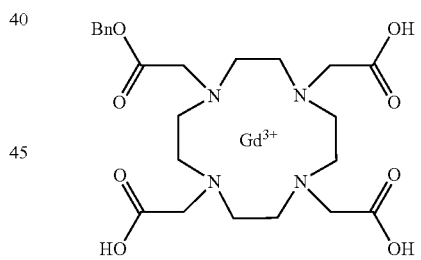

54

Compound 54

To a solution of compound 49 (10.0 mg, 20 µmol) in MeOH (100 µL) was added a GdCl$_3$, 6H$_2$O solution (7.5 mg, 20 µmol) in MeOH (400 µL). The reaction mixture was stirred for 2.5 days and was directly purified by reversed phase column chromatography (column: Phenomenex, C18, 250×10 mm, eluent: ACN/H$_2$O/0.1% TFA) to yield a white solid (7.0 mg, 53%). ESI-MS: GdC$_{23}$H$_{32}$N$_4$O$_8$ m/z=[M+ H$^+$]$^+$ Δe=1.9 ppm. $^1$H NMR (500 MHz, D$_6$-DMSO). δ 7.43-7.33 (m, 5H, Ar—H), 5.12 (s, 2H, OCH$_2$), 3.96 (bs, 4H,), 3.84 (bs, 2H), 3.65 (bs, 2H), 3.37-3.05 (2×bs, 16H). $^{13}$C NMR (125 MHz, D$_6$-DMSO). δ 169.5, 158.0, 135.5, 128.5, 128.3, 128.1, 66.1, 53.8, 53.2, 50.4, 48.8, 45.7 ppm. ESI-MS: C$_{23}$H$_{33}$GdN$_4$O$_8$$^{2+}$ m/z=325.577272 [M−H$^+$]$^{2+}$, Δe=0.1 ppm.

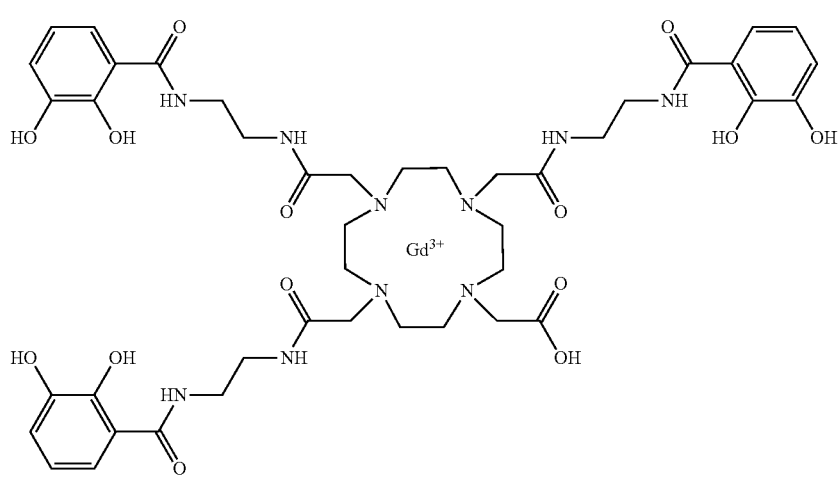

55

Compound 55

To a solution of compound 50 (10.0 mg, 6.4 μmol) in MeOH (100 μL) was added a GdCl$_3$, 6H$_2$O solution (10.0 mg, 26.9 μmol) in MeOH (100 μL). The reaction mixture was stirred for 2 days. A sodium hydroxide solution (1 M, 19 μL, pH=8) was added to the mixture which was stirred for 1 further day. The reaction mixture was purified by reversed phase column chromatography (ACN/H$_2$O/0.1% TFA, linear gradient 10%-70% ACN for 40 min) to yield a white solid (8.2 mg, 75%). $^1$H NMR data (700 MHz, D$_6$-DMSO) showed expected broadened signals. ESI-MS: C$_{85}$H$_{92}$GdN$_{10}$O$_{14}{}^+$ m/z=1633.603662 [M+H$^+$]$^+$ Δe=0.9 ppm. A part of the purified compound (2.5 mg, 1.5 μmol) was diluted in MeOH (200 μL) and hydrogenolyzed over 10% Pd/C (1.0 mg, 0.9 μmol) for 15 h at 25° C. The black suspension was filtered through celite, washed and concentrated to yield a purple colored solid. The crude material was purified by a short C18 cartridge (J. T. BAKER 7020-03). The column was washed with water/0.1% TFA (10 mL). After an ACN/0.1% TFA wash (10 mL), the solution was concentrated to yield a yellow colored solid (0.9 mg, 53%). ESI-MS: C$_{43}$H$_{57}$GdN$_{10}$O$_{14}{}^{2+}$ m/z=547.664205 [M–H$^+$]$^{2+}$, Δe=1.1 ppm.

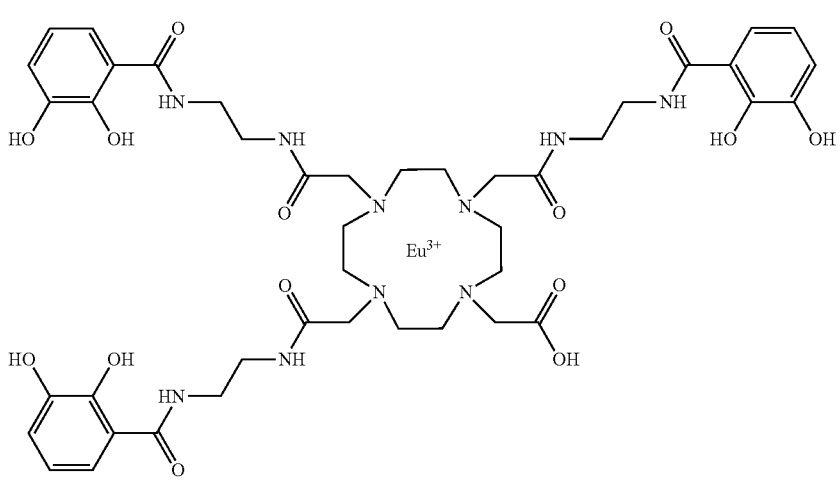

56

Compound 56

To a solution of compound 50 (25 mg, 16 μmol) in MeOH (100 μL) was added a EuSO$_3$CF$_3$ solution (19 mg, 32 μmol) in MeOH (150 μL). The reaction mixture was stirred for 2 days. The solution was hydrogenolyzed over 10% Pd/C (1.0 mg, 0.9 μmol) for 3 days at 22° C. The black suspension was filtered through celite, washed and concentrated to yield a yellow colored solid. The crude material was purified by reversed phase column chromatography (column: Phenomenex, C18, 250×10 mm, eluent: ACN/H$_2$O/0.1% TFA) to yield a white solid (5.6 mg, 32%). $^1$H NMR data (700 MHz, D$_6$-DMSO) showed broadened and expected shifted signals. ESI-MS: C$_{43}$H$_{57}$EuN$_{10}$O$_{14}{}^{2+}$ m/z=545.163119 [M–H$^+$]$^{2+}$, Δe<0.1 ppm.

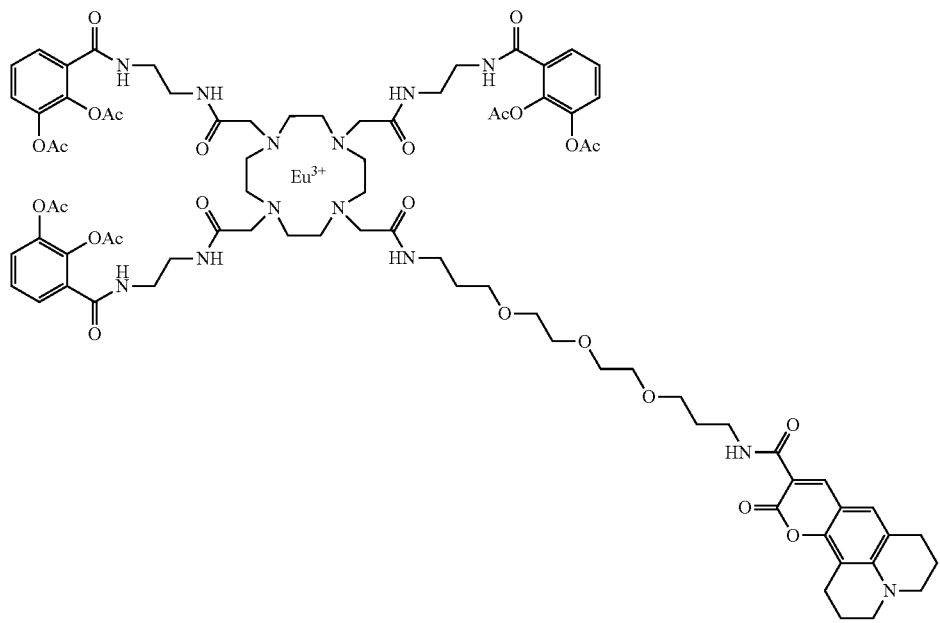

59

Compound 59

Compound 17 was solved in methanol (1 mL) and a solution of europium (III) trifluoromethanesulfonate (24.8 mg/mL, 100 µL, 2 eq) was added. The reaction mixture was stirred for two days at room temperature under argon. The reaction was checked by LC-MS and purified by HPLC to give the pure product. ESI-MS: $C_{81}H_{104}EuN_{13}O_{25}^{2+}$ m/z=906:2 $[M-H^+]^{2+}$.

Compound 60

Compound 18 was solved in dry methanol (1 mL). A solution of europium (III) trifluoromethanesulfonate (7.22 mg/120.6 µL, 2 eq) was added and stirred for three days under argon at room temperature. Then DIPEA was added and the compound 20 precipitated. The precipitate was washed, dried and separated via HPLC. ESI-MS: $C_{69}H_{93}EuN_{13}O_{19}^{2+}$ m/z=780.0 $[M-H^+]^{2+}$.

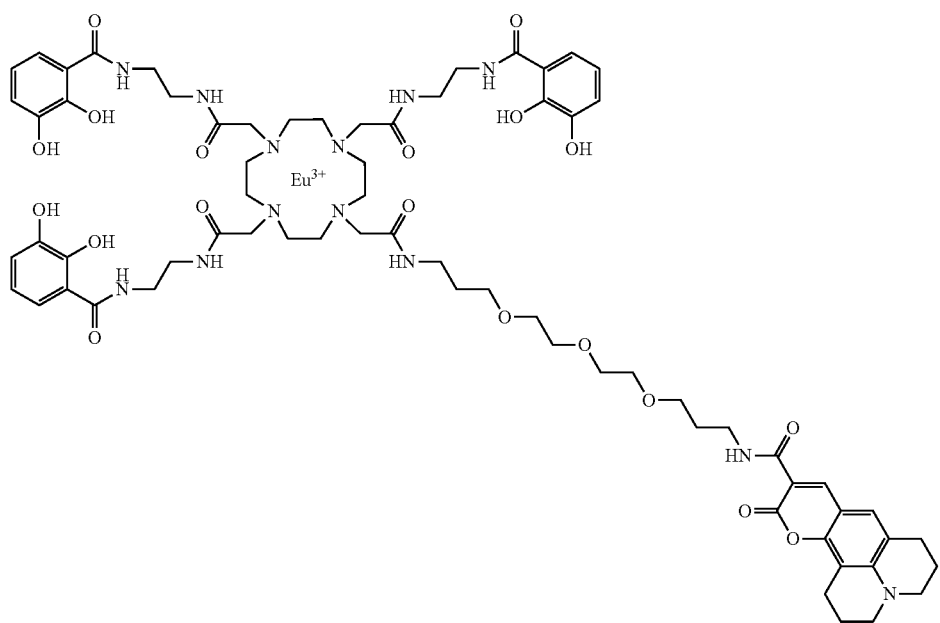

60

7 S. P. Velagapudi, et al., *J. Am. Chem. Soc.* 2011, 133, 10111-10118.
8 C. Szent-Gyorgyi et al., *Nature Biotechnology* 2007, 26, 235-240.
9 R. Schobert et al., *Tetrahedron* 2008, 64, 1711-1720.

General Method for Measuring Uptake of Coumarin 343, HHY-10 and HHY-11 in Bacteria The uptake of coumarin 343, HHY-10 and HHY-11 was investigated in gram-negative bacteria *Pseudomonas aeruginosa* PA7 (DSM 24068), *Acinetobacter baumannii* (DSM 30007, ATCC 19606) and gram-positive bacteria *Staphylococcus aureus* MRSA (DSM 11822, ICB 25701). Gram-negative bacteria were cultured overnight in Mueller Hinton Broth (M-H Broth)+1% glucose (10 g/L) or Gram-positive bacteria were cultured overnight in trypticase soy yeast extract medium (TSY-Med) at 37° C. under 5% $CO_2$ in an incubator shaker set at 180 rpm. Bacteria (from the overnight culture) were re-suspended in 10 mL of PBS buffer, to an optical density of 0.1 at 600 nm. The bacterial culture solution was transferred into 48 well plates, with each well containing 200 μL of bacteria, and 0.4 μL of either coumarin 343, HHY-10 and HHY-11 stock solutions (10 mM in PBS) were added, generating a 20 μM probe concentration. The bacteria were incubated with the probes for 1 hour at 37° C. under 5% $CO_2$ in an incubator without shaking. The bacteria were harvested by centrifuging the bacterial solutions. The resulting pellets were washed 3 times with 200 μL PBS by resuspending the pellets in PBS and centrifuging. The washed bacterial pellets were transferred into a slice, then imaged using confocal fluorescent microscopy. The intensity of the green signal from coumarin presents the relevant amount of these probes taken by the bacteria. Incubation of coumarin 343 itself with *Acinetobacter baumannii* would not lead to obvious fluorescence. However, the conjugation of siderophores, both HHY-10 and HHY-11 revealed obvious fluorescent signals in *Acinetobacter baumannii*, suggesting large quantities of imaging probes were delivered to bacteria.

Procedures for Bacterial Inhibition Assays.

All liquids and media were sterilized by autoclaving (121° C., 15 min) before use. All aqueous solutions and media were prepared using distilled, deionized, and filtered water (Millipore Milli-Q Advantage A10 Water Purification System) Mueller-Hinton No. 2 broth (MHII broth; cation adjusted) was purchased from Sigma-Aldrich (St. Louis, Mo.). Iron-deficient (−Fe) MHII broth was prepared by adding 0.8 mL of a 1 mg/mL sterile aq. solution of 2,2'-bipyridine to 49.2 mL of MHII broth. Iron-rich (+Fe) MHII broth was prepared by adding 0.8 mL of a 1 mg/mL sterile aq. solution of FeCl3 to 49.2 mL of MH II broth.

Determination of MIC90 Values by the Broth Microdilution Assay

The Fe(III)-siderophore complexes are recognized, and overcome membrane permeability barriers by entering cells through active transport mechanisms. Attachment of antibiotics to siderophores produces potential "Trojan Horse" conjugates that are anticipated to enter pathogenic bacteria via their iron uptake system, thereby circumventing the permeability-mediated drug resistance problem. Moellmann et al. demonstrated that using acylated catecholates as the siderophore components has the benefit of not only facilitating synthesis but also preventing pharmacological side effects of the catechol groups.

Antibacterial activity of the compounds was determined by measuring their minimum inhibitory concentrations (MIC90's) using the broth microdilution method according to the Clinical and Laboratory Standards Institute (CLSI, formerly the NCCLS) guidelines. Each well of a 96-well microtiter plate was filled with 40 μL of sterile broth media (−Fe or +Fe). Each test compound was dissolved in DMSO making a 10 mM solution, and then diluted with sterile broth media (−Fe or +Fe) to 75 or 150 μM. Exactly 80 μL of the compound solution was added to the first well of the microtiter plate and 1.5-fold serial dilutions were made down each row of the plate. Exactly 40 μL of bacterial inoculum (*Acinetobacter baumannii, Pseudomonas aeruginosa, Staphylococcus aureus* Starting Optical density (OD)=0.0005) was then added to each well giving a total volume of 80 μL/well. The plate was incubated at 37° C. for 48 h and then each well was examined for bacterial growth. The MIC90 was recorded as the lowest compound concentration (μM) required to inhibit 90% of bacterial growth as judged by turbidity of the culture media relative to a row of wells filled with a DMSO standard.

Compounds HHY-10 and HHY-11 were subjected to further assays to determine their minimum inhibitory concentrations (MIC) in both iron-rich and iron-deficient media (Table 1). Both compounds exhibited media antibacterial activity against Gram-negative bacter *Pseudomonas aeruginosa* PA7 (DSM 24068), *Acinetobacter baumannii* (DSM 30007, ATCC 19606) and gram-positive bacteria *Staphylococcus aureus* MRSA (DSM 11822, ICB 25701) in iron-deficient medium. HHY-11, copper complex compound, showed better inhibition affinity than HHY-10, while coumarin 343 was generally inactive (>100 μM). In iron-rich media, the inhibitory activities of the conjugates were weak, further demonstrating that iron concentration of the media may influence the expression of siderophore outer membrane receptors and may thus inversely related to the activity of siderophore-drug conjugates. Compounds 10 and 11 were also tested against *Klebsiella pneumoniae* (DSM 11678, ATCC 33495), which is able to synthesize and utilize enterobactin and its degraded product for iron uptake under iron-limited conditions. In sharp contrast to the activity enhancement observed in *P. aeruginosa, A. baumannii* and *Straph. aureus*, both compounds HHY-10 and HHY-11 were found to be inactive (>100 μM) against *K. pneumoniae*. It appears that *P. aeruginosa, A. baumannii, Straph aureus* and *K. pneumoniae*, either induced or inherently, have different abilities to use triscatecholate as a siderophore for iron uptake. The inhibitory activities of vancomycin siderophore-DOTA conjugate HHY-30 have been analyzed under similar conditions.

TABLE 1

In Vitro Antibacterial Activities of the Siderophore-DOTA Conjugates HHY-10 and HHY-11 (MIC in μM)

| | HHY-10 | | HHY-11 | | Coumarin 343 | |
|---|---|---|---|---|---|---|
| | Fe+ | Fe− | Fe+ | Fe− | Fe+ | Fe− |
| *Acinetobacter baumannii* | >100 | 15 | >100 | 9 | >100 | >100 |
| *Pseudomonas aeruginosa* | >100 | 33 | >100 | 12 | >100 | >100 |
| *Klebsiella pneumoniae* | >100 | >100 | >100 | >100 | >100 | >100 |
| *Staphylococcus aureus* | >100 | 28 | >100 | 15 | >100 | >100 |
| *P. aeruginosa* PA01/wt | >100 | 40 | >100 | 15 | >100 | >100 |
| *P. aeruginosa* PA07/wt | >100 | 40 | >100 | 15 | >100 | >100 |
| *P. aeruginosa* PA14/wt | >100 | 40 | >100 | 15 | >100 | >100 |

TABLE 1-continued

In Vitro Antibacterial Activities of the Siderophore-DOTA Conjugates HHY-10 and HHY-11 (MIC in µM)

| | HHY-10 | | HHY-11 | | Coumarin 343 | |
|---|---|---|---|---|---|---|
| | Fe+ | Fe− | Fe+ | Fe− | Fe+ | Fe− |
| P. aeruginosa PAO1/pirA | >100 | 40 | >100 | 15 | >100 | >100 |
| P. aeruginosa PAO01/fptA | >100 | 40 | >100 | 15 | >100 | >100 |

PAO1/pirA is a mutant of the wild type PAO1 with a defect in ferric enterobactin receptor (pirA), PAO1/fptA is a mutant having a mutation in the pyochelin outer membrane receptor precursor in P. aeruginosa, pyochelin is one of the two major siderophores in P. aeruginosa Imaging Bacterial Infection using a Siderophore Containing Compound Wild type P. aeruginosa (PA01) were streaked on LB agarose plates and incubated at 37° C. overnight. Single colonies were picked and inoculated in LB media. Inoculated cultures were incubated on shakers at 180 rpm at 37° C. until the optical density of the culture reached $O.D_{600}$ 0.1. IFN-β reporter mice were used to visualize the immune response to infection. The dorsal side of the mice was shaved and 5 µl of the bacterial culture was injected subcutaneously. After infection, the Cy5.5 conjugated siderophore compound (20 µg/kg of mouse body weight), see FIG. 2B, and as a control Cy5.5 compound without siderophore were injected intravenously in mice through the tail vein. Fluorescent imaging was performed at excitation and emission wavelength of 675 and 694 nm respectively. For visualizing the immune response, 150 µl of (30 mg/kg) luciferin injected in the same mice after 5 hours of infection and bioluminescent imaging was performed. Mice were sacrificed and organs such as liver, spleen, kidneys, intestine and heart were extracted and fluorescent imaging was done at excitation and emission wavelength of 675 and 694 nm respectively. Fluorescent images were processed by subtracting the auto fluorescence of the tissue using image math tool of Living image software.

Detecting Bacterial Infections using Fluorescent Siderophore Compounds

Figure 4:
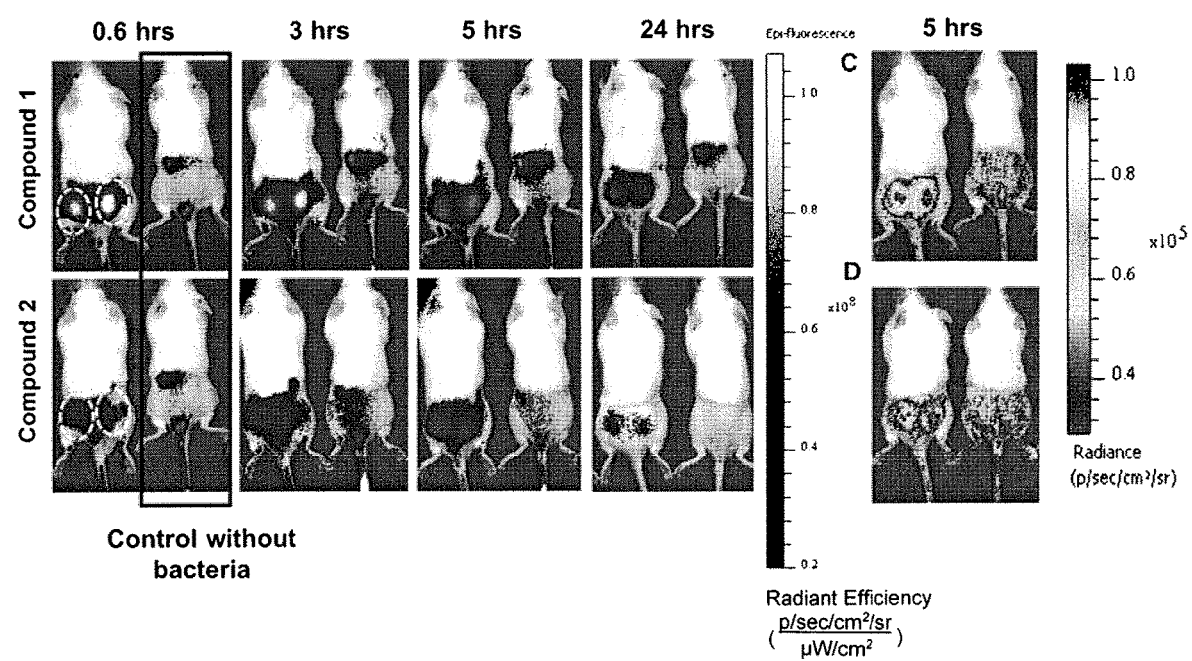
FIG. 4.

Early recognition of implant infections is important for effective treatment. Specific fluorescent labelling would permit recognition of bacteria in clinical cases of implant infections. Bacteria need iron as limiting factor for bacteremia. Pseudomonas aeruginosa recognizes a diverse set of siderophores and can utilize these compounds for iron acquisition. To monitor the bacterial infection in vivo, a novel compound was synthesized which is a 1,4,7,10-tetraazacyclododecane-1,4,7,10-tetraacetic acid amide (DOTAM) derivative. This compound was linked to siderophores, iron complexing molecules. Interferon-β luciferase reporter mice were infected subcutaneously using Pseudomonas aeruginosa. Siderophore containing agents were Cy5.5 molecules (DOTAM-Cy5.5) and were injected in mice with or without bacteria and monitored for 24 hours (FIG. 4). The fluorescence intensity of the DOTAM-Cy5.5 was the highest at the site of bacterial injection till 3 hrs and the intensity decreased gradually (FIG. 4A). Moreover, the compound without siderophores (DOTA-Cy5.5) was also visible at the site of bacteria but with weaker intensity than siderophore linked compound (FIG. 4B). To co-localize the immune response to bacteria and the DOTAM-Cy5.5 compound, bioluminescent imaging was performed in the same mice by visualizing the IFN-β production in response to the bacterial infection. Mice injected with the DOTAM-Cy5.5 and DOTA-CY5.5 alone showed luminescent signals at the bacterial injection site (FIGS. 4C and D).

Intracellular Uptake of the Compounds

The advantage of monitoring uptake with the FAP system is the fact that a fluorescent signal can only be obtained, when the dye Malachite-Green (MG) is bound to the FAP protein. As the FAP protein is expressed inside of the bacteria, a fluorescent signal can only be monitored if the MG or any conjugate of MG (p.e. DOTAM-MG, see FIG. 6) entered the cytoplasm of the bacterial cell.

The coding sequence of FAP dH6.2 6 was ordered as gene synthesis (GeneScript, USA) and cloned into the expression vector pET23b (Novagen). Chemically competent E. coli Origami DE3 (Genotype Δ(ara-leu)7697 ΔlacX74 ΔphoA PvuII phoR araD139 ahpC galE galK rpsL F′[lac⁺ lacI$^q$ pro] (DE3) gor522::Tn10 trxB (Str$^R$, Tet$^R$)) were transformed with pET_FAP dH6.2 and selected by Ampicillin resistance. E. coli Origami DE3 pET23b_FAP dH6.2 were cultured in LB medium containing 100 µg/ml Ampicillin and expression of FAP dH6.2 was induced by addition of IPTG at a final concentration of 1 mM for 4 h. Density of bacteria was adjusted to $OD_{600}$ of 2 and 100 µl of the resulting suspension was used for assaying uptake in 96 well plates. DOTAM-MG (1KF18) and MG (1KF10) were dissolved in DMSO to a concentration of 1 mM and added to the bacteria at a final concentration of 10 µM. The kinetic of fluorescence intensity was measured using TECAN Infinite Pro 200 plate reader at 610 nm excitation and 655 nm emission wavelengths.

Figure 5:
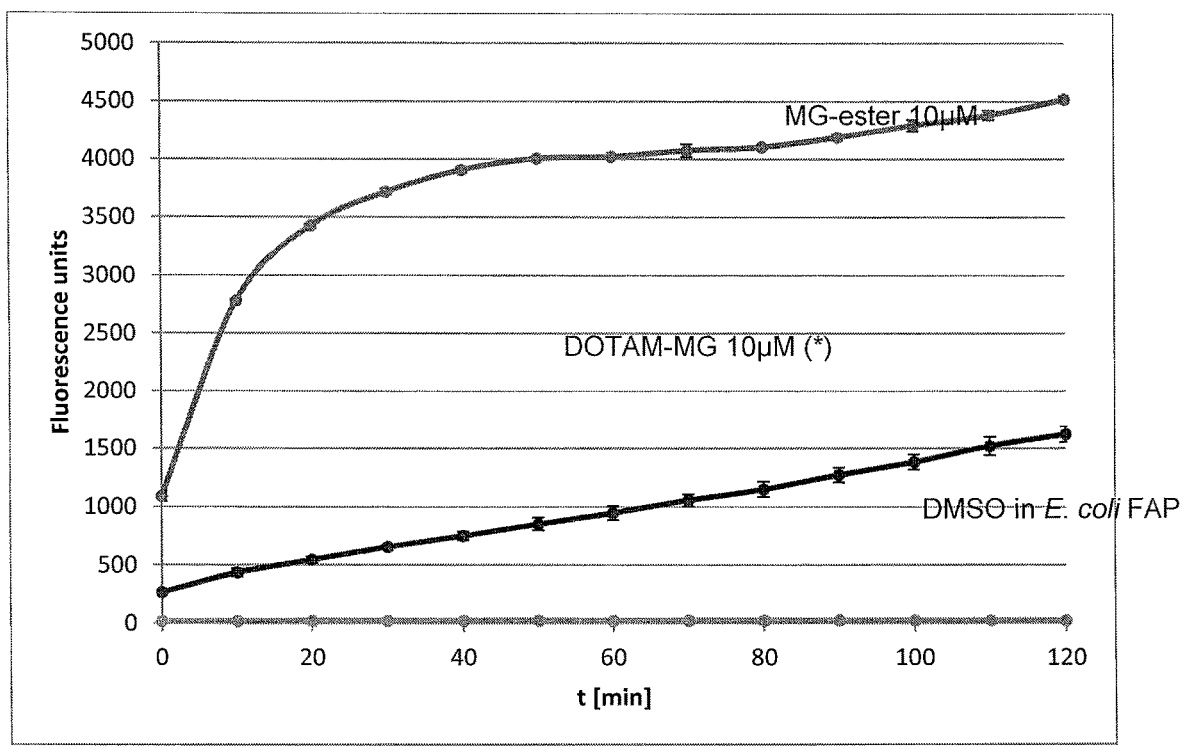
FIG. 5.

As demonstrated in FIG. 5, an uptake of IG DOTAM-MG into the cells took place. While uptake of MG-ester is by diffusion and took place rapidly, the uptake of DOTAM-MG compound shown in FIG. 6 is possible by uptake due to the siderophore only.

REFERENCES

1. Grass, G., Rensing, C. & Solioz, M. Metallic Copper as an Antimicrobial Surface. Applied and Environmental Microbiology 77, 1541-1547 (2011).
2. Jakobsche, C. E., McEnaney, P. J., Zhang, A. X. & Spiegel, D. A. Reprogramming Urokinase into an Antibody-Recruiting Anticancer Agent. ACS Chemical Biology 7, 316-321 (2011).
3. Jagadish, B., Brickert-Albrecht, G. L., Nichol, G. S., Mash, E. A. & Raghunand, N. On the synthesis of 1,4,7-tris(tert-butoxycarbonylmethyl)-1,4,7,10-tetraazacyclododecane. Tetrahedron Letters 52, 2058-2061 (2011).
4. Rho, H. S., et al. Studies on depigmenting activities of dihydroxyl benzamide derivatives containing adamantane moiety. Bioorganic & Medicinal Chemistry Letters 19, 1532-1533 (2009).
5. Albrecht, M., Baumert, M., Winkler, H. D. F., Schalley, C. A. & Frohlich, R. Hierarchical self-assembly of metallodendrimers. Dalton Transactions 39, 7220-7222 (2010).
6. Q. Yan, S. L. Schwartz, S. Maji, F. Huang, C. Szent-Gyorgyi, D. S. Lidke, K. A. Lidke and M. P. Bruchez, Chemphyschem: a European journal of chemical physics and physical chemistry, 2014, 15, 687-695.

The invention claimed is:

1. A compound having general formula (IV), in any stereoisomeric form or a mixture of stereoisomeric forms in any ratio, or a pharmaceutically acceptable salt, solvate or hydrate or a pharmaceutically acceptable formulation thereof:

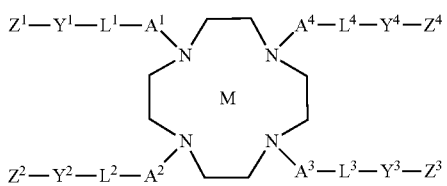
(IV)

wherein

M is a metal ion and may be present or absent, each of $A^1$, $A^2$, $A^3$, $A^4$, $L^1$, $L^2$, $L^3$, $L^4$, $Y^1$, $Y^2$, $Y^3$ and $Y^4$ may be present or absent, and $A^1$, $A^2$, $A^3$, and $A^4$ are independently of one another identical or different and are independently selected from a bond, —($C_0$-$C_4$)-alkyl-C(O)—N($R^1$)—, —($C_0$-$C_4$)-alkyl-P(O)$_t$—N($R^1$)—, —($C_0$-$C_4$)-alkyl-S(O)$_t$—N($R^1$)—, —($C_0$-$C_4$)-alkyl-N($R^2$)—C(O)—N($R^1$)— and —($C_0$-$C_4$)-alkyl-N($R^1$)—C(O)—, where $R^1$ and $R^2$ are independently selected from hydrogen, ($C_1$-$C_4$)-alkyl, ($C_3$-$C_7$)-cycloalkyl and —($C_1$-$C_4$)-alkyl-($C_3$-$C_7$)-cycloalkyl and t is 1 or 2;

$L^1$, $L^2$, $L^3$, and $L^4$ are independently of one another identical or different and independently selected from a bond, ($C_1$-$C_{18}$-alkyl, and —$(CH_2)_u$[—O—$(CH_2)_p$]$_{q-}$, where u, q and p are independently of one another identical or different and are 0, 1, 2, 3, 4, 5, 6, 7, 8, 9 or 10;

$Y^1$, $Y^2$, $Y^3$ and $Y^4$ are independently of one another identical or different, and are independently selected from a bond, —($C_0$-$C_4$)-alkyl-N($R^1$)—, —($C_0$-$C_4$)-alkyl-C(O)—N($R_1$)—, —N($R_1$)—C(O)—($C_0$-$C_6$)-alkyl-, —($C_0$-$C_4$)-alkyl-S(O)$_t$—N($R^1$)—, —($C_0$-$C_4$)-alkyl-N($R^2$)—C(O)—N($R^1$)—, —($C_0$-$C_4$)-alkyl-N($R^1$)—C(O)—,

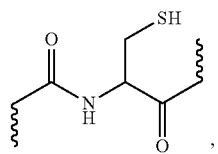

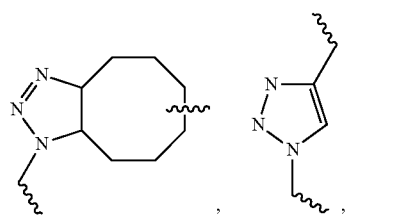

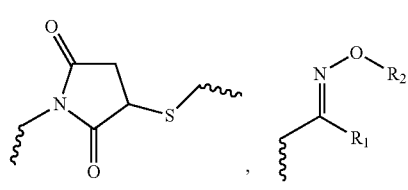

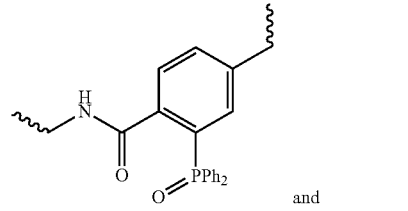
and

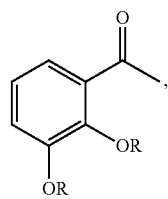

where $R^1$ and $R^2$ are independently of one another selected from hydrogen, ($C_1$-$C_4$)-alkyl, ($C_3$-$C_7$)-cycloalkyl and —($C_1$-$C_4$)-alkyl-($C_3$-$C_7$)-cycloalkyl and t is 1 or 2; or $A^4$, $L^4$ and $Y^4$ may form a cleavable linker;

$Z^1$, $Z^2$, and $Z^3$ are independently from one another identical or different and are independently selected from hydrogen, a siderophore or a siderophore forming group selected from a catecholate, a hydroxamate, an N-hydroxy-pyridone derivative, a carboxylate and

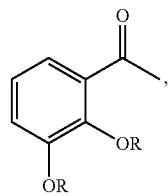

with R being Ac or H, with the proviso that at least two of $Z^1$, $Z^2$, and $Z^3$ are a siderophore or a siderophore forming group or when $A^4$, $L^4$ and $Y^4$ form a cleavable linker, at least one of $Z^1$, $Z^2$, and $Z^3$ is a siderophore or a siderophore forming group, with the proviso that when two or more siderophore forming groups are present and identical, then the two or more siderophore forming groups are a catecholate, a hydroxamate, an N-hydroxy pyridine derivative or

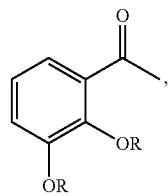

where R being Ac or H;
and

K is hydrogen, a fluorophore, a bioactive agent, an activity based probe (ABP), or a compound for bacterial inhibition.

2. The compound according to claim 1 having the general formula:

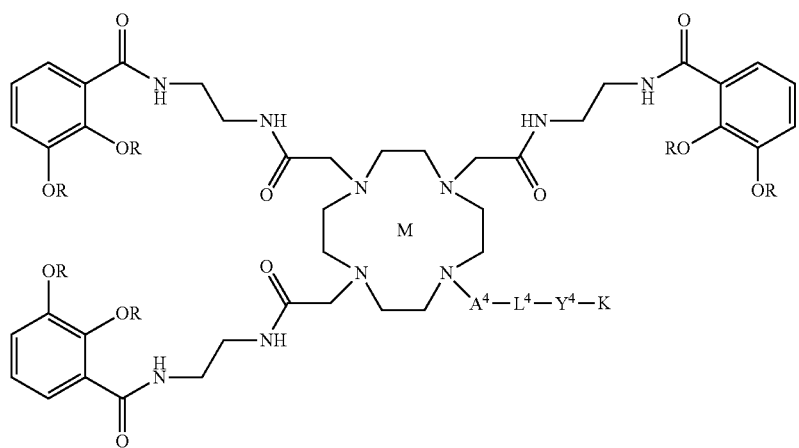
wherein M, A⁴, L⁴, Y⁴, and R are as defined in claim 1.
3. The compound according to claim 1 and which is selected from:
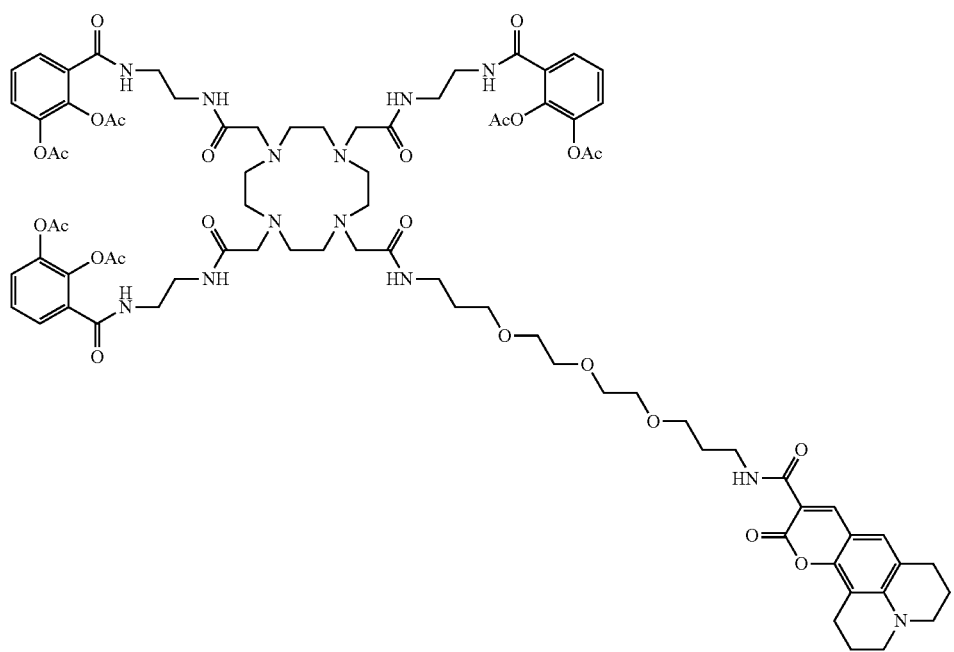

-continued
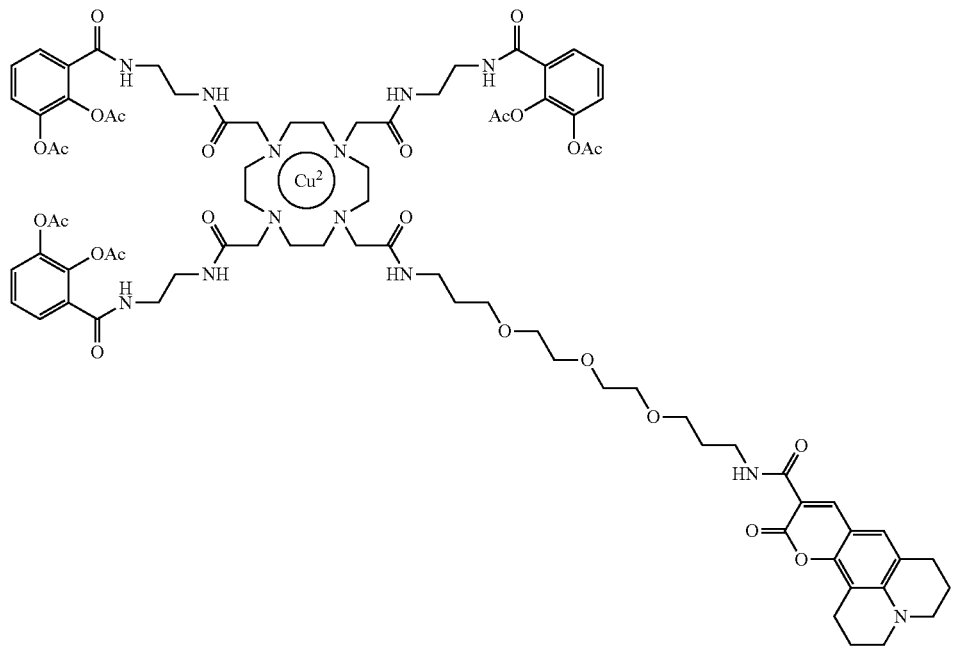
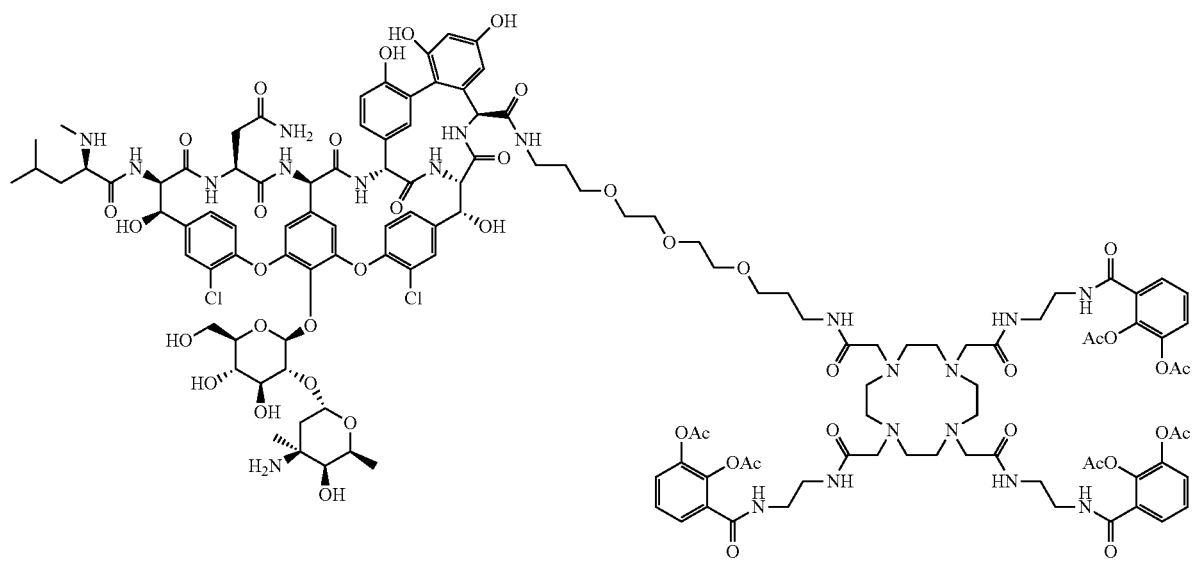

and

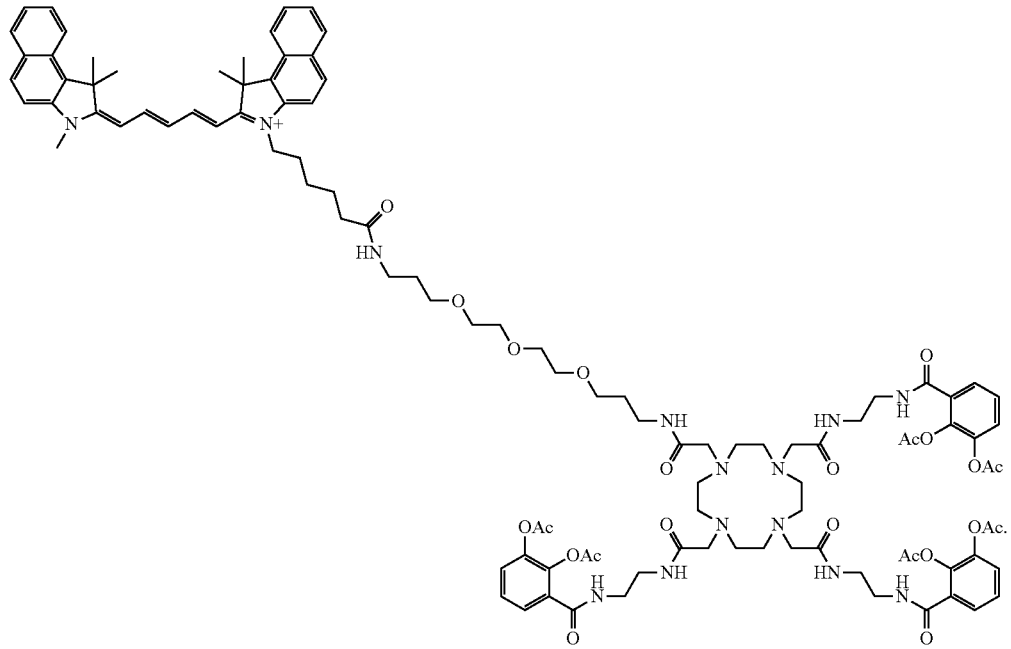

32

4. The compound of claim 1 wherein the compound for bacterial inhibition is an antibiotic.

5. A pharmaceutical composition containing a compound having general formula (IV),

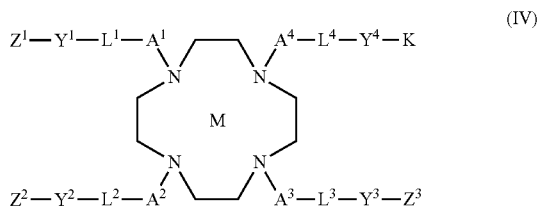

(IV)

or stereoisomers, pharmaceutically acceptable salts, solvates or hydrates thereof:

wherein

M is a metal ion and may be present or absent, each of $A^1$, $A^2$, $A^3$, $A^4$, $L^1$, $L^2$, $L^3$, $L^4$, $Y^1$, $Y^2$, $Y^3$ and $Y^4$ may be present or absent, and $A^1$, $A^2$, $A^3$, and $A^4$ are independently of one another identical or different and are independently selected from a bond, —$(C_0$-$C_4)$-alkyl-C(O)—N($R^1$)—, —$(C_0$-$C_4)$-alkyl-P(O)$_t$—N($R^1$)—, —$(C_0$-$C_4)$-alkyl-S(O)t-N(R')—, —$(C_0$-$C_4)$-alkyl-N($R^2$)—C(O)—N($R^1$)— and —$(C_0$-$C_4)$-alkyl-N($R^1$)—C(O)—, where $R^1$ and $R^2$ are independently selected from hydrogen, $(C_1$-$C_4)$-alkyl, $(C_3$-$C_7)$-cycloalkyl and —$(C_1$-$C_4)$-alkyl-$(C_3$-$C_7)$-cycloalkyl and t is 1 or 2;

$L^1$, $L^2$, $L^3$, and $L^4$ are independently of one another identical or different and independently selected from a bond, $(C_1$-$C_{18})$-alkyl, and —$(CH_2)_u$[—O—$(CH_2)_p$]$_q$—, where u, q and p are independently of one another identical or different and are 0, 1, 2, 3, 4, 5, 6, 7, 8, 9 or 10;

$Y^1$, $Y^2$, $Y^3$ and $Y^4$ are independently of one another identical or different, and are independently selected from a bond, —$(C_0$-$C_4)$-alkyl-N($R^1$)—, —$(C_0$-$C_4)$-alkyl-C(O)—N($R_1$)—, —N($R_1$)—C(O)—$(C_0$-$C_6)$-alkyl —, —$(C_0$-$C_4)$-alkyl-S(O)$_t$—N($R^1$)—, —$(C_0$-$C_4)$-alkyl-N($R^2$)—C(O)—N($R^1$)—, —$(C_0$-$C_4)$-alkyl-N($R^1$)—C(O)—,

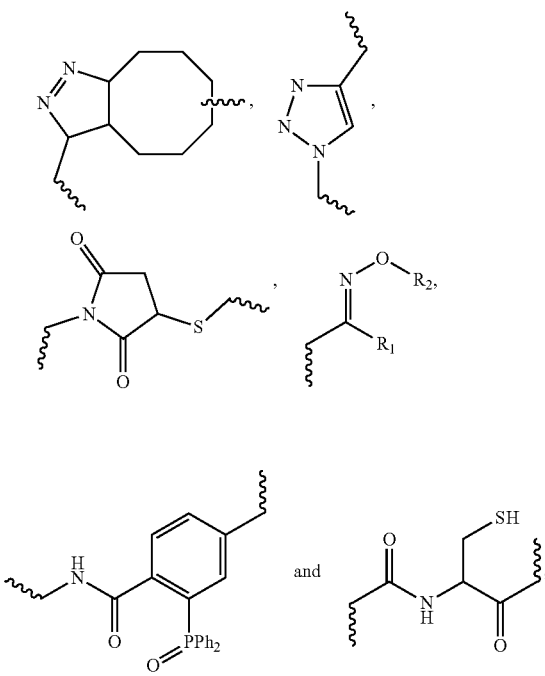

where $R^1$ and $R^2$ are independently selected from hydrogen, ($C_1$-$C_4$)-alkyl, ($C_3$-$C_7$)-cycloalkyl and —($C_1$-$C_4$)-alkyl-($C_3$-$C_7$)-cycloalkyl and t is 1 or 2;

or $A^4$, $L^4$ and $Y^4$ form a cleavable linker;

$Z^1$, $Z^2$, and $Z^3$ are independently from one another identical or different and are independently selected from hydrogen, a siderophore or a siderophore forming group selected from a catecholate, a hydroxamate, an N-hydroxy-pyridone derivative, a carboxylate, and

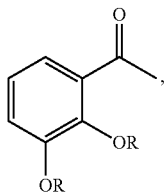

with R being Ac or H, with the proviso that at least two of $Z^1$, $Z^2$, and $Z^3$ are a siderophore or a siderophore forming group or when $A^4$, $L^4$ and $Y^4$ form a cleavable linker, at least one of $Z^1$, $Z^2$, and $Z^3$ is a siderophore or a siderophore forming group, with the proviso that when two or more siderophore forming groups are present and identical, then the two or more siderophore forming groups are a catecholate, a hydroxamate, an N-hydroxy pyridine derivative or

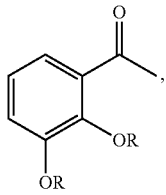

with R being Ac or H:
and

K is hydrogen, a fluorophore, a bioactive agent, an activity based probe (ABP) or a compound for bacterial inhibition.

6. A compound having general formula (IV), in any stereoisomeric form or a mixture of stereoisomeric forms in any ratio, or a pharmaceutically acceptable salt, solvate or hydrate or a pharmaceutically acceptable formulation thereof:

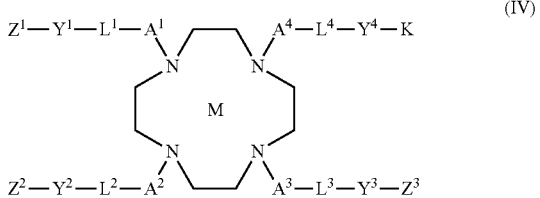

(IV)

wherein

M is a metal ion and may be present or absent, each of $A^1$, $A^2$, $A^3$, $A^4$, $L^1$, $L^2$, $L^3$, $L^4$, $Y^1$, $Y^2$, $Y^3$ and $Y^4$ may be present or absent, and $A^1$, $A^2$, $A^3$ and $A^4$ are independently of one another identical or different and are independently selected from a bond, —($C_0$-$C_4$)-alkyl-C(O)—N($R^1$)—, —($C_0$-$C_4$)-alkyl-P(O)$_t$—N($R^1$)—, —($C_0$-$C_4$)-alkyl-S(O)$_t$—N($R^1$)—, —($C_0$-$C_4$)-alkyl-N($R^2$)—C(O)—N($R^1$)- and —($C_0$-$C_4$)-alkyl-N(R')—C(O)—; where $R^1$ and $R^2$ are independently selected from hydrogen, ($C_1$-$C_4$)-alkyl, ($C_3$-$C_7$)-cycloalkyl and —($C_1$-$C_4$)-alkyl-($C_3$-$C_7$)-cycloalkyl; and t is 1 or 2;

$L^1$, $L^2$, $L^3$, and $L^4$ are independently of one another identical or different and independently selected from a bond, ($C_1$-$C_{18}$s)-alkyl, and —$(CH_2)_u$[—O—$(CH_2)_p$]$_q$—, where u, q and p are independently of one another identical or different and are 0, 1, 2, 3, 4, 5, 6, 7, 8, 9 or 10;

$Y^1$, $Y^2$, $Y^3$ and $Y^4$ are independently of one another identical or different and are independently selected from a bond, —($C_0$-$C_4$)-alkyl-N($R^1$)—, —($C_0$-$C_4$)-alkyl-C(O)—N($R_1$)—, —N($R^1$)—C(O)—($C_0$-$C_6$)-alkyl —, —($C_0$-$C_4$)-alkyl-S(O)$_t$—N($R^1$)—, —($C_0$-$C_4$)-alkyl-N($R^2$)—C(O)—N($R^1$)—, —($C_0$-$C_4$)-alkyl-N($R^1$)—C(O)—,

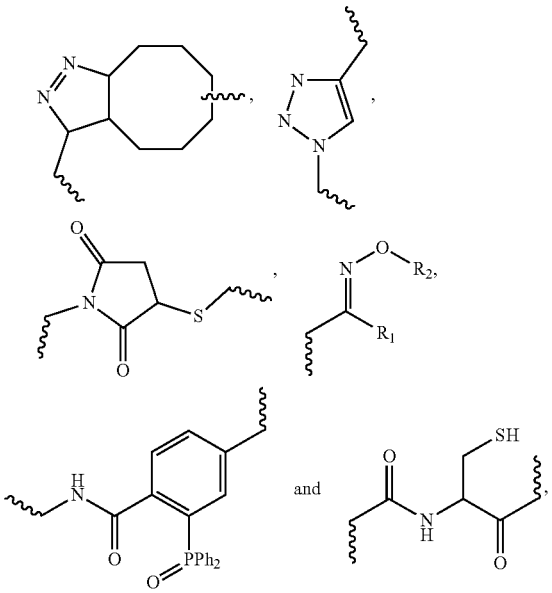

where $R^1$ and $R^2$ are independently of one another selected from hydrogen, ($C_1$-$C_4$)-alkyl, ($C_3$-$C_7$)-cycloalkyl and —($C_1$-$C_4$)-alkyl-($C_3$-$C_7$)-cycloalkyl, and t is 1 or 2;

or $A^4$, $L^4$ and $Y^4$ may form a cleavable linker;

$Z^1$, $Z^2$, and $Z^3$ are independently from one another identical or different and are independently selected from a hydrogen, a siderophore or a siderophore forming group selected from a catecholate, a hydroxamate, an N-hydroxy-pyridone derivative, a carboxylate and

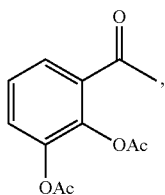

with the proviso that when two or more siderophore forming groups are present and identical, then the two or more siderophore forming groups are a catecholate, a hydroxamate, an N-hydroxy pyridine derivative or

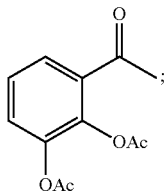

and

K is a hydrogen, a fluorophore, a bioactive agent, an activity based probe (ABP), or a compound for bacterial inhibition, where $Z^1$, $Z^2$, and $Z^3$ are each a siderophore or a siderophore forming group.

7. A diagnostic method for imaging a microorganism, comprising:

exposing the microorganism in a sample to a compound having general formula (IV), in any stereoisomeric form or a mixture of stereoisomeric forms in any ratio, or a pharmaceutically acceptable salt, solvate or hydrate or a pharmaceutically acceptable formulation thereof:

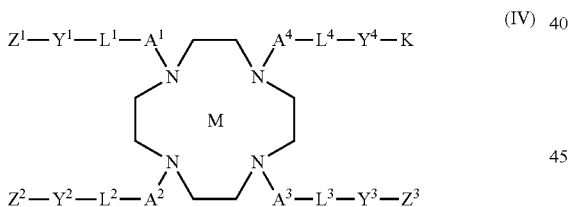

wherein

M is a metal ion and may be present or absent, each of $A^1$, $A^2$, $A^3$, $A^4$, $L^1$, $L^2$, $L^3$, $L^4$, $Y^1$, $Y^2$, $Y^3$ and $Y^4$ may be present or absent, and $A^1$, $A^2$, $A^3$ and $A^4$ are independently of one another identical or different and are independently selected from a bond, —($C_0$-$C_4$)-alkyl-C(O)—N($R^1$)—, —($C_0$-$C_4$)-alkyl-P(O)$_t$—N($R^1$)—, —($C_0$-$C_4$)-alkyl-S(O)$_t$—N($R^1$)—, —($C_0$-$C_4$)-alkyl-N($R^2$)—C(O)—N($R^1$)— and —($C_0$-$C_4$)-alkyl-N($R^1$)—C(O)—where $R^1$ and $R^2$ are independently selected from hydrogen, ($C_1$-$C_4$)-alkyl, ($C_3$-$C_7$)-cycloalkyl and —($C_1$-$C_4$)-alkyl-($C_3$-$C_7$)-cycloalkyl; and t is 1 or 2;

$L^1$, $L^2$, $L^3$, and $L^4$ are independently of one another identical or different and independently selected from a bond, ($C_1$-$C_{18}$)-alkyl, and —($CH_2$)$_u$[—O—($CH_2$)$_p$]$_q$—, where u, q and p are independently of one another identical or different and are 0, 1, 2, 3, 4, 5, 6, 7, 8, 9 or 10;

$Y^1$, $Y^2$, $Y^3$ and $Y^4$ are independently of one another identical or different and are independently selected from a bond, —($C_0$-$C_4$)-alkyl-N($R^1$)—, —($C_0$-$C_4$)-alkyl-C(O)—N($R_1$)—, —N($R_1$)—C(O)—($C_0$-$C_6$)-alkyl —, —($C_0$-$C_4$)-alkyl-S(O)$_t$—N($R^1$)—, —($C_0$-$C_4$)-alkyl-N($R^2$)—C(O)—N($R^1$)—, —($C_0$-$C_4$)-alkyl-N($R^1$)—C(O)—,

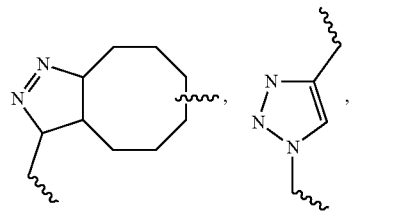

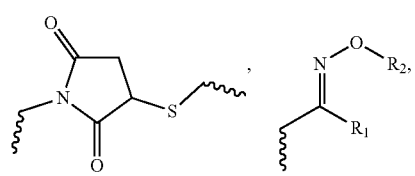

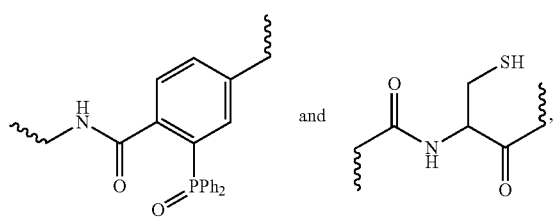

where $R^1$ and $R^2$ are independently of one another selected from hydrogen, ($C_1$-$C_4$)-alkyl, ($C_3$-$C_7$)-cycloalkyl and —($C_1$-$C_4$)-alkyl-($C_3$-$C_7$)-cycloalkyl, and t is 1 or 2;

or $A^4$, $L^4$ and $Y^4$ may form a cleavable linker;

$Z^1$, $Z^2$, and $Z^3$ are independently from one another identical or different and are independently selected from a hydrogen, a siderophore or a siderophore forming group selected from a catecholate, a hydroxamate, an N-hydroxy-pyridone derivative, a carboxylate and

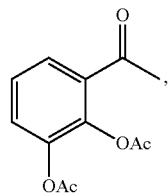 [SMILES: CC(=O)Oc1cccc(C(C)=O)c1OC(C)=O]

with the proviso that when two or more siderophore forming groups are present and identical, then the two or more siderophore forming groups are a catecholate, a hydroxamate, an N-hydroxy pyridine derivative or

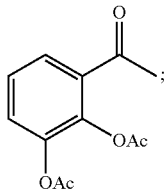

and

K is a hydrogen, a fluorophore, a bioactive agent, an activity based probe (ABP), or a compound for bacterial inhibition; and determining an uptake of the compound by the microorganism or an activity of the compound on the microorganism by imaging the microorganism.

8. The diagnostic method according to claim 7 wherein the step of determining is performed by one or more of optical imaging, molecular imaging and/or chemical imaging.

9. The diagnostic method according to claim 7 wherein M in the compound is a positively charged metal ion selected from the group consisting of Gd, Yb, Mn, Cr, Cu, Fe, Pr, Nd, Sm, Tb, Y, Dy, Ho, Er, Eu, Ga, $^{68}$Ga, $^{64}$Cu, $^{99m}$Tc, $^{177}$Lu, $^{67}$Ga, $^{111}$In, and $^{99}$Mo.

10. The diagnostic method according to claim 7, wherein the step of determining is performed by a method selected from the group consisting of single-photon emission computed tomography (SPECT), positron emission tomography (PET), and magnetic resonance imaging (MRI).

11. A method for the transport of a compound of interest into bacteria, yeast, fungi or a plant comprising exposing the bacteria, the yeast, the fungi, or the plant to a vehicle which includes a compound according to claim 1.

12. The method according to claim 11 wherein M in the compound is a positively charged metal ion selected from the group consisting of Gd, Yb, Mn, Cr, Cu, Fe, Pr, Nd, Sm, Tb, Y, Dy, Ho, Er, Eu, Ga, $^{68}$Ga, $^{64}$C, $^{99m}$Tc, $^{177}$Lu, $^{67}$Ga, $^{111}$In, and $^{99}$Mo.

* * * * *